United States Patent [19]

DeGrado et al.

[11] Patent Number: 5,691,329
[45] Date of Patent: Nov. 25, 1997

[54] COMPOUNDS CONTAINING BASIC AND ACIDIC TERMINI USEFUL AS FIBRINOGEN RECEPTOR ANTAGONISTS

[75] Inventors: William Frank DeGrado, Moylan, Pa.; Chu-Biao Xue, Hockessin, Del.

[73] Assignee: The DuPont Merck Pharmaceutical Company, Wilmington, Del.

[21] Appl. No.: 694,043

[22] Filed: Aug. 8, 1996

Related U.S. Application Data

[60] Division of Ser. No. 343,159, Nov. 22, 1994, Pat. No. 5,563,158, which is a continuation-in-part of Ser. No. 174,552, Dec. 28, 1993, abandoned.

[51] Int. Cl.$^6$ .................. C07D 401/02; A61K 31/44; A61K 31/445
[52] U.S. Cl. .................. 514/210; 514/255; 514/326; 514/340; 540/1; 540/200; 544/367; 544/369; 546/214; 546/271.4; 546/272.1
[58] Field of Search ............... 540/1, 200; 544/367, 544/369; 546/214, 271.4, 272.1; 514/210, 255, 326, 340

[56] References Cited

U.S. PATENT DOCUMENTS

| | | | |
|---|---|---|---|
| 5,039,805 | 8/1991 | Alig et al. | 546/224 |
| 5,276,049 | 1/1994 | Himmelsbach et al. | 514/392 |
| 5,281,585 | 1/1994 | Himmelsbach et al. | 514/79 |

FOREIGN PATENT DOCUMENTS

| | | |
|---|---|---|
| 2008311 | 7/1990 | Canada . |
| 2061661 | 9/1992 | Canada . |
| 2074685 | 1/1993 | Canada . |
| 2075590 | 2/1993 | Canada . |
| 2093770 | 10/1993 | Canada . |
| 2094773 | 10/1993 | Canada . |
| 2101179 | 1/1994 | Canada . |
| 525629 | 1/1988 | European Pat. Off. . |
| 381033 | 8/1990 | European Pat. Off. . |
| 445796 | 9/1991 | European Pat. Off. . |
| 478328 | 4/1992 | European Pat. Off. . |
| 478362 | 4/1992 | European Pat. Off. . |
| 478363 | 4/1992 | European Pat. Off. . |
| 512829 | 11/1992 | European Pat. Off. . |
| 512831 | 11/1992 | European Pat. Off. . |
| 513810 | 11/1992 | European Pat. Off. . |
| 580008 | 1/1994 | European Pat. Off. . |
| WO 9307867 | 10/1992 | WIPO . |
| WO 9318057 | 9/1993 | WIPO . |
| WO 9402472 | 2/1994 | WIPO . |
| WO 9408577 | 4/1994 | WIPO . |
| WO 9412181 | 6/1994 | WIPO . |

OTHER PUBLICATIONS

Alig et al. *J. Med. Chem.* (1992) 35: 4393–4407.
Hartman et al. *J. Med. Chem.* (1992) 35: 4640–4642.

*Primary Examiner*—Zinna Northington Davis

[57] ABSTRACT

This invention relates to novel compounds containing basic and acidic termini, pharmaceutical compositions containing such compounds, processes for preparing such compounds, and to methods of using these compounds, alone or in combination with other therapeutic agents, for the inhibition of platelet aggregation, as thrombolytics, and/or for the treatment of thromboembolic disorders.

10 Claims, No Drawings

COMPOUNDS CONTAINING BASIC AND ACIDIC TERMINI USEFUL AS FIBRINOGEN RECEPTOR ANTAGONISTS

CROSS REFERENCE TO EARLIER FILED APPLICATION

This is a division of U.S. patent application Ser. No. 08/343,159, filed Nov. 22, 1994 now U.S. Pat. No. 5,563,158 which application is a continuation-in part of U.S. patent application Ser. No. 08/174,552, filed Dec. 28, 1993 now abandoned. The disclosure of this earlier filed application is hereby incorporated herein by reference.

FIELD OF THE INVENTION

This invention relates to novel compounds containing basic and acidic termini, pharmaceutical compositions containing such compounds, processes for preparing such compounds, and to methods of using these compounds, alone or in combination with other therapeutic agents, for the inhibition of platelet aggregation, as thrombolytics, and/or for the treatment of thromboembolic disorders.

BACKGROUND OF THE INVENTION

Hemostasis is the normal physiological process in which bleeding from an injured blood vessel is arrested. It is a dynamic and complex process in which platelets play a key role. Within seconds of vessel injury, resting platelets become activated and are bound to the exposed matrix of the injured area by a phenomenon called platelet adhesion. Activated platelets also bind to each other in a process called platelet aggregation to form a platelet plug. This platelet plug can stop bleeding quickly, but it must be reinforced by fibrin for long-term effectiveness, until the vessel injury can be permanently repaired.

Thrombosis may be regarded as the pathological condition wherein improper activity of the hemostatic mechanism results in intravascular thrombus formation. Activation of platelets and the resulting platelet aggregation and platelet factor secretion has been associated with different pathophysiological conditions including cardiovascular and cerebrovascular thromboembolic disorders, for example, the thromboembolic disorders associated with unstable angina, myocardial infarction, transient ischemic attack, stroke, atherosclerosis, and diabetes. The contribution of platelets to these disease processes stems from their ability to form aggregates, or platelet thrombi, especially in the arterial wall following injury.

Platelets are known to play an essential role in the maintenance of hemostasis and in the pathogenesis of arterial thrombosis. Platelet activation has been shown to be enhanced during coronary thrombolysis. This can lead to delayed reperfusion and reocclusion. Clinical studies with aspirin, ticlopidine, and a monoclonal antibody for platelet glycoprotein IIb/IIIa provide biochemical evidence for platelet involvement in unstable angina, early stage acute myocardial infarction, transient ischemic attack, cerebral ischemia, and stroke.

Platelets are activated by a wide variety of agonists resulting in platelet shape change, secretion of granular contents and aggregation. Aggregation of platelets serves to further focus clot formation by concentrating activated clotting factors in one site. Several endogenous agonists, including adenosine diphosphate (ADP), serotonin, arachidonic acid, thrombin, and collagen, have been identified. Because of the involvement of several endogenous agonists in activating platelet function and aggregation, an inhibitor which acts against all agonists would represent a more efficacious antiplatelet agent than currently available antiplatelet drugs, which are agonist-specific.

Current antiplatelet drugs are effective against only one type of agonist; these include aspirin, which acts against arachidonic acid; ticlopidine, which acts against ADP; thromboxane $A_2$ synthetase inhibitors or receptor antagonists, which act against thromboxane $A_2$; and hirudin, which acts against thrombin.

Recently, a common pathway for all known agonists has been identified, namely the platelet glycoprotein IIb/IIIa complex (GPIIb/IIIa or IIb/IIIa), which is the membrane protein mediating platelet aggregation. A recent review of GPIIb/IIIa is provided by Phillips et al. (1991) Cell 65: 359–362. The development of a GPIIb/IIIa antagonist represents a promising new approach for antiplatelet therapy. Recent studies in man with a monoclonal antibody for GPIIb/IIIa indicate the antithrombotic benefit of a GPIIb/IIIa antagonist.

There is presently a need for a GPIIb/IIIa-specific antiplatelet agent which inhibits the activation and aggregation of platelets in response to any agonist. Such an agent should represent a more efficacious antiplatelet therapy than the currently available agonist-specific platelet inhibitors.

GPIIb/IIIa on unstimulated platelets does not bind soluble proteins, but GPIIb/IIIa in activated platelets is known to bind four soluble adhesive proteins, namely fibrinogen, von Willebrand factor, fibronectin, and vitronectin. The binding of fibrinogen and von Willebrand factor to GPIIb/IIIa causes platelets to aggregate. The binding of fibrinogen is mediated in part by the Arg-Gly-Asp (RGD) recognition sequence which is common to the adhesive proteins that bind GPIIb/IIIa.

Several RGD-peptidomimetic compounds have been reported which block fibrinogen binding and prevent the formation of platelet thrombi. For example, see: Alig et al. U.S. Pat. No. 5,039,805; Alig et al. European Patent Application Publication Number 381,033 A1; Alig et al. Canadian Patent Application 2,061,661 (European Patent Application Publication Number 505,868); Alig et al. European Patent Application Publication Number 445,796 A2; European Patent Application Publication Number 525,629 (Canadian Patent Application Publication Number 2,074,685); European Patent Application publication Number 4,512,831; PCT Patent Application 9307867.

Compounds of the present invention represent novel structures which bind to the glycoprotein IIb/IIIa receptor, thereby preventing fibrinogen from binding at its platelet receptor site, leading to efficacy in the prevention of blood platelet aggregation and subsequent clotting disorders.

SUMMARY OF THE INVENTION

This invention provides novel aromatic compounds containing basic and acidic termini of Formula I (described below) which are useful as antagonists of the platelet glycoprotein IIb/IIIa complex. The compounds of the present invention inhibit the binding of fibrinogen to platelet glycoprotein IIb/IIIa complex and inhibit the aggregation of platelets. The present invention also includes pharmaceutical compositions containing such compounds of Formula I, and methods of using such compounds for the inhibition of platelet aggregation, as thrombolytics, and/or for the treatment of thromboembolic disorders.

The present invention also includes methods of treating thromboembolic disorders by administering a compound of Formula I in combination with one or more second therapeutic agents selected from: anti-coagulants such as warfarin or heparin; anti-platelet agents such as aspirin, piroxicam or ticlopidine; thrombin inhibitors such as boropeptides, hirudin or argatroban; or thrombolytic agents such as tissue plasminogen activator, anistreplase, urokinase or streptokinase; or combinations thereof.

Also included in the present invention are pharmaceutical kits comprising one or more containers containing pharmaceutical dosage units comprising a compound of Formula I, for the treatment of thromboembolic disorders.

DETAILED DESCRIPTION OF THE INVENTION

This invention provides novel aromatic compounds containing basic and acidic termini of Formula I (described below) which are useful as antagonists of the platelet glycoprotein IIb/IIIa complex. The compounds of the present invention inhibit the binding of fibrinogen to the platelet glycoprotein IIb/IIIa complex and inhibit the aggregation of platelets. The present invention also includes pharmaceutical compositions containing such compounds of Formula I, and methods of using such compounds for the inhibition of platelet aggregation, as thrombolytics, and/or for the treatment of thromboembolic disorders.

This invention provides compounds of Formula I:

$$R^1-U-V \diagdown N(R^{6e}) \diagup C(R^7) \diagdown R^8 \diagup C(R^{7a}) \diagdown R^9 \diagup R^{10} \quad (I)$$

or pharmaceutically acceptable salt or prodrug forms thereof wherein:

$R^1$ is selected from:

[structures]

$n$ is 2, 3, or 4;
$p$ is 4, 5, or 6;
$q$ is 1, 2, or 3;
$r$ is 2, 3, or 4;

$R^6$ and $R^{6a}$ are independently selected from: H, $C_1$-$C_{10}$ alkyl, $C_2$-$C_6$ alkenyl, $C_3$-$C_{11}$ cycloalkyl, $C_4$-$C_{11}$ cycloalkylalkyl, aryl, aryl($C_1$-$C_6$ alkyl)-, ($C_1$-$C_7$ alkyl)carbonyl, arylcarbonyl, ($C_1$-$C_{10}$ alkoxy)carbonyl, $C_4$-$C_{11}$ cycloalkoxycarbonyl, $C_7$-$C_{11}$ bicycloalkoxycarbonyl, aryloxycarbonyl, aryl($C_1$-$C_{10}$ alkyl)carbonyl, or aryl ($C_1$-$C_{10}$ alkoxy)carbonyl;

$R^7$, and $R^{7a}$ are selected independently from: H or $C_1$-$C_4$ alkyl;

$R^{6b}$ is selected from: H, $C_1$-$C_{10}$ alkyl, $C_2$-$C_6$ alkenyl, $C_3$-$C_{11}$ cycloalkyl, $C_4$-$C_{15}$ cycloalkylalkyl, aryl, aryl ($C_1$-$C_{10}$ alkyl)-;

$R^{6e}$ is selected from: H, $C_1$-$C_{10}$ alkyl, $C_2$-$C_6$ alkenyl, $C_3$-$C_{11}$ cycloalkyl, $C_4$-$C_{15}$ cycloalkylalkyl, aryl, aryl ($C_1$-$C_{10}$ alkyl)-;

Alternatively, $R^{6e}$ and $R^7$ can be taken together with the nitrogen and carbon atom to which they are attached to form a 5–7 membered nitrogen heterocycle, said heterocycle optionally including one additional N, O or S atom.

U is selected from:
—$CH_2$—$CH_2$—$CH_2$— substituted with 0–4 $R^3$,
—X—$CH_2$—$CH_2$— substituted with 0–4 $R^3$,
—$CH_2$—X—$CH_2$— substituted with 0–4 $R^3$,
—$CH_2$—$CH_2$—X— substituted with 0–4 $R^3$,
—$CH_2$—CH=CH— substituted with 0–4 $R^3$,
—CH=CH—$CH_2$— substituted with 0–4 $R^3$,
—$CH_2$—C≡C— substituted with 0–2 $R^3$,
—C≡C—$CH_2$— substituted with 0–2 $R^3$,
—CH=CH— substituted with 0–2 $R^3$,
—C≡C—,
—$CH_2$—$CH_2$— substituted with 0–4 $R^3$,
—X—$CH_2$— substituted with 0–2 $R^3$,
—$CH_2$—X— substituted with 0–2 $R^3$,
—X—, or
—$CH_2$— substituted with 0–2 $R^3$;

X is selected from: O, S, S(=O), $SO_2$, $SO_2N(R^{6c})$, $N(R^{6c})SO_2$, $N(R^{12})$, C(=O)$N(R^{6c})$, $N(R^{6c})C(=O)$; with the proviso that when $R^1$ is

[structure]

then X is not S, S(=O), or $SO_2N(R^{6c})$; with the proviso that when $R^1$ is

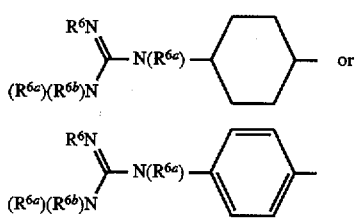

then U is not optionally substituted —CH$_2$—CH$_2$—CH$_2$—, —X—CH$_2$—CH$_2$—, —CH$_2$—X—CH$_2$—, —CH$_2$—CH$_2$—X—, —CH$_2$—CH=CH—, —CH=CH—CH$_2$—, —CH$_2$—C≡C—, or —C≡C—CH$_2$—;

$R^{12}$ and $R^{13}$ are independently selected from: H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, aryl, $C_2$–$C_6$ alkenyl, $C_3$–$C_{11}$ cycloalkyl, $C_4$–$C_{15}$ cycloalkylalkyl, aryl($C_1$–$C_{10}$ alkyl), arylcarbonyl, $C_4$–$C_{11}$ cycloalkoxycarbonyl, $C_7$–$C_{11}$ bicycloalkoxycarbonyl, aryloxycarbonyl, or aryl ($C_1$–$C_{10}$ alkoxy)carbonyl;

$R^{6c}$ is selected from: H, $C_1$–$C_{10}$ alkyl, $C_2$–$C_6$ alkenyl, $C_3$–$C_{11}$ cycloalkyl, $C_4$–$C_{15}$ cycloalkylalkyl, aryl, aryl ($C_1$–$C_{10}$ alkyl)-;

$R^3$ is independently selected from: H, $C_1$–$C_6$ alkyl, $C_3$–$C_6$ cycloalkyl, $C_4$–$C_{11}$ cycloalkylalkyl, aryl, aryl($C_1$–$C_6$ alkyl) -;

V is selected from:

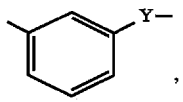

the phenyl ring being substituted with 0–2 $R^5$;

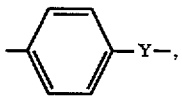

the phenyl ring being substituted with 0–2 $R^5$; or —Q—Y—;

Q is a 5–10 membered heterocyclic ring system having 1–4 heteroatoms selected independently from O, S, and N, said heterocyclic ring being substituted with 0–2 $R^5$;

Y is selected from: C(=O) or S(O)$_2$;

$R^5$ is selected independently from H, F, Cl, Br, I, CF$_3$, CN, CHO, CO$_2$$R^{5a}$, C(=O)$R^{5a}$, CONHR$^{5a}$, CON($R^{5a}$)$_2$, OC(=O)$R^{5a}$, OCO$_2$$R^{5a}$, OR$^{5a}$, OC(=O)N($^{5a}$)$_2$, OCH$_2$CO$_2$$R^{5a}$, CO$_2$CH$_2$CO$_2$$R^{5a}$, N($R^{12}$)$R^{5a}$, NO$_2$, NR$^{5a}$C(=O)$R^{5a}$, NR$^{5a}$C(=O)OR$^{5a}$, NR$^{5a}$SO$_2$N($R^{12}$)$R^{5a}$, NR$^{5a}$SO$_2$$R^{5b}$, SR$^{5a}$, S(=O)$R^{5b}$, SO$_2$$R^{5b}$, SO$_2$N($R^{5a}$)$_2$, $C_1$ to $C_{10}$ alkyl, $C_2$ to $C_6$ alkenyl, $C_2$ to $C_6$ alkynyl, $C_3$ to $C_{11}$ cycloalkyl, $C_4$ to $C_{15}$ cycloalkylalkyl, aryl, aryl($C_1$–$C_{10}$ alkyl), $C_1$ to $C_6$ alkyl substituted with 0–4 $R^{5c}$,
$C_2$ to $C_6$ alkenyl substituted with 0–4 $R^{5c}$,
$C_2$ to $C_6$ alkynyl substituted with 0–4 $R^{5c}$,
$C_3$ to $C_{11}$ cycloalkyl substituted with 0–3 $R^{5c}$,
$C_4$ to $C_{15}$ cycloalkylalkyl substituted with 0–3 $R^{5c}$,
aryl substituted with 0–3 $R^{5c}$,
aryl($C_1$–$C_{10}$ alkyl) substituted with 0–3 $R^{5c}$;

$R^{5a}$ is selected from: H, $C_1$ to $C_{10}$ alkyl, $C_2$ to $C_6$ alkenyl, $C_3$ to $C_{11}$ cycloalkyl, $C_4$ to $C_{15}$ cycloalkylalkyl, aryl, or aryl($C_1$–$C_{10}$ alkyl);

$R^{5b}$ is selected from: $C_1$ to $C_{10}$ alkyl, $C_2$ to $C_6$ alkenyl, $C_3$ to $C_{15}$ cycloalkyl, $C_4$ to $C_{11}$ cycloalkylalkyl, aryl, or aryl ($C_1$–$C_{10}$ alkyl);

$R^{5c}$ is selected from: H, halogen, $C_1$–$C_4$ alkyl, $C_1$–$C_3$ haloalkyl, CN, $C_1$–$C_4$alkoxy, NO$_2$;

$R^8$ is selected from:

H;

$C_1$–$C_6$ alkyl substituted with 0–4 $R^{3a}$;
$C_2$–$C_6$ alkenyl substituted with 0–4 $R^{3a}$;
$C_2$–$C_6$ alkynyl substituted with 0–4 $R^{3a}$;
$C_3$–$C_8$ cycloalkyl substituted with 0–4 $R^{3a}$;
aryl substituted with 0–4 $R^{3a}$;
aryl($C_1$–$C_6$ alkyl)-substituted with 0–4 $R^{3a}$;
a 5–10 membered heterocyclic ring system having heteroatoms selected independently from O, S, and N, said heterocyclic ring being substituted with 0–3 $R^{3a}$;
$C_1$–$C_6$ alkyl substituted with a 5–10 membered heterocyclic ring system having 1–4 heteroatoms selected independently from O, S, and N, said heterocyclic ring being substituted with 0–4 $R^{3a}$;
($R^{12}$) ($R^{5a}$)NC(=O)—;
piperidyl-C(=O)—;

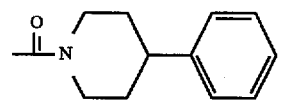

substituted with 0–4 $R^{3a}$; or

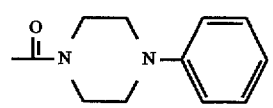

substituted with 0–4 $R^{3a}$;

$R^{3a}$ is selected from H, halogen, $C_1$–$C_8$ alkyl, $C_2$–$C_6$ alkenyl, $C_3$–$C_{11}$ cycloalkyl, $C_4$–$C_{11}$ cycloalkylalkyl, aryl, aryl($C_1$–$C_6$ alkyl)-;

$R^9$ is selected from:

H,
—$R^{15}$,
—N($R^{6d}$)C(=O)—O—$R^{15a}$,
—N($R^{6d}$)C(=O)—$R^{15}$,
—N($R^{6d}$)C(=O)—NH—$R^{15}$,
—N($R^{6d}$)NH—C(=O)—O—$R^{15a}$,
—N($R^{6d}$)NH—C(=O)—$R^{15}$,
—N($R^{6d}$)NH—C(=O)—NH—$R^{15}$,
—N($R^{6d}$)S(=O)$_2$—O—$R^{15b}$,
—N($R^{6d}$)S(=O)$_2$—$R^{15}$,
—N($R^{6d}$)C(=S)NHR$^{15}$,
—N($R^{6d}$)P(=S)OR$^{15a}$,
—N($R^{6d}$)P(=O)OR$^{15a}$,
—N($R^{6d}$)P(=S) ($R^{15a}$)$_2$,
—N($R^{6d}$)P(=O) ($R^{15a}$)$_2$,
—N($R^{12}$) ($R^{5a}$),
—CH=CH—$R^{15}$, or
—C≡C—$R^{15}$;

with the proviso that when U is —C(=O)NH— or —C(=O)NHCH$_2$—, then $R^9$ is not H;

$R^{6d}$ is selected from: H, $C_1$–$C_{10}$ alkyl, $C_2$–$C_6$ alkenyl, $C_3$–$C_{11}$ cycloalkyl, $C_4$–$C_{15}$ cycloalkylalkyl, aryl, aryl ($C_1$–$C_{10}$ alkyl)-;

$R^{15}$ is selected from:

H, $C_1$-$C_8$ alkyl substituted with 0–4 $R^{3a}$, $C_2$-$C_8$ alkenyl substituted with 0–4 $R^{3a}$, $C_2$-$C_8$ alkynyl substituted with 0–4 $R^{3a}$, $C_3$-$C_8$ cycloalkyl substituted with 0–4 $R^{3a}$, aryl substituted with 0–4 $R^{3a}$, aryl($C_1$-$C_6$ alkyl)-substituted with 0–4 $R^{3a}$, a 5–10 membered heterocyclic ring system having 1–4 heteroatoms selected independently from O, S, and N, said heterocyclic ring being substituted with 0–3 $R^{3a}$, $C_1$-$C_6$ alkyl substituted with a 5–10 membered heterocyclic ring system having 1–4 heteroatoms selected independently from O, S, and N, said heterocyclic ring being substituted with 0–4 $R^{3a}$;

$R^{15a}$ is selected from:

$C_1$-$C_8$ alkyl substituted with 0–4 $R^{3a}$, $C_2$-$C_8$ alkenyl substituted with 0–4 $R^{3a}$, $C_2$-$C_8$ alkynyl substituted with 0–4 $R^{3a}$, $C_3$-$C_8$ cycloalkyl substituted with 0–4 $R^{3a}$, aryl substituted with 0–4 $R^{3a}$, aryl($C_1$-$C_6$ alkyl)-substituted with 0–4 $R^{3a}$, a 5–10 membered heterocyclic ring system having 1–4 heteroatoms selected independently from O, S, and N, said heterocyclic ring being substituted with 0–3 $R^{3a}$, $C_1$-$C_6$ alkyl substituted with a 5–10 membered heterocyclic ring system having 1–4 heteroatoms selected independently from O, S, and N, said heterocyclic ring being substituted with 0–4 $R^{3a}$;

$R^{10}$ is selected from $CO_2R^{16}$, $CO_2R^{13b}$, $SO_3H$, tetrazolyl, or $PO_3H$;

$R^{16}$ is selected from: H, $C_1$ to $C_{10}$ alkyl, $C_3$ to $C_{11}$ cycloalkyl, aryl, aryl($C_1$ to $C_6$ alkyl)-, $C_3$ to $C_{10}$ alkylcarbonyloxyalkyl, $C_3$ to $C_{10}$ alkoxycarbonyloxyalkyl, $C_2$ to $C_{10}$ alkoxycarbonyl, $C_5$ to $C_{10}$ cycloalkylcarbonyloxyalkyl, $C_5$ to $C_{10}$ cycloalkoxycarbonyloxyalkyl, $C_5$ to $C_{10}$ cycloalkoxycarbonyl, aryloxycarbonyl, aryloxycarbonyloxy($C_1$ to $C_6$ alkyl)-, arylcarbonyloxy ($C_1$ to $C_6$ alkyl)-, $C_5$ to $C_{12}$ alkoxyalkylcarbonyloxyalkyl, (5-($C_1$-$C_5$ alkyl)-1,3-dioxa-cyclopenten-2-one-yl)methyl, (5-aryl-1,3-dioxa-cyclopenten-2-one-yl)methyl, or $(R^{12})(R^{5a})N$—($C_1$-$C_{10}$ alkyl)-.

$R^{13b}$ is selected independently from:

—$CH(R^{36})OC(=O)R^{37}$;

—$CH(R^{36})OC(=O)OR^{38}$;

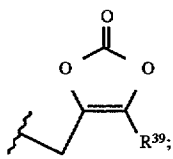

$R^{36}$ is $C_1$-$C_4$ linear alkyl or H;

$R^{37}$ is selected from:

(a) H;

(b) $C_1$-$C_8$ alkyl or $C_3$-$C_8$ cycloalkyl, said alkyl or cycloalkyl being substituted with 1–2 groups independently selected from:

(i) $C_1$-$C_4$ alkyl;

(ii) $C_3$-$C_8$ cycloalkyl;

(iii) $C_1$-$C_5$ alkoxy;

(iv) aryl substituted with 0–2 groups independently selected from: halogen, phenyl, $C_1$-$C_6$ alkyl, $C_1$-$C_6$ alkoxy, $NO_2$, —S($C_1$-$C_5$ alkyl), —S(=O) ($C_1$-$C_5$ alkyl), —$SO_2$($C_1$-$C_5$ alkyl), —OH, —$N(R^{12})$ ($R^{5a}$), —$CO_2R^{5a}$, —$C(=O)N(R^{12})$ ($R^{5a}$), or —$C_vR_w$ where v=1 to 3 and w=1 to (2v+1);

(c) aryl substituted with 0–2 groups independently selected from: halogen, phenyl, $C_1$-$C_6$ alkyl, $C_1$-$C_6$ alkoxy, $NO_2$, —S($C_1$-$C_5$ alkyl), —S(=O) ($C_1$-$C_5$ alkyl), —$SO_2$($C_1$-$C_5$ alkyl), —OH, —$N(R^{12})$ ($R^{5a}$), —$CO_2R^{5a}$, —$C(=O)N(R^{12})$ ($R^{5a}$), or —$C_vR_w$ where v=1 to 3 and w=1 to (2v+1);

$R^{38}$ is selected from:

(a) $C_1$-$C_8$ alkyl or $C_3$-$C_8$ cycloalkyl, said alkyl or cycloalkyl being substituted with 1–2 groups independently selected from:

(i) $C_1$-$C_4$ alkyl;

(ii) $C_3$-$C_8$ cycloalkyl;

(iii) $C_1$-$C_5$ alkoxy;

(iv) aryl substituted with 0–2 groups independently selected from: halogen, phenyl, $C_1$-$C_6$ alkyl, $C_1$-$C_6$ alkoxy, $NO_2$, —S($C_1$-$C_5$ alkyl), —S(=O) ($C_1$-$C_5$ alkyl), —$SO_2$($C_1$-$C_5$ alkyl), —OH, —$N(R^{12})$ ($R^{5a}$), —$CO_2R^{5a}$, —$C(=O)N(R^{12})$ ($R^{5a}$), or —$C_vR_w$ where v=1 to 3 and w=1 to (2v+1);

(b) aryl substituted with 0–2 groups independently selected from: halogen, phenyl, $C_1$-$C_6$ alkyl, $C_1$-$C_6$ alkoxy, $NO_2$, —S($C_1$-$C_5$ alkyl), —S(=O) ($C_1$-$C_5$ alkyl), —$SO_2$($C_1$-$C_5$ alkyl), —OH, —$N(R^{12})$ ($R^{5a}$), —$CO_2R^{5a}$, —$C(=O)N(R^{12})$ ($R^{5a}$), or —$C_vR_w$ where v=1 to 3 and w=1 to (2v+1);

$R^{39}$ is $C_1$-$C_4$ alkyl, benzyl, or phenyl.

Preferred compounds of the present invention are those compounds described above of Formula I, or a pharmaceutically acceptable salt or prodrug form thereof, wherein:

$R^1$ is selected from:

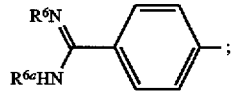

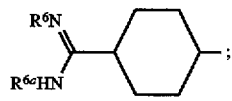

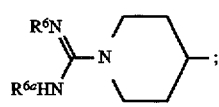

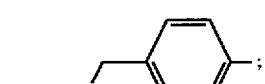

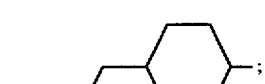

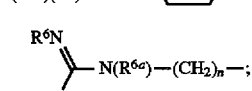

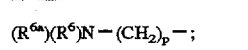

-continued

R⁶—N⟨piperidine⟩—(CH₂)q—;

R⁶N=C(NHR⁶ᵃ)—N⟨piperazine⟩N—;

R⁶N=C(NHR⁶ᵃ)—N(R⁶ᵃ)—⟨cyclohexyl⟩—;

R⁶N=C(NHR⁶ᵃ)—N(R⁶ᵃ)—⟨phenyl⟩—; and/or $R^{6b}$, $R^{6e}$, $R^7$, and $R^{7a}$ are H; and/or
$R^{6a}$ is selected from H or $C_1$–$C_4$ alkyl; and/or
Alternatively, $R^{6e}$ and $R^7$ can be taken together with the nitrogen and carbon atom to which they are attached to form a 5–7 membered nitrogen heterocycle, said heterocycle optionally including one additional N, O or S atom.

U is selected from:
—CH₂—CH₂—CH₂—,
—X—CH₂—CH₂—,
—CH₂—X—CH₂—,
—CH₂—CH₂—X—,
—CH₂—CH=CH—,
—CH=CH—CH₂—,
—CH₂—C≡C—,
—C≡C—CH₂—,
—CH=CH—,
—C≡C—,
—CH₂—CH₂—,
—X—CH₂—,
—CH₂—X—,
—CH₂—; and/or X is selected from: O, S, S(=O), SO₂, N(R¹²); with the proviso that when R¹ is R⁶N=C(NHR⁶ᵃ)—N⟨piperazine⟩N— then X is not S or S(=O); with the proviso that when R¹ is

R⁶N=C(NHR⁶ᵃ)—N(R⁶ᵃ)—⟨cyclohexyl⟩— or

R⁶N=C(NHR⁶ᵃ)—N(R⁶ᵃ)—⟨phenyl⟩— then U is not —CH₂—CH₂—CH₂—, —X—CH₂—CH₂—, —CH₂—X—CH₂—, —CH₂—CH₂—X—, —CH₂—CH=CH—, —CH=CH—CH₂—, —CH₂—C≡C—, or —C≡C—CH₂—; and/or $R^{6c}$ is selected from H or $C_1$–$C_4$ alkyl; and/or V is selected from:

—⟨phenyl⟩—Y— substituted with 0–2 $R^5$,

—⟨phenyl⟩—Y— substituted with 0–2 $R^5$, —Q—Y—; and/or

Q is a heterocycle selected from oxazole, isoxazole, oxazoline, isoxazoline, thiazole, isothiazole, thiazoline, isothiazoline, triazole, imidazole, imidazoline, 1,2,4-oxadiazole, 1,2,4-thiadiazole, 1,3,4-oxadiazole, 1,3,4-thiadiazole, pyridine, pyridine N-oxide, thiophene, furan, or pyrrole, said heterocycle being substituted with 0–2 $R^5$, wherein the bonds between Q and Y and between Q and U are at the 1 and 3 positions of Q; and/or $R^5$ is independently selected from: H, halo, cyano, $CO_2R^{5a}$, $OR^{5a}$, $OCH_2CO_2R^{5a}$, $NO_2$, ($C_1$–$C_{10}$ alkyl)carbonyl, —N(R¹²)$R^{5a}$, $C_1$–$C_{10}$ alkyl, $C_2$–$C_6$ alkenyl, $C_4$ to $C_{11}$ cycloalkylmethyl, $C_3$ to $C_{10}$ cycloalkyl, aryl, aryl ($C_1$–$C_6$ alkyl)-, aryl substituted with 0–3 $R^{5c}$; and/or $R^{5a}$ is selected from: H, $C_1$ to $C_{10}$ alkyl, $C_2$ to $C_6$ alkenyl, $C_4$ to $C_{11}$ cycloalkylmethyl, aryl($C_1$–$C_6$ alkyl)-; and/or $R^8$ is selected from:

H;

$C_1$–$C_6$ alkyl substituted with 0–4 $R^{3a}$;

$C_2$–$C_6$ alkenyl substituted with 0–4 $R^{3a}$;

$C_2$–$C_6$ alkynyl substituted with 0–4 $R^{3a}$;

$C_3$–$C_8$ cycloalkyl substituted with 0–4 $R^{3a}$;

aryl substituted with 0–2 $R^{3a}$;

aryl($C_1$–$C_6$ alkyl)-substituted with 0–2 $R^{3a}$;

a heterocyclic ring system selected from pyridinyl, furanyl, thiazolyl, thienyl, pyrrolyl, pyrazolyl, imidazolyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–2 $R^{3a}$;

$C_1$–$C_6$ alkyl substituted with a heterocyclic ring system selected from pyridinyl, furanyl, thiazolyl, thienyl, pyrrolyl, pyrazolyl, imidazolyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–2 $R^{3a}$;

($R^{12}$) ($R^{5a}$)NC(=O)—;

piperidyl-C(=O)—;

O=C(—N⟨piperidine⟩—⟨phenyl⟩)

substituted with 0–2 $R^{3a}$; or

[structure: piperazine with C(=O) on one N and phenyl on other N]

substituted with 0–2 $R^{3a}$; and/or $R^{12}$ and $R^{13}$ are independently selected from: H, $C_1$–$C_{10}$ alkyl, aryl, $C_2$–$C_6$ alkenyl, $C_1$–$C_{11}$ cycloalkylalkyl, aryl ($C_1$–$C_6$ alkyl)-; and/or $R^{3a}$ is selected from H, $C_1$–$C_8$ alkyl, $C_2$–$C_6$ alkenyl, $C_3$–$C_{11}$ cycloalkyl, $C_1$–$C_{11}$ cycloalkylalkyl, aryl, aryl ($C_1$–$C_6$ alkyl)-; and/or $R^9$ is selected from:

H,

—$R^{15}$,

—N($R^{6d}$)C(=O)—O—$R^{15a}$,

—N($R^{6d}$)C(=O)—$R^{15}$,

—N($R^{6d}$)C(=O)—NH—$R^{15}$,

—N($R^{6d}$)NH—C(=O)—O—$R^{15a}$,

—N($R^{6d}$)NH—C(=O)-$R^{15}$,

—N($R^{6d}$)NH—C(=O)—NH—$R^{15}$,

—N($R^{6d}$)S(=O)$_2$—$R^{15}$,

—N($R^{12}$) ($R^{5a}$),

—CH=CH—$R^{15}$, or

—C≡C—$R^{15}$; and/or $R^{6d}$ is selected from: H or $C_1$–$C_4$ alkyl; and/or $R^{15}$ is selected from:

H, $C_1$–$C_8$ alkyl substituted with 0–4 $R^{3a}$, $C_2$–$C_8$ alkenyl substituted with 0–4 $R^{3a}$, $C_3$–$C_8$ cycloalkyl substituted with 0–2 $R^{3a}$, aryl substituted with 0–2 $R^{3a}$, aryl($C_1$–$C_6$ alkyl)-substituted with 0–2 $R^{3a}$, a heterocyclic ring system selected from pyridinyl, furanyl, thiazolyl, thienyl, pyrrolyl, pyrazolyl, imidazolyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–2 $R^{3a}$, $C_1$–$C_6$ alkyl substituted with a heterocyclic ring system selected from pyridinyl, furanyl, thiazolyl, thienyl, pyrrolyl, pyrazolyl, imidazolyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–2 $R^{3a}$; and/or $R^{15a}$ is selected from:

$C_1$–$C_8$ alkyl substituted with 0–4 $R^{3a}$, $C_2$–$C_8$ alkenyl substituted with 0–4 $R^{3a}$, $C_3$–$C_8$ cycloalkyl substituted with 0–2 $R^{3a}$, aryl substituted with 0–2 $R^{3a}$, aryl($C_1$–$C_6$ alkyl)-substituted with 0–2 $R^{3a}$, a heterocyclic ring system selected from pyridinyl, furanyl, thiazolyl, thienyl, pyrrolyl, pyrazolyl, imidazolyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–2 $R^{3a}$, $C_1$–$C_6$ alkyl substituted with a heterocyclic ring system selected from pyridinyl, furanyl, thiazolyl, thienyl, pyrrolyl, pyrazolyl, imidazolyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–2 $R^{3a}$; and/or $R^{10}$ is selected from $CO_2R^{16}$; and/or $R^{16}$ is selected from: H, $C_1$ to $C_{10}$ alkyl, $C_3$ to $C_{11}$ cycloalkyl, aryl, aryl($C_1$ to $C_6$ alkyl)-, $C_3$ to $C_{10}$ alkylcarbonyloxyalkyl, $C_3$ to $C_{10}$ alkoxycarbonyloxyalkyl, $C_2$ to $C_{10}$ alkoxycarbonyl, $C_5$ to $C_{10}$ cycloalkylcarbonyloxyalkyl, $C_5$ to $C_{10}$ cycloalkoxycarbonyloxyalkyl, $C_5$ to $C_{10}$ cycloalkoxycarbonyl, aryloxycarbonyl, aryloxycarbonyloxy ($C_1$ to $C_6$ alkyl)-, arylcarbonyloxy($C_1$ to $C_6$ alkyl)-, $C_5$ to alkoxyalkylcarbonyloxyalkyl, (5-($C_1$–$C_5$ alkyl)-1,3-dioxacyclopenten -2-one-yl)methyl, (5-aryl -1,3-dioxacyclopenten-2-one-yl)methyl, or ($R^{12}$) ($R^{5a}$)N-($C_1$–$C_{10}$ alkyl)-.

More preferred compounds of the present invention are those compounds described above of Formula I, or a pharmaceutically acceptable salt or prodrug form thereof, wherein:

$R^1$ is selected from:

[structure: phenyl with amidine substituent C(=NR⁶)NHR⁶ᵃ]

[structure: piperidine with amidine C(=NR⁶)NHR⁶ᵃ on N]

[structure: piperidine with R⁶—N on one side and (CH₂)q— on other]

[structure: piperazine with amidine C(=NR⁶)NHR⁶ᵃ on one N and N— on other]

[structure: phenyl with N(R⁶ᵃ) linker bearing amidine C(=NR⁶)NHR⁶ᵃ]

and/or $R^{6a}$, $R^{6b}$, $R^7$, and $R^{7a}$ are H; and/or $R^6$ is selected from H or $C_1$–$C_4$ alkyl; and/or U is selected from:

—CH=CH—,

—C≡C—,

—CH$_2$—CH$_2$—,

—X—CH$_2$—,

—CH$_2$—X—; and/or

X is selected from: O, S, S(=O), SO$_2$, N($R^{6c}$); with the proviso that when $R^1$ is

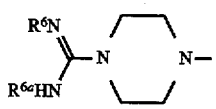

then X is not S, S(=O); and/or $R^{6c}$ is selected from H or $C_1$–$C_4$ alkyl; and/or V is selected from:

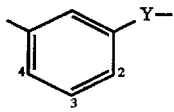

substituted at the 2, 3, or 4 position with 0–1 $R^5$, —Q—Y—; and/or

Y is —C(=O)—; and/or

Q is a heterocycle selected from oxazole, isoxazole, oxazoline, isoxazoline, thiazole, isothiazole, thiazoline, isothiazoline, triazole, imidazole, imidazoline, 1,2,4-oxadiazole, 1,2,4-thiadiazole, 1,3,4-oxadiazole, 1,3,4-thiadiazole, pyridine, pyridine N-oxide, thiophene, furan, or pyrrole, said heterocycle being substituted with 0–2 $R^5$, wherein the bonds between Q and Y and between Q and U are at the 1 and 3 positions of Q; and/or $R^5$ is independently selected from: H, halo, cyano, $C_1$–$C_{10}$ alkyl, $OR^{5a}$, $OCH_2CO_2R^{5a}$, $NO_2$, —$N(R^{12})R^{5a}$, $C_4$ to $C_{11}$ cycloalkylmethyl, aryl, aryl($C_1$–$C_6$ alkyl)-, aryl substituted with 0–3 $R^{5c}$; and/or $R^{5a}$ is selected from: H, $C_1$ to $C_{10}$ alkyl, $C_2$ to $C_6$ alkenyl, $C_4$ to $C_{11}$ cycloalkylmethyl, aryl($C_1$–$C_6$ alkyl)-; and/or $R^{5c}$ is selected from: H, halo, cyano, $C_1$–$C_4$ alkyl, $C_2$–$C_4$ alkenyl, $C_1$–$C_4$ alkoxy, $NO_2$; and/or $R^8$ is selected from:

H, $C_1$–$C_6$ alkyl; and/or $R^9$ is selected from:

—$R^{15}$,

—$N(R^{6d})C(=O)$—O—$R^{15a}$,

—$N(R^{6d})C(=O)$—$R^{15}$,

—$N(R^{6d})S(=O)_2$—$R^{15}$,

—$N(R^{12})$ ($R^{13}$); and/or $R^{6d}$ is H; and/or $R^{12}$ and $R^{13}$ are independently selected from: H, $C_1$–$C_{10}$ alkyl, $C_2$–$C_6$ alkenyl, $C_1$–$C_{11}$ cycloalkylalkyl, aryl($C_1$–$C_6$ alkyl)-; and/or $R^{15}$ is selected from:

H, $C_1$–$C_8$ alkyl, $C_3$–$C_8$ cycloalkyl, aryl substituted with 0–2 $R^{3a}$, aryl($C_1$–$C_6$ alkyl)-substituted with 0–2 $R^{3a}$, a heterocyclic ring system selected from pyridinyl, furanyl, thiazolyl, thienyl, pyrrolyl, pyrazolyl, imidazolyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–2 $R^{3a}$, $C_1$–$C_6$ alkyl substituted with a heterocyclic ring system selected from pyridinyl, furanyl, thiazolyl, thienyl, pyrrolyl, pyrazolyl, imidazolyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–2 $R^{3a}$; and/or $R^{15a}$ is selected from:

$C_1$–$C_8$ alkyl substituted with 0–4 $R^{3a}$, $C_3$–$C_8$ Cycloalkyl substituted with 0–2 $R^{3a}$, aryl substituted with 0–2 $R^{3a}$, aryl($C_1$–$C_6$ alkyl)-substituted with 0–2 $R^{3a}$, a heterocyclic ring system selected from pyridinyl, furanyl, thiazolyl, thienyl, pyrrolyl, pyrazolyl, imidazolyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–2 $R^{3a}$, $C_1$–$C_6$ alkyl substituted with a heterocyclic ring system selected from pyridinyl, furanyl, thiazolyl, thienyl, pyrrolyl, pyrazolyl, imidazolyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–2 $R^{3a}$; and/or $R^{10}$ is selected from $CO_2R^{16}$; and/or $R^{16}$ is selected from:

H;

$C_1$ to $C_{10}$ alkyl;

methylcarbonyloxymethyl-;

ethylcarbonyloxymethyl-;

t-butylcarbonyloxymethyl-;

cyclohexylcarbonyloxymethyl-;

1-(methylcarbonyloxy)ethyl-;

1-(ethylcarbonyloxy)ethyl-;

1-(t-butylcarbonyloxy)ethyl-;

1-(cyclohexylcarbonyloxy) ethyl-;

i-propyloxycarbonyloxymethyl-;

cyclohexylcarbonyloxymethyl-;

t-butyloxycarbonyloxymethyl-;

1-(i-propyloxycarbonyloxy)ethyl-;

1-(cyclohexyloxycarbonyloxy)ethyl-;

1-(t-butyloxycarbonyloxy)ethyl-;

dimethylaminoethyl-;

diethylaminoethyl-;

(1,3-dioxa-5-methyl-cyclopenten-2-one-4-yl)methyl-;

(5-(t-butyl)-1,3-dioxa-cyclopenten-2-one-4-yl)methyl-;

(1,3-dioxa-5-phenyl-cyclopenten-2-one-4-yl)methyl-;

1-(2-(2-methoxypropyl)carbonyloxy) ethyl

Also preferred compounds of the present invention are those compounds of Formula I described above, or a pharmaceutically acceptable salt or prodrug form thereof, wherein:

$R^1$ is

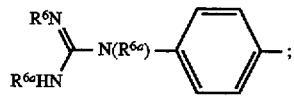

and/or $R^6$, $R^{6a}$, $R^{6b}$, $R^7$, and $R^{7a}$ are H; and/or
U is selected from:
—O—CH$_2$—,
—CH$_2$—O—; and/or
V is:

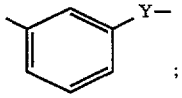

Y is —C(=O)—;
$R^8$ is selected from: H or $C_1$-$C_4$ alkyl;
$R^9$ is selected from: —NHSO$_2$-phenyl, —NH-Tosyl, —NHSO$_2$($C_1$-$C_6$ alkyl)-, —NH—Cbz, —NHC(=O) ($C_1$-$C_6$ alkoxy), —NHC(=O) ($C_1$-$C_6$ alkyl), —NHC(=O)-aryl, —NHC(=O)O-($C_1$-$C_6$ alkyl)aryl, —NH(C=O)-($C_1$-$C_6$ alkyl)aryl, —NHC(=O)-3-pyridyl;
$R^{10}$ is selected from CO$_2$R$^{16}$; and/or
$R^{16}$ is selected from: H, $C_1$ to $C_6$ alkyl.

Specifically preferred compounds of the present invention are compounds of Formula I of Formula II:

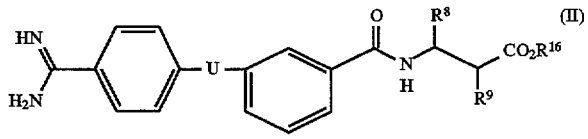

or a pharmaceutically acceptable salt or prodrug form thereof, selected from:
the compound wherein U is OCH$_2$, $R^8$ is CH$_3$, $R^9$ is H, and $R^{16}$ is H;
the compound wherein U is OCH$_2$, $R^8$ is H, $R^9$ is —NH—Cbz, and $R^{16}$ is H;
the compound wherein U is OCH$_2$, $R^8$ is H, $R^9$ is —NH—Cbz, and $R^{16}$ is CH$_3$;
the compound wherein U is OCH$_2$, $R^8$ is H, $R^9$ is —NH—Cbz, and $R^{16}$ is CH$_2$CH$_3$;
the compound wherein U is CH$_2$O, $R^8$ is CH$_3$, $R^9$ is H, and $R^{16}$ is H;
the compound wherein U is CH$_2$O, $R^8$ is CF$_3$, $R^9$ is H, and $R^{16}$ is H;
the compound wherein U is OCH$_2$, $R^8$ is H, $R^9$ is H, and $R^{16}$ is H;
the compound wherein U is OCH$_2$, $R^8$ is H, $R^9$ is —NH-Tosyl, and $R^{16}$ is H;
the compound wherein U is OCH$_2$, $R^8$ is H, $R^9$ is —NH-Tosyl, and $R^{16}$ is CH$_3$;
the compound wherein U is OCH$_2$, $R^8$ is H, $R^9$ is —NH—SO$_2$(CH$_2$)$_3$CH$_3$, and $R^{16}$ is H;
the compound wherein U is OCH$_2$, $R^8$ is H, $R^9$ is —NH—SO$_2$(CH$_2$)$_3$CH$_3$, and $R^{16}$ is CH$_3$;
the compound wherein U is OCH$_2$, $R^8$ is H, $R^9$ is —NH—C(=O)O—C(CH$_3$)$_3$, and $R^{16}$ is H;
the compound wherein U is OCH$_2$, $R^8$ is H, $R^9$ is —NH—C(=O)O—C(CH$_3$)$_3$, and $R^{16}$ is CH$_3$;
the compound wherein U is OCH$_2$, $R^8$ is H, $R^9$ is —NH—C(=O)—(CH$_2$)$_3$CH$_3$, and $R^{16}$ is
the compound wherein U is OCH$_2$, $R^8$ is H, $R^9$ is —NH—C(=O)—(CH$_2$)$_3$CH$_3$, and $R^{16}$ is CH$_3$;
the compound wherein U is OCH$_2$, $R^8$ is H, $R^9$ is —NH—C(=O)—O(CH$_2$)$_3$CH$_3$, and $R^{16}$ is H;
the compound wherein U is OCH$_2$, $R^8$ is H, $R^9$ is —NH—C(=O)—O(CH$_2$)$_3$CH$_3$, and $R^{16}$ is CH$_3$;
the compound wherein U is OCH$_2$, $R^8$ is H, $R^9$ is —NH—C(=O)—(CH$_2$)$_2$CH$_3$, and $R^{16}$ is H;
the compound wherein U is OCH$_2$, $R^8$ is H, $R^9$ is —NH—C(=O)—(CH$_2$)$_2$CH$_3$, and $R^{16}$ is CH$_3$;
the compound wherein U is OCH$_2$, $R^8$ is H, $R^9$ is —NH—C(=O)—2-pyridyl, and $R^{16}$ is
the compound wherein U is OCH$_2$, $R^8$ is H, $R^9$ is —NH—C(=O)—2-pyridyl, and $R^{16}$ is CH$_3$;
the compound wherein U is OCH$_2$, $R^8$ is H, $R^9$ is —NH—C(=O)—3-pyridyl, and $R^{16}$ is H;
the compound wherein U is OCH$_2$, $R^8$ is H, $R^9$ is —NH—C(=O)—3-pyridyl, and $R^{16}$ is CH$_3$;
the compound wherein U is OCH$_2$, $R^8$ is H, $R^9$ is —NH—C(=O)—4-pyridyl, and $R^{16}$ is H;
the compound wherein U is OCH$_2$, $R^8$ is H, $R^9$ is —NH—C(=O)—4-pyridyl, and $R^{16}$ is CH$_3$;
the compound wherein U is OCH$_2$, $R^8$ is H, $R^9$ is —NH—C(=O)—CH$_2$-2-pyridyl, and $R^{16}$ is H;
the compound wherein U is OCH$_2$, $R^8$ is H, $R^9$ is —NH—C(=O)—CH$_2$-2-pyridyl, and $R^{16}$ is CH$_3$;
the compound wherein U is OCH$_2$, $R^8$ is H, $R^9$ is —NH—C(=O)—CH$_2$-3-pyridyl, and $R^{16}$ is H;
the compound wherein U is OCH$_2$, $R^8$ is H, $R^9$ is —NH—C(=O)—CH$_2$-3-pyridyl, and $R^{16}$ is CH$_3$;
the compound wherein U is OCH$_2$, $R^8$ is H, $R^9$ is —NH—C(=O)—CH$_2$-4-pyridyl, and $R^{16}$ is H;
the compound wherein U is OCH$_2$, $R^8$ is H, $R^9$ is —NH—C(=O)—CH$_2$-4-pyridyl, and $R^{16}$ is CH$_3$;
the compound wherein U is OCH$_2$, $R^8$ is H, $R^9$ is —NH—C(=O)—(CH$_2$)2-phenyl, and $R^{16}$ is H;
the compound wherein U is OCH$_2$, $R^8$ is H, $R^9$ is —NH—C(=O)—(CH$_2$)2-phenyl, and $R^{16}$ is CH$_3$;
the compound wherein U is OCH$_2$, $R^8$ is H, $R^9$ is —NH$_2$, and $R^{16}$ is H;
the compound wherein U is OCH$_2$, $R^8$ is H, $R^9$ is —NH$_2$, and $R^{16}$ is CH$_3$.

Also preferred compounds of the present invention are those compounds of Formula I described above, or a pharmaceutically acceptable salt or prodrug form thereof, wherein:
$R^1$ is

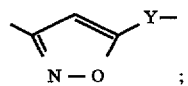

and/or
$R^6$, $R^{6a}$, $R^{6b}$, $R^7$, and $R^{7a}$ are H; and/or
U is selected from:
—O—CH$_2$—,
—CH$_2$—O—; and/or
V is:

N—O

Y is —C(=O)—;
$R^8$ is selected from: H or $C_1$-$C_4$ alkyl;
$R^9$ is selected from: —NHSO$_2$-phenyl, —NH-Tosyl, —NHSO$_2$($C_1$-$C_6$ alkyl)-, —NH—Cbz, —NHC(=O) ($C_1$-$C_6$ alkoxy), —NHC(=O) ($C_1$-$C_6$ alkyl), —NHC(=O)-aryl, —NHC(=O)O—($C_1$-$C_6$ alkyl)aryl, —NH(C=O)—($C_1$-$C_6$ alkyl)aryl, —NHC(=O)-3-pyridyl;
$R^{10}$ is selected from CO$_2$R$^{16}$; and/or
$R^{16}$ is selected from: H, $C_1$ to $C_6$ alkyl.

Also specifically preferred compounds of the present invention are compounds of Formula I of Formula III:

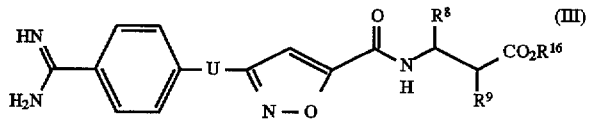

or a pharmaceutically acceptable salt or prodrug form thereof, selected from:

the compound wherein U is $OCH_2$, $R^8$ is $CH_3$, $R^9$ is H, and $R^{16}$ is H;

the compound wherein U is $OCH_2$, $R^8$ is H, $R^9$ is —NH—Cbz, and $R^{16}$ is H;

the compound wherein U is $OCH_2$, $R^8$ is H, $R^9$ is —NH—Cbz, and $R^{16}$ is $CH_3$;

the compound wherein U is $OCH_2$, $R^8$ is H, $R^9$ is —NH—Cbz, and $R^{16}$ is $CH_2CH_3$;

the compound wherein U is $CH_2O$, $R^8$ is $CH_3$, $R^9$ is H, and $R^{16}$ is H;

the compound wherein U is $CH_2O$, $R^8$ is $CF_3$, $R^9$ is H, and $R^{16}$ is H;

the compound wherein U is $OCH_2$, $R^8$ is H, $R^9$ is H, and $R^{16}$ is H;

the compound wherein U is $OCH_2$, $R^8$ is H, $R^9$ is —NH-Tosyl, and $R^{16}$ is H;

the compound wherein U is $OCH_2$, $R^8$ is H, $R^9$ is —NH-Tosyl, and $R^{16}$ is $CH_3$;

the compound wherein U is $OCH_2$, $R^8$ is H, $R^9$ is —NH—$SO_2(CH_2)_3CH_3$, and $R^{16}$ is the compound wherein U is $OCH_2$, $R^8$ is H, $R^9$ is —NH—$SO_2(CH_2)_3CH_3$, and $R^{16}$ is $CH_3$;

the compound wherein U is $OCH_2$, $R^8$ is H, $R^9$ is —NH—C(=O)O—C($CH_3$)$_3$, and $R^{16}$ is H;

the compound wherein U is $OCH_2$, $R^8$ is H, $R^9$ is —NH—C(=O)O—C($CH_3$)$_3$, and $R^{16}$ is $CH_3$;

the compound wherein U is $OCH_2$, $R^8$ is H, $R^9$ is —NH—C(=O)—($CH_2$)$_3$$CH_3$, and $R^{16}$ is H;

the compound wherein U is $OCH_2$, $R^8$ is H, $R^9$ is —NH—C(=O)—($CH_2$)$_3$$CH_3$, and $R^{16}$ is $CH_3$;

the compound wherein U is $OCH_2$, $R^8$ is H, $R^9$ is —NH—C(=O)—O($CH_2$)$_3$$CH_3$, and $R^{16}$ is H;

the compound wherein U is $OCH_2$, $R^8$ is H, $R^9$ is —NH—C(=O)—O($CH_2$)$_3$$CH_3$, and $R^{16}$ is $CH_3$;

the compound wherein U is $OCH_2$, $R^8$ is H, $R^9$ is —NH—C(=O)—($CH_2$)2$CH_3$, and $R^{16}$ is H;

the compound wherein U is $OCH_2$, $R^8$ is H, $R^9$ is —NH—C(=O)—($CH_2$)2$CH_3$, and $R^{16}$ is $CH_3$;

the compound wherein U is $OCH_2$, $R^8$ is H, $R^9$ is —NH—C(=O)—3-pyridyl, and $R^{16}$ is H;

the compound wherein U is $OCH_2$, $R^8$ is H, $R^9$ is —NH—C(=O)—3-pyridyl, and $R^{16}$ is $CH_3$;

the compound wherein U is $OCH_2$, $R^8$ is H, $R^9$ is —NH—C(=O)—($CH_2$)2-phenyl, and $R^{16}$ is H;

the compound wherein U is $OCH_2$, $R^8$ is H, $R^9$ is —NH—C(=O)—($CH_2$)2-phenyl, and $R^{16}$ is $CH_3$;

the compound wherein U is $OCH_2$, $R^8$ is H, $R^9$ is —$NH_2$, and $R^{16}$ is H;

the compound wherein U is $OCH_2$, $R^8$ is H, $R^9$ is —$NH_2$, and $R^{16}$ is $CH_3$.

In the present invention it has been discovered that the compounds of Formula I above are useful as inhibitors of glycoprotein IIb/IIIa (GPIIb/IIIa). The compounds of the present invention inhibit the activation and aggregation of platelets induced by all known endogenous platelet agonists.

The present invention also provides pharmaceutical compositions comprising a compound of Formula I and a pharmaceutically acceptable carrier.

Also included in the present invention are pharmaceutical kits comprising one or more containers containing pharmaceutical dosage units comprising a compound of Formula I, for the treatment of thromboembolic disorders.

The compounds of Formula I of the present invention are useful for the treatment (including prevention) of thromboembolic disorders. The term thromboembolic disorders as used herein includes conditions involving platelet activation and aggregation, such as arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolisms, pulmonary embolisms, or diabetes, comprising administering to a mammal in need of such treatment a therapeutically effective amount of a compound of Formula I described above.

The compounds of the present invention are useful for inhibiting the binding of fibrinogen to blood platelets, inhibiting aggregation of blood platelets, treating thrombus formation or embolus formation, or preventing thrombus or embolus formation in a mammal. The compounds of the invention may be used as a medicament for blocking fibrinogen from acting at its receptor site in a mammal.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption, and where the aggregated platelets may form thrombi and thromboemboli. The compounds of the present invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the circuit. Platelets released from artificial surfaces show impaired homeostatic function. Compounds of the invention my be administered to prevent adhesion.

Other applications of these compounds include prevention of platelet thrombosis, thromboembolism, and reocclusion during and after thrombolytic therapy and prevention of platelet thrombosis, thromboembolism and reocclusion after angioplasty of coronary and other arteries and after coronary artery bypass procedures., The compounds of the present invention may also be used to prevent myocardial infarction. The compounds of the present invention are useful as thrombolytics for the treatment of thromboembolic disorders.

The compounds of the present invention can also be administered in combination with one or more additional therapeutic agents select from: anti-coagulant or coagulation inhibitory agents, such as heparin or warfarin; anti-platelet or platelet inhibitory agents, such as aspirin, piroxicam, or ticlopidine; thrombin inhibitors such as boropeptides, hirudin or argatroban; or thrombolytic or fibrinolytic agents, such as plasminogen activators, anistreplase, urokinase, or streptokinase.

The compounds of Formula I of the present invention can be administered in combination with one or more of the foregoing additional therapeutic agents, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent. Such combination therapies may be employed to achieve synergistic or additive therapeutic effects for the treatment of thromboembolic disorders.

By "therapeutically effective amount" it is meant an amount of a compound of Formula I that when administered alone or in combination with an additional therapeutic agent to a cell or mammal is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term anti-coagulant agents (or coagulation inhibitory agents), as used herein, denotes agents that inhibit blood coagulation. Such agents include warfarin (available as Coumadin™) and heparin.

The term anti-platelet agents (or platelet inhibitory agents), as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam. Piroxicam is commercially available from Pfizer Inc. (New York, N.Y.), as Feldane™. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include thromboxane-A2-receptor antagonists and thromboxane-A2-synthetase inhibitors, as well as pharmaceutically acceptable salts or prodrugs thereof.

The phrase thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boropeptides, hirudin and argatroban, including pharmaceutically acceptable salts and prodrugs thereof. Preferably the thrombin inhibitors are boropeptides. By boropeptides, it is meant, N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boropeptide thrombin inhibitors include those disclosed in PCT Application Publication Number 92/07869 and European Patent Application Publication Number 471 651 A2, the disclosures of which are hereby incorporated herein by reference, in their entirety.

The phrase thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 028,489, the disclosures of which are hereby incorporated herein by reference herein, in their entirety. Anistreplase is commercially available as Eminase™. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

GPIIb/IIIa is known to be overexpressed in metastatic tumor cells. The compounds or combination products of the present invention my also be useful for the treatment, including prevention, of metastatic cancer.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention may contain asymmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example but not limited to, $R^5$, $R^{5a}$, and $R^6$, p, etc.) occurs more than one time in any constituent or in any formula, its definition on each occurrence is independent of its definition at every other occurrence. Thus, for example, if a group is shown to be substituted with 0–2 $R^5$, then said group may optionally be substituted with up to two $R^5$ and $R^5$ at each occurrence is selected independently from the defined list of possible $R^5$. Also, by way of example, for the group —N($R^{6a}$)$_2$, each of the two $R^{6a}$ substituents on N is independently selected from the defined list of possible $R^{6a}$. Similarly, by way of example, for the group —C($R^7$)$_2$—, each of the two $R^7$ substituents on C is independently selected from the defined list of possible $R^7$.

When a bond to a substituent is shown to cross the bond connecting two atoms in a ring, then such substituent may be bonded to any atom on the ring.

When a substituent is listed without indicating the atom via which such substituent is bonded to the rest of the compound of Formula I, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formula I via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example —$C_vR_w$ where v=i to 3 and w=1 to (2v+1)); "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, cycloheptyl, cyclooctyl, and adamantyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The terms "-(alkyl)-", "-(alkyenyl)-", "-(phenyl)-", and the like, refer to alkyl, alkenyl, and phenyl groups, respectively, which are connected by two bonds to the rest of the structure of Formula I. Such groups may alternatively and equivalently be denoted as "alkylene", "alkenylene", "phenylene", and the like, respectively.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; the term "arylalkyl" represents an aryl group attached through an alkyl bridge.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heteroaryl" or "heterocyclic" is intended to mean a stable 5- to 7- membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, isothiazolyl, thiazolinyl, isothiazolinyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H, 6H-1,5,2-dithiazinyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolyl, oxazoline, isoxazoline, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

As used herein, "pharmaceutically acceptable salts" refer to derivatives of the disclosed compounds wherein the parent compound of Formula I is modified by making acid or base salts of the compound of Formula I. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to Formula I in vivo when such prodrug is administered to a mammalian subject. Prodrugs of the compounds of Formula I are prepared by modifying functional groups present in the compounds in such a way that the modifications are cleaved, either in routine manipulation or in vivo, to the parent compounds. Prodrugs include compounds of Formula I wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula I, and the like. Examples of representative carboxyl and amino prodrugs are included under the definition of $R^6$, $R^{6a}$, and $R^{16}$.

As used herein, the term "amine protecting group" means any group known in the art of organic synthesis for the protection of amine groups. Such amine protecting groups include those listed in Greene, "Protective Groups in Organic Synthesis" John Wiley & Sons, New York (1981) and "The Peptides: Analysis, Sythesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl (Tosyl); 2) aromatic carbamate types such as benzyloxycarbonyl (Cbz; carbobenyloxy) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. Also included in the term "amine protecting group" are acyl groups such as azidobenzoyl, p-benzoylbenzoyl, o-benzylbenzoyl, p-acetylbenzoyl, dansyl, glycyl-p-benzoylbenzoyl, phenylbenzoyl, m-benzoylbenzoyl, benzoylbenzoyl.

The pharmaceutically acceptable salts of the compounds of Formula I include the conventional non-toxic salts or the quaternary ammonium salts of the compounds of Formula I formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The disclosures of all of the references cited herein are hereby incorporated herein by reference in their entirety.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference. All the temperatures are reported herein in degrees Celsius.

The following abbreviations are used herein:

| | |
|---|---|
| β-Ala | 3-aminopropionic acid |
| Boc | tert-butyloxycarbonyl |
| Boc$_2$O | di-tert-butyl dicarbonate |
| BSTFA | N,O-bis(trimethylsilyl)trifluoromethyl-acetamide |
| Cbz | benzyloxycarbonyl |
| DCC | 1,3-dicyclohexylcarbodiimide |
| DEAD | diethyl azodicarboxylate |
| DEC | 1-(3-dimethylaminopropyl)-3-ethylcarbodiimide hydrochloride |
| DIEA | diisopropylethylamine |
| DCHA | dicyclohexylamine |
| DCM | dichloromethane |
| DMAP | 4-dimethylaminopyridine |
| DMF | N,N-dimethylformamide |
| EtOAc | ethyl acetate |
| EtOH | ethyl alcohol |
| HOBt | 1-hydroxybenzotriazole |
| IBCF | iso-butyl chloroformate |
| LAH | lithium aluminum hydride |
| NCS | N-chlorosuccinimide |
| NMM | N-methylmorpholine |
| PPh$_3$ | triphenylphosphine |
| pyr | pyridine |
| TBTU | 2-(1H-Benzotriazol-1-yl)-1,1,3,3-tetramethyluronium tetrafluoroborate |
| TFA | trifluoroacetic acid |
| THF | tetrahydrofuran |

The compounds included in this invention can be prepared by methods familiar to one skilled in the art of organic synthesis. For instance, the syntheses of the more preferred classes of compounds are described in the following Schemes.

When the compound of interest contains an aryl amidine connected to the central phenyl ring (group V in Formula I) by an O—CH$_2$ linking group the structure can be prepared as described in Scheme I. Similar methods can be used to prepare the corresponding aminomethyl compounds (Scheme I). The aminomethyl group can be N-alkylated by treatment of the primary amine with a ketone plus NaBH$_3$CN (*Synthesis* 135 (1975); Organic Preparations and Procedures, International 17, 317 (1983)).

Scheme I

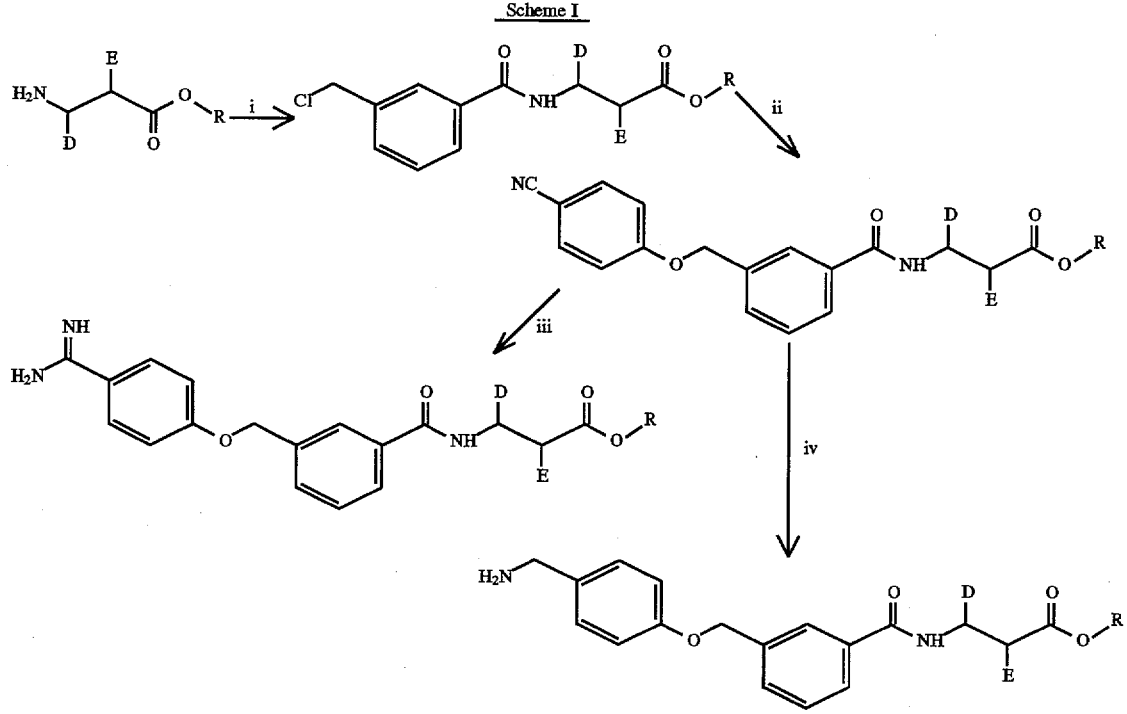

Reagents: i) 3-(chloromethyl)benzoyl chloride, triethylamine, methylene chloride; ii) 4-cyanophenol, $K_2CO_2CO_3$ or NAH; iii) 1) HCl/methanol, 2) ammonia in methanol, or 1) $H_2S$/triethylamine, 2 MeI, 3) $NH_3$; iv) HCl, $H_2Pd/C$ or $H_2/PtO_2$ In Scheme I, the groups R, E, and D correspond to $R^{16}$, $R^9$, and $R^8$, respectively, in the compounds of Formula I described above.

Alkyl substituents on the central phenyl ring (V in Formula I) can be introduced at the beginning of the synthetic procedure as described in Scheme II.

Scheme II

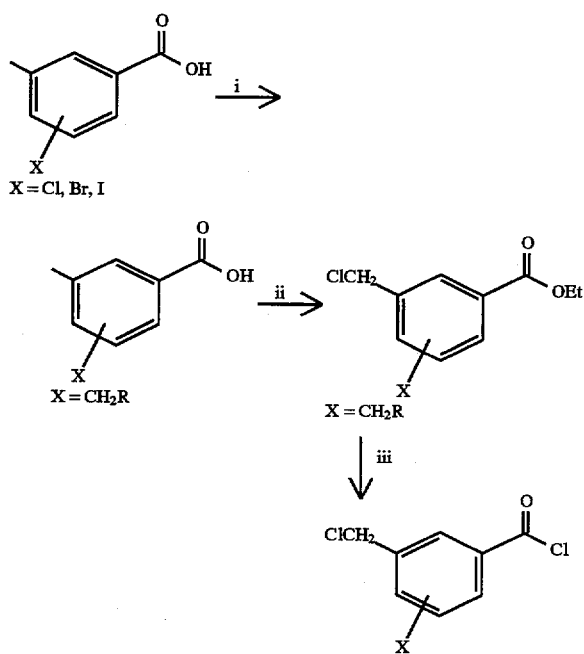

Reagents:
i) 1) n-butyl lithium, 2) RCH(=O), 3) HCl, $H_2$ Pd/C or Raney Nickle;
ii) 1) HCl/EtOH, 2) $SO_2Cl_2$;
iii) 1) LiOTMS, 2) $SOCl_2$ or $PCl_5$.

Substituent X in Scheme II corresponds to $R^5$ in the compounds of Formula I described above.

Similarly, hydroxy or alkoxy substituents can be introduced by reacting the lithiated species generated in the first reaction of Scheme II with bis(trimethylsilyl) peroxide to give the silyl ether (Taddei and Ricci, *Synthesis* 633–635 (1986). The silyl ether can be converted to the phenolic compound by treatment with TBAF or with HCl. The carboxylate is then protected via the ethyl ester (HCl/ethanol), and the phenol converted to an alkyl aryl ether by treatment with an alkyl halide and a base such as $K_2CO_3$. Benzylic chlorination, saponification, and conversion to the acid chloride are then accomplished as in the final steps of Scheme II.

Aryl substituted derivatives of 3-(chloromethyl)benzoyl chloride can be prepared by Scheme III in which the aryl-aryl bond is formed using the Suzuki coupling procedure (Miyaura, Yanagi, Suzuki, *Synth. Commun.* 11, 513 (1981); Sharp, Snieckus, *Tetrahedron Lett.* 26, 5997 (1985)).

Scheme III

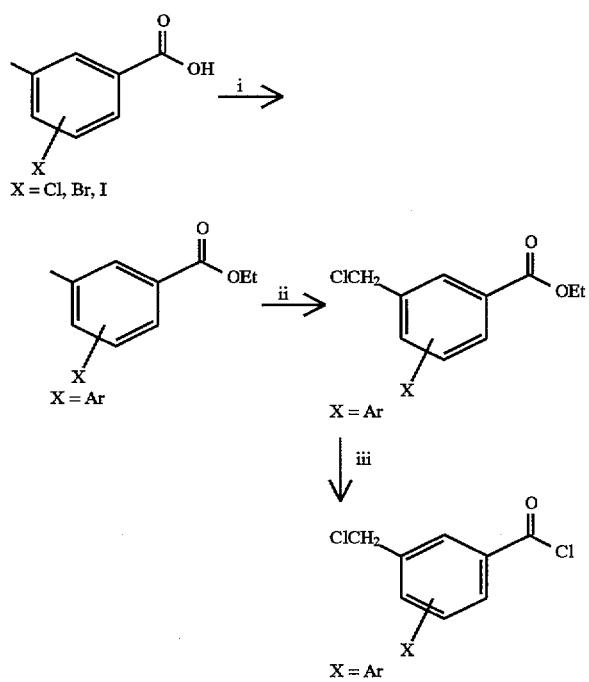

Reagents:
i) 1) HCl/EtOH, 2) Ar—B(OH)$_2$, Pd(PPh$_3$)$_4$;
ii) SO$_2$Cl$_2$;
iii) 1) LiOTMS, 2) SOCl$_2$ or PCl$_5$.

Substituent X in Scheme III corresponds to R$^5$ in the compounds of Formula I described above.

Methods for the synthesis of beta amino acids (H$_2$N—CHR$^8$—CH$_2$—COOH) (used in Scheme I) have been described previously in European Patent Application Publication Number 542,708, and PCT Patent Applications WO 93/07867, WO 93/12074, and WO 93/16038, the disclosures of which are hereby incorporated by reference.

General methods for protection of the carboxylate group have been discussed in T. H. Greene, Protective Groups in Organic Synthesis (Wiley-Interscience, 1980), the disclosure of which is hereby incorporated by reference. Carboxylate protecting groups useful for peptide synthesis have been reviewed (R. W. Roeske, in The Peptides, Vol 3; Protection of functional groups in peptide synthesis, 1981, pp 1–99; Academic Press).

The synthesis of N2-substituted 2,3-diamino propionic derivatives can be carried out via Hoffman rearrangement of a wide variety of asparagine derivatives as described in Synthesis, 266–267 (1981), the disclosure of which is hereby incorporated by reference.

Homo beta amino acids (H$_2$N—CH$_2$—CHR$^9$—COOH) can be synthesized from a variety of carboxylic acids as described in Scheme IV. α-Halogenation of a carboxylic acid (Harwood, Chem. Rev. 62, 99–154 (1962)) followed by displacement of the halogen with KCN gives a nitrile, which upon reduction (as described in Tett. Lett., 4393 (1975); Modern Synthetic Reactions, H. O. House (1972); or Harting et al., J. Am. Chem. Soc., 50: 3370 (1928)) provides the desired 3-amino-propionic acid derivative.

Scheme IV

R$^9$\\_/C(=O)—OH $\xrightarrow{\text{1) Br}_2\text{, PBr}_3 \atop \text{2) HCl/ROH} \atop \text{3) KCN}}$ NC—CHR$^9$—C(=O)OR$^{16}$ $\xrightarrow{\text{H}_2\text{PtO}_2 \atop \text{HCl}}$ H$_2$N—CH$_2$—CHR$^9$—C(=O)OR$^{16}$ Alternatively, homo beta amino acids in which R$^9$ is an alkyl group can be prepared from esters of 2-(cyano)acetic acid as described in Scheme V by alkylation (Kauer, Erickson-Viitanen, Wolfe, DeGrado, J. Biol. Chem. 261, 10695–10700 (1986)) followed by reduction of the nitrile.

Scheme V

NC—CH$_2$—C(=O)OR$^{16}$ $\xrightarrow{\text{1) LiN(SiMe}_3\text{)}_2 \atop \text{2) R}^9\text{—X} \atop \text{(X = Cl, Br, I)}}$ NC—CHR$^9$—C(=O)OR$^{16}$ $\xrightarrow{\text{HCl, H}_2, \atop \text{PtO}_2}$ H$_2$N—CH$_2$—CHR$^9$—C(=O)OR$^{16}$ In Scheme I the 3-(chloromethyl)benzoic acid group is coupled to the 3-amino-propionic acid derivative using the acid chloride methods. Other methods for the coupling of carboxylates to amino acid derivatives have been reviewed previously (E. Gross and J. Meienhofer, eds, The Peptides, Vol. 1, Major methods of peptide bond formation, 1979, Academic Press).

When the compound of interest contains an aryl amidine connected to the central phenyl ring (V in Formula I) by an CH$_2$—O linking group the structure can be prepared as described in Scheme VI. Similar methods can be used to prepare the corresponding aminomethyl compounds (Scheme VI). The aminomethyl group can be N-alkylated by treatment of the primary amine with a ketone plus NaBH$_3$CN (Synthesis 135 (1975); Organic Preparations and Procedures, International 17: 317 (1983)).

Scheme VI

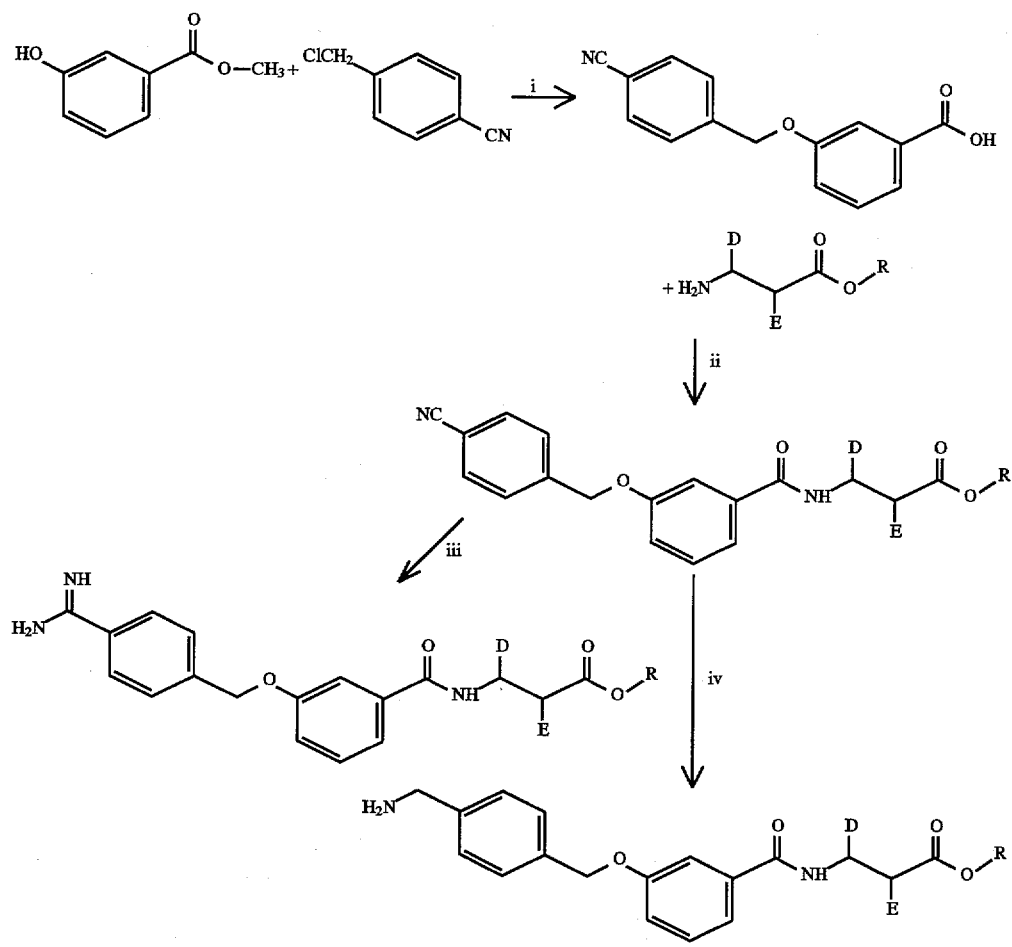

Reagents: i) 1) K₂CO₃ or NaH 2) LiOH or LiOTMS; ii) DCC or TBTU/Et₃N; iii) 1) HCl/methanol, 2) ammonia in methanol; or 1) H₂S/triethylamine, 2) MeI, 3) NH₃; iv) HCl, H₂ Pd/C or HCl, H₂/PtO₂

In Scheme VI, the substituents E, R, and D correspond to $R^9$, $R^{16}$, and $R^8$, respectively, in the compounds of Formula I described above.

When the compound of interest contains a piperidine or an N-amidino piperidine connected to the central phenyl ring (V in Formula I) by a $(CH_2)_n$—O linking group the structure can be prepared as described in Scheme VII, in which n=1. Examples in which n is zero or greater than one can be prepared by analogous methods.

Scheme VII

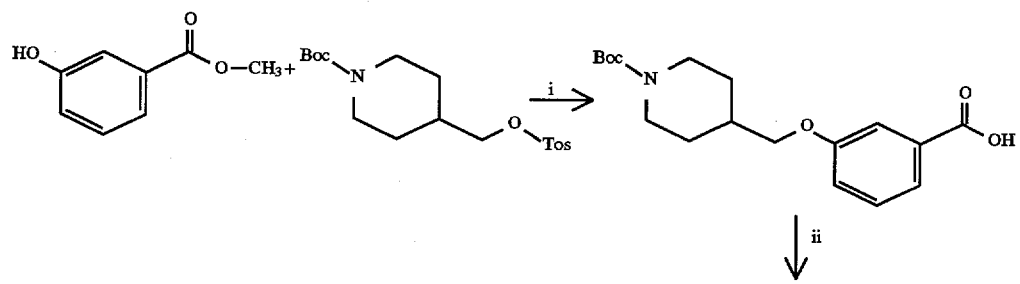

-continued
Scheme VII

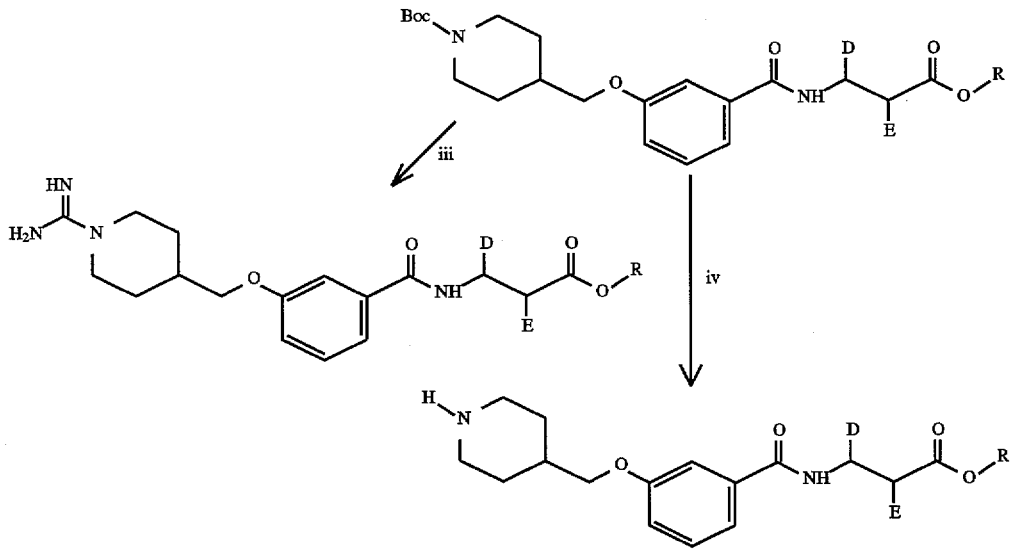

Reagents: i) 1) K₂CO₃ or NaH; 2) LiOH or LiOTMS ii) DCC or TBTU/Et₃N; iii) 1) TFA, 2) H₂N—C(=NH)-SEt/Et₃N or H₂N—C(=NH)—SO₃H/DMAP; iv) TFA In Scheme VII, the substituents E, R, and D correspond to $R^9$, $R^{16}$, and $R^8$, respectively, in the compounds of Formula I described above.

Using the analogous route depicted in Scheme VIIa, compounds with a piperidine or an N-amidino piperidine connected to the central phenyl ring (V in Formula I) by a $(CH_2)_n$—O linking group where $R^{6c}$ and $R^7$ are taken together with the nitrogen and carbon atoms to which they are attached to form a N-heterocycle can be prepared. Methyl p-hydroxybenzoate is alkylated with a Boc-protected piperidinylalkylalcohol. Saponification and TBTU-mediated coupling to 2-piperidinylacetic acid followed by deprotection gives the desired amino acid. Further elaboration of the piperidine to the amidinopiperidine can be carried out, as described above, prior to final hydrolysis of the ester. The substitution of other cyclic aminoester for 2-piperidinylacetic acid provides additional examples of this group of compounds.

Scheme VIIa

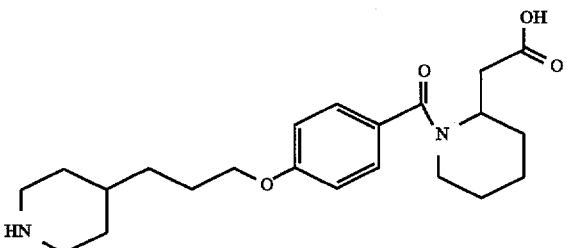

-continued
Scheme VIIa

XR-283

Reagents: a. Boc-amino alcohol, PPh₃, DEAD, THF; b. LiOH, THF/H₂O
c. β-amino ester, Et₃N, TBTU, DMF; d. LiOH, THF/H₂O;
e. 33% TFA/CH₂Cl₂

Piperidines used in Scheme VII can be prepared from hydroxypiperidines as described in Scheme VIII.

Scheme VIII

Reaction conditions: 1) Boc-ON/triethylamine or di-t-butyl-dicarbonate/triethylamine; ii) p-toluenesulfonic anhydride/triethylamine or p-toluenesulfonyl chloride/triethylamine.

When the compound of interest contains a piperidine or a N-amidinopiperidine connected to the central phenyl ring (V in Formula I) by a $(CH_2)_n$—O—$CH_2$ linking group, the structure can be prepared as described in Scheme IX, in which n=0. Examples in which n is one or greater can be prepared by analogous methods.

Scheme IX

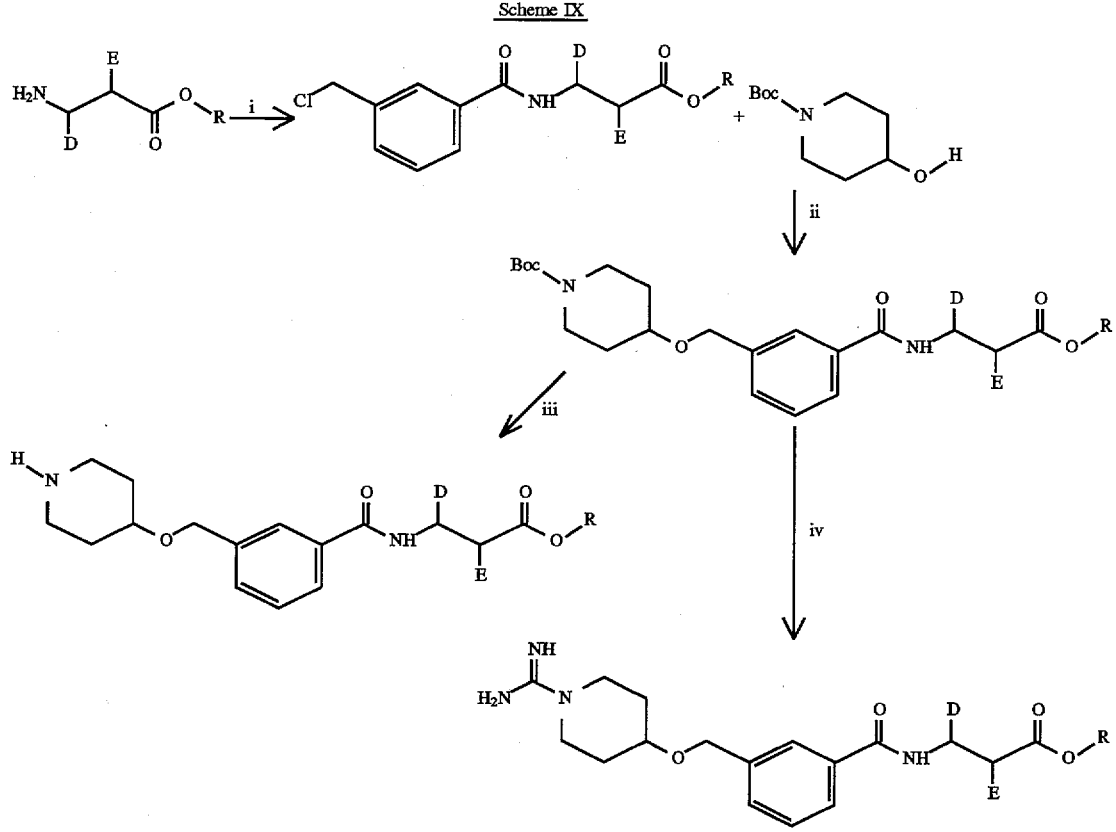

Reaction conditions: 1) 3-(chloromethyl)benzoyl chloride, triethylamine; ii) NaH or KN(SiMe₃)₂; iii) TFA, or 4M HCl/Dioxane; iv) 1) TFA, or 4M HCl/Dioxane, 2) S-ethylthisourea, Et₃N, or H₂N—C(=NH)—SO₃H/DMAP.

In Scheme IX, the substituents E, R, and D correspond to $R^9$, $R^{16}$, and $R^8$, respectively, in the compounds of Formula I as described above.

When the compound of interest contains an amine or a N-amidine-substituted amine connected to the central phenyl ring (V in Formula I) by a $(CH_2)_n$—O linking group, the structure can be prepared as described in Scheme X, in which n=5. Examples in which n is one to eight can be prepared by analogous methods.

Scheme X

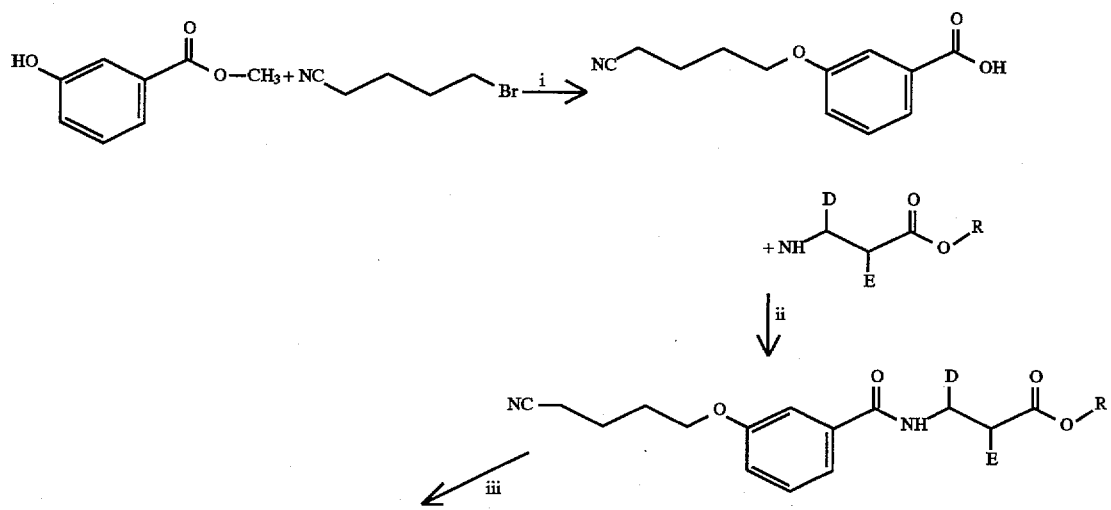

-continued
Scheme X

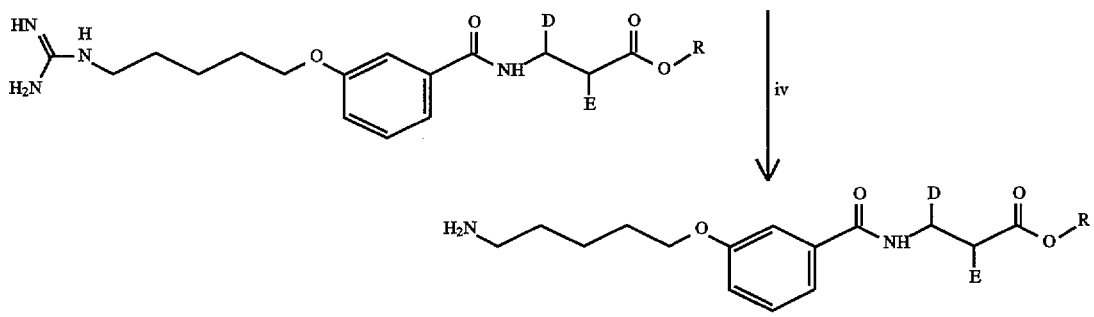

Reaction conditions: i) $K_2CO_3$ or NaH, 1) LiOH or LiOTM; ii) DCC or TBTU/$Et_3N$;
iii) 1) HCl, $H_2$Pd/C or $H_2$/$PtO_2$, 2) $H_2N-C(=NH)SO_3H$/DMAP or $H_2N-C(=NH)-S-Et/Et_3N$;
iv) HCl, $H_2$Pd/C or HCl, $H_2$/$PtO_2$ In Scheme IX, the substituents E, R, and D correspond to $R^9$, $R^{16}$, and $R^8$, respectively, in the compounds of Formula I described above.

Bromonitriles used in the above synthesis are generally commercially available, or can be prepared by treating a dibromide (in excess) with KCN at 50°–100° in DMSO.

When the compound of interest contains an amine or a N-amidine-substituted amine connected to the central phenyl ring (V in Formula I) by a $(CH_2)_n$—O—$CH_2$ linking group, the structure can be prepared as described in Scheme XI, in which n=4. Examples in which n is one to eight can be prepared by analogous methods.

Scheme XI

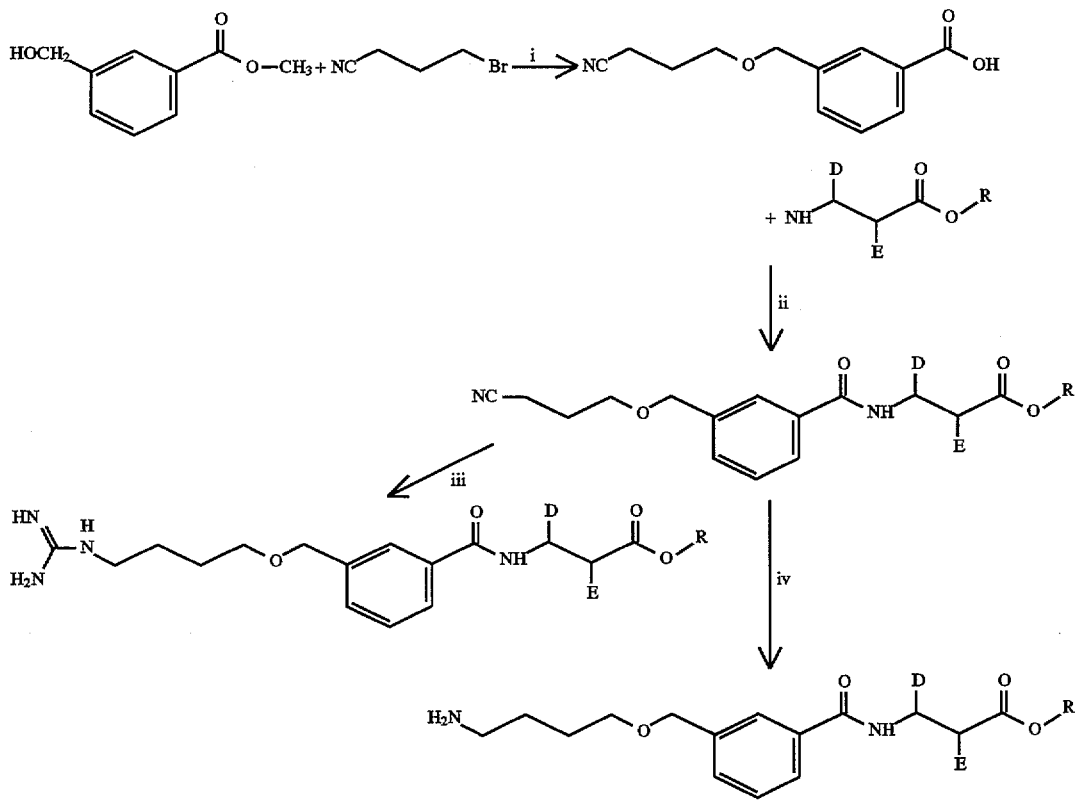

Reaction conditions: i) $KN(SiMe_3)_2$, $KOC(CH_3)_3$ or NaH 2) LiOH or LiOTMS; ii) DCC or TBTU/$Et_3N$; iii) 1) HCl, $H_2$Pd/C or $H_2$/$PtO_2$, 2) $H_2N-C(=NH)SO_3H$/DMAP or $H_2N-C(=NH)-S-Et/Et_3N$; iv) HCl, $H_2$Pd/C or $H_2$/$PtO_2$ In Scheme XI, E, R, and D correspond to $R^9$, $R^{16}$, and $R^8$, respectively, in the compounds of Formula I.

When the compound of interest contains an aryl amidine connected to the central phenyl ring (V in Formula I) by an acetylenic linking group the structure can be prepared as described in Scheme XII. Methods for the coupling of acetylenes to aryl bromides have been reviewed (Sandler and Karo, "Organic Functional Group Preparations" 2nd edition, Academic Press, INC, (1983) i r : p. 90; Larock, "Comprehensive Organic Transformations" VDH Publishers, (1989), p. 302–305). Both the amidines and the corresponding aminomethyl compounds (Scheme XII) can be prepared from the central nitrile intermediate. The aminomethyl group can be N-alkylated by treatment of the primary amine with a ketone plus $NaBH_3CN$ (*Synthesis* 135 (1975); Organic Preparations and Procedures, International 17, 317 (1983)).

In Scheme XII, E, R, and D correspond to $R^9$, $R^{16}$, and $R^8$, respectively, in the compounds of Formula I.

The acetylenic compounds described in Scheme XII can also be reduced to the corresponding cis alkenes by hydrogenation or hydroboration as described previously (Sandler and Karo, "Organic Functional Group Preparations" 2nd edition, Academic Press, INC, pp. 69–70).

When the compound of interest contains an aryl amidine connected to the central phenyl ring (V in Formula I) by a trans alkene linking group the structure can be prepared as described in Scheme XIII. Similar methods can be used to prepare the corresponding aminomethyl compounds (Scheme XIII). The aminomethyl group can be N-alkylated by treatment of the primary amine with a ketone plus $NaBH_3CN$ (*Synthesis* 135 (1975); Organic Preparations and Procedures, International 17: 317 (1983)).

Scheme XII

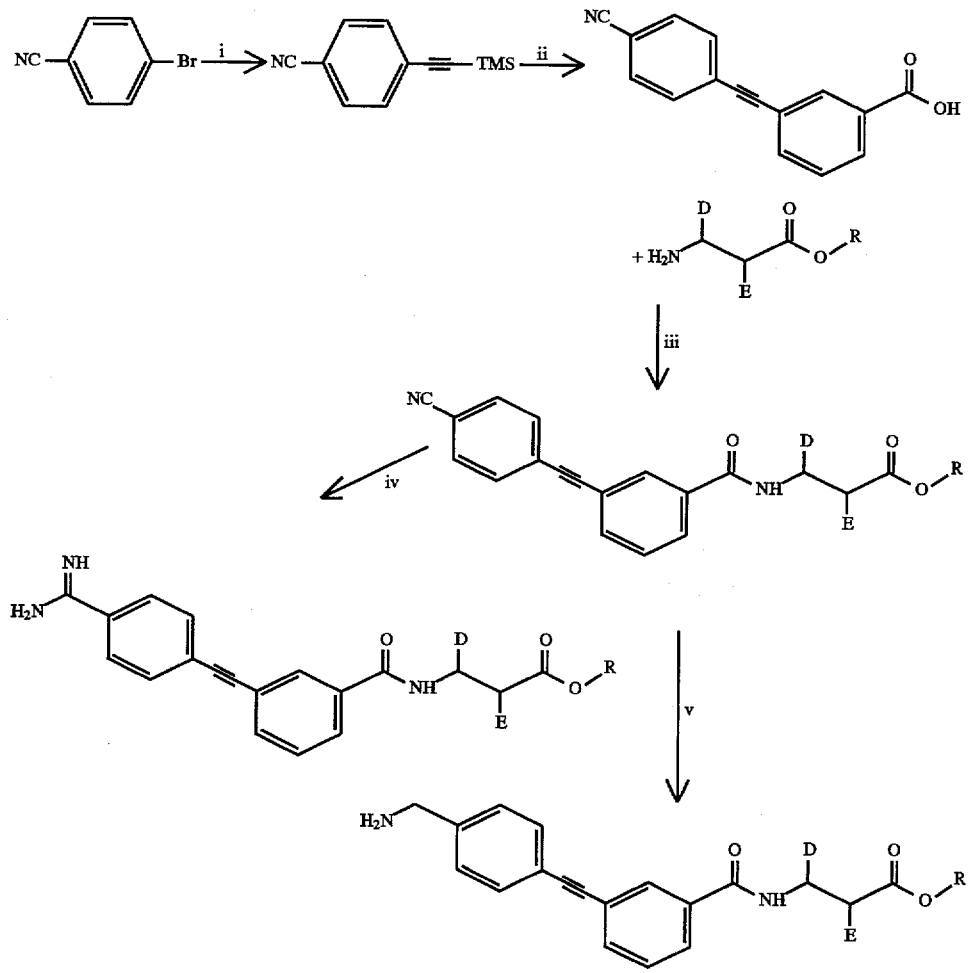

Reagents: i) Trimethylsilyl-acetylene, $Pd(Ph_3P)_3$, CuI, $Et_3N$; ii) 1) TBAF, 2) Methyl-3-Bromobenzoate, $Pd(Ph_3P)_3$, CuI, $Et_3N$, 3) LiOH or LiOTMS; iii) DCC or TBTU/$Et_3N$ iv) 1) HCl/methanol, 2) ammonia in methanol; or 1) $H_2S$/triethylamine, 2) MeI, 3) $NH_3$; v) 1) $NaBH_4CoCl_2$ 2)HCl.

Scheme XIII

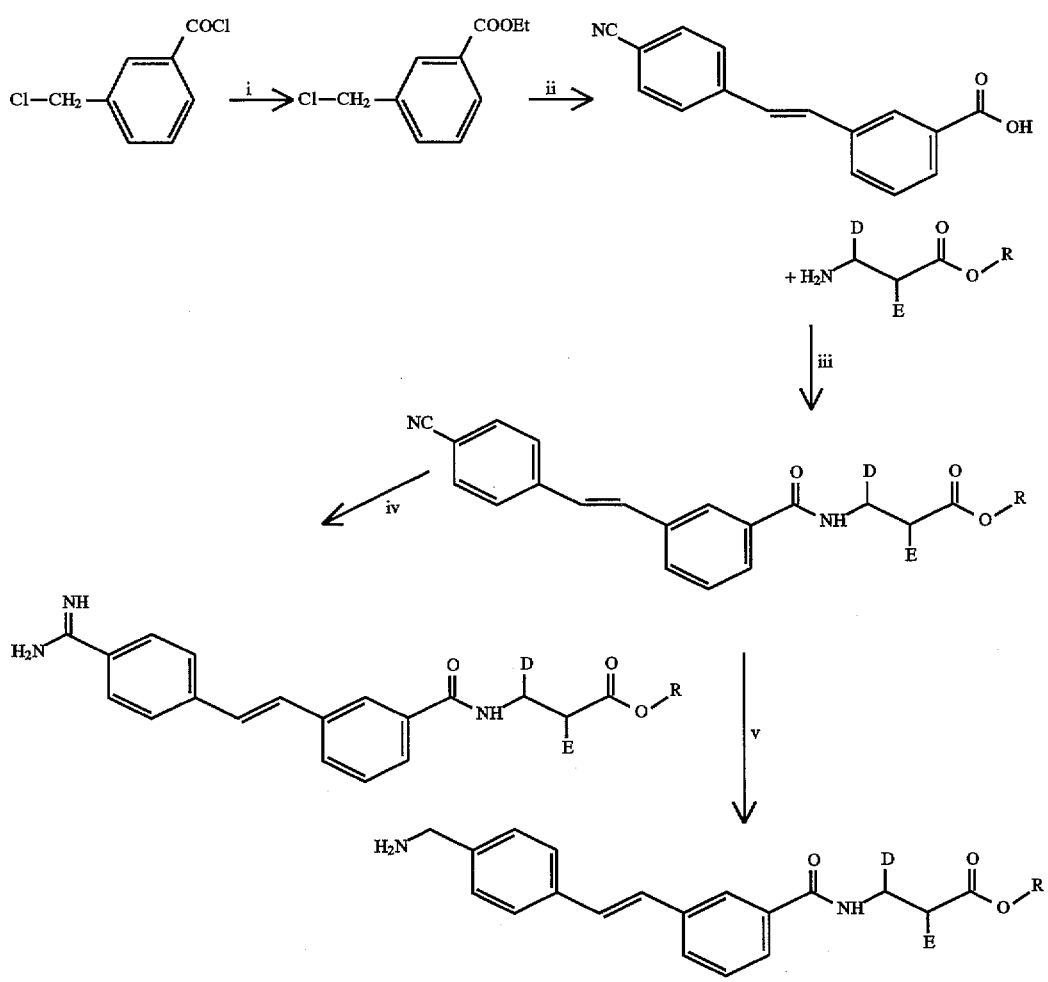

Reagents: i) EtOH; ii) 1) Ph₃P, 2) n-butyl lithium, 3) 4-cyanobenzaldehyde,
4) LiOH or LiOTMS; iii) DCC/HOBt or TBTU; iv) 1) HCl/methanol,
2) ammonia in methanol; or 1) H2S/triethylamine, 2) MeI, 3) NH3;
v) NaBH₄, CoCl₂.

In Scheme XIII, the substituents E, R, and D correspond to $R^9$, $R^{16}$, and $R^8$, respectively, in the compounds of Formula I.

The alkynes and alkenes described in Schemes XI and XII, respectively, can also be reduced to the corresponding alkanes by hydrogenation (Rylander, "Hydrogenation Methods" Academic Press, New York (1985), Chapter 3).

The central phenyl ring (V in Formula I) in the above compounds can be replaced with a variety of heterocycles (Q) by substitution of the appropriately functionalized heterocyclic starting material in Schemes I—XIII above. For example, compounds which have an aryl amidine connected to the central heterocyclic ring (Q) by an O—CH₂ linking group can be prepared as depicted in Scheme XIV.

Scheme XIV

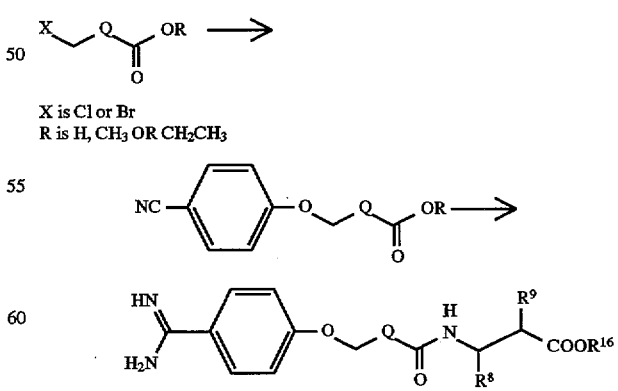

X is Cl or Br
R is H, CH₃ OR CH₂CH₃

The heterocyclic starting materials used in Scheme XIV are prepared as described below.

1) Five-Membered Heterocyclics

Table 1 lists representative five-membered aromatic heterocyclic starting materials suitable for use in the preparation of compounds of the present invention.

TABLE 1

Five-membered Aromatic Heterocyles

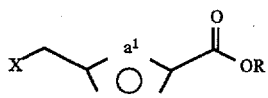

R = H, Me or Et
X = Cl or Br

| Q | $a^1$ | $a^3$ | $a^4$ |
|---|---|---|---|
| furan | O | CH | CH |
| furan | CH | CH | O |
| furan | CH | O | CH |
| thiophene | S | CH | CH |
| thiophene | CH | S | CH |
| thiophene | CH | CH | S |
| imidazole | N(H) | N(H) | CH |
| imidazole | N(H) | CH | N(H) |
| pyrrole | CH | CH | NH |
| pyrrole | NH | CH | CH |
| pyrrole | CH | NH | CH |
| pyrazole | CH | N(H) | N(H) |
| 1,2,4-triazole | N(H) | N(H) | N(H) |
| oxazole | N | O | CH |
| oxazole | O | CH | N |
| thiazole | S | N | CH |
| thiazole | S | CH | N |
| isoxazole | CH | N | O |
| isoxazole | CH | O | N |
| isothiazole | CH | N | S |
| isothiazole | CH | S | N |
| 1,2,4-oxadiazole | N | N | O |
| 1,2,4-oxadiazole | N | O | N |
| 1,2,4-thiadiazole | N | N | S |
| 1,2,4-thiadiazole | N | S | N |
| 1,3,4-oxadiazole | O | N | N |
| 1,3,4-thiadiazole | S | N | N | a) Furans

Synthesis of the 2,5-substituted linker (I) could be accomplished starting with an oxidative esterification (Corey, *J. Amer. Chem. Soc.*, 1968, 90, 5616) of the commercially available 5-methylfurfural (Scheme 1). The resulting methyl 5-methyl-2-furoic acid is then carefully monobrominated with NBS at room temperature, using VAZO® 52 as the initiator.

Scheme XVa

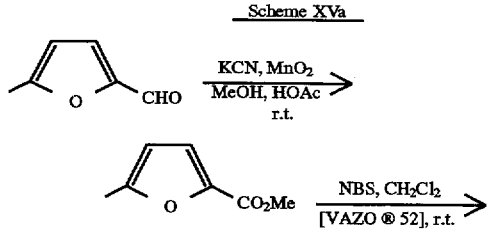

Scheme XVa -continued

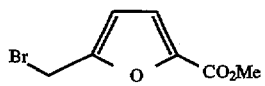

Synthesis of the corresponding 2,4-substituted isomer could be accomplished by using a similar approach starting with 4-methylfurfural (Chadwick, *J. Chem. Soc., Perkin Trans. I*, 1975, 2327, 2329) as shown in Scheme XVb.

Scheme XVb

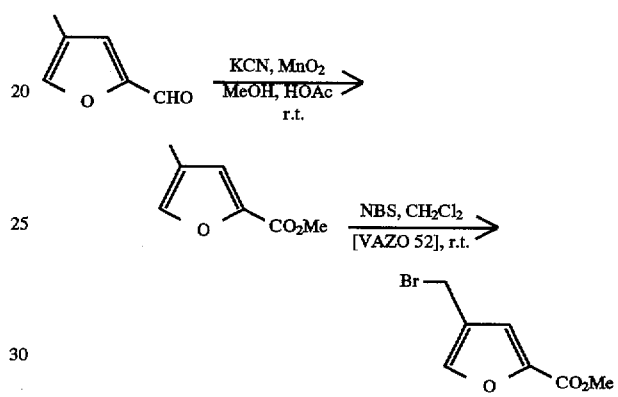

Analogously, the 3,5-isomeric furan can be prepared starting from 2-methyl-4-furaldedyde (Kotsuki, *Chem. Lett.* 1983, 7, 1007) using the same strategy (Scheme XVc).

Scheme XVc

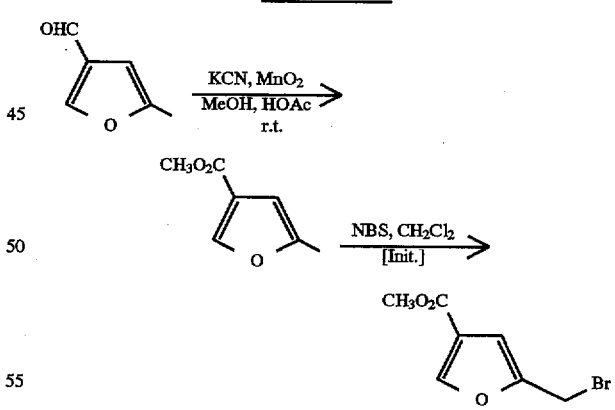

b) Thiophenes

Synthesis of 5-bromomethyl-2-thiophenecarboxylic acid hydrochloride can be accomplished starting from 5-methyl-2-thiophenecarboxylic acid (Rinker, *Recl. Trav. Chim. Pays Bas*, 1933, 52, 538, 546; Paal, *Chem Ber.* 1885, 18, 2253) using the same general strategy described above for the furan linkers, as shown by Scheme XVI.

Scheme XVI

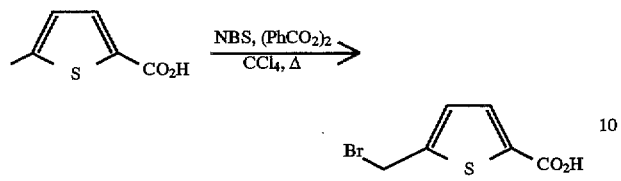

Access to the 2,4- and 3,5- linker species may be gained through a common starting material, 3-bromo-5-methylthiophene (Gronowitz, Holm, *Acta. Chem. Scand.* (*B*), 1976, 36, 505; Gronowitz, *Adv. Het. Chem.*, 1963, 1, 1).

Thus, as shown by Scheme XVIa, oxidation of the methyl group to the carboxylic acid, followed by its protection as the oxazoline (Meyers, *Tetrahedron Lett.*, 1989, 3303), lithiation of the bromide followed by formylation with DMF, reduction to the alcohol, conversion to the chloromethyl group, and finally acid deprotection leads to 3-(chloromethyl)thiophene-5-carboxylic acid.

Alternatively, initial lithiation of 3-bromo-5-methylthiophene followed by capture with methyl chloroformate gives methyl 5-methylthiophene-3-carboxylate. Free-radical bromination of the methyl group provides 5-(bromomethyl)thiophene-3-carboxylic acid.

d) Pyrroles

Synthesis of methyl 4-(bromomethyl)pyrrole-2-carboxylate hydrochloride is prepared from methyl methylpyrrole-2-carboxylate (Rapoport, *J. Org. Chem.*, 1964, 29, 2727) as illustrated in Scheme XVII.

Scheme XVII

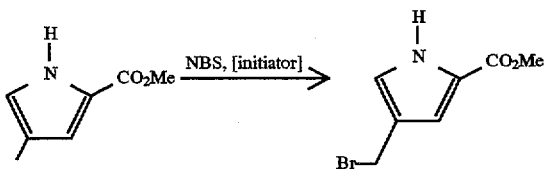

Preparation of methyl 5-(chloromethyl)pyrrole-2-carboxylate can be accomplished by the approach shown in Scheme XVIIa. A three-step conversion of pyrrole into methyl 5-formylpyrrole-2-carboxylate has been described (*Org. Syn.*, Coll Vol. 4, 1963, p831). Alternatively, Muchowski (*Tetrahedron Lett.*, 1988, 29, 777) has described the bis(dimethylamino)azafulvene dimer resulting from treatment of 2-formylpyrrole with dimethylamine. Such species may be lithiated at low temperatures and captured with a variety of electrophiles, including methyl chloroformate, to also give methyl 5-formylpyrrole-2-carboxylate. The aldehyde group is then reduced to the alcohol which is further converted to the chloromethyl compound.

Scheme XVIa

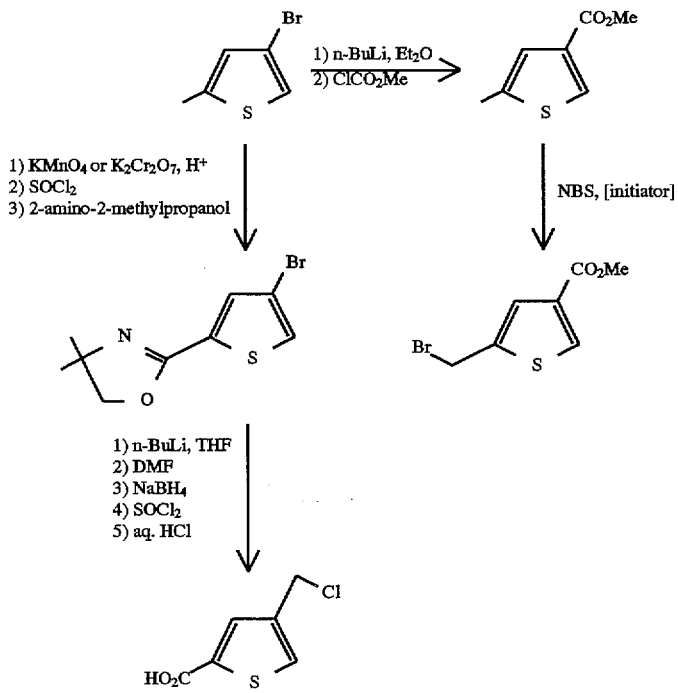

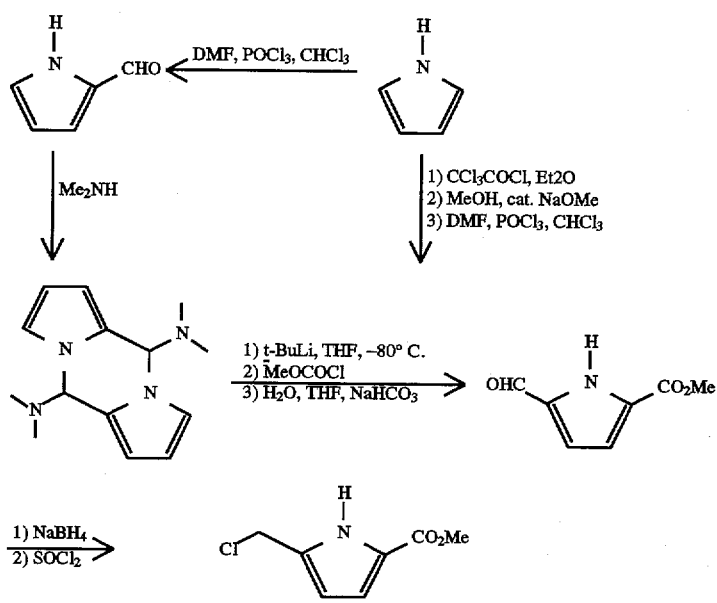

The third possible pyrrole starting material, methyl 5-(bromomethyl)pyrrole-3-carboxylate can be prepared according to Scheme XVIIb from methyl 5-methylpyrrole-3-carboxylate (Jones, *J. Amer. Chem. Soc.*, 1955, 77, 4069, 4072) by bromination as previously described above.

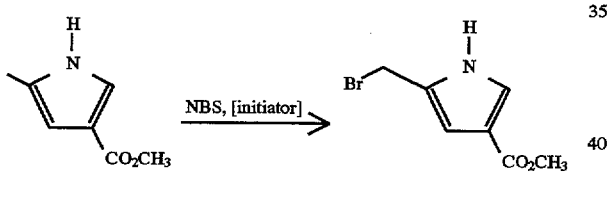

e) Pyrazole

Preparation of 5-(bromomethyl)pyrazole-3-carboxylic acid may be approached by the methods outlined in Scheme XVIII. Treatment of acetylacetone with hydrazine followed by selective oxidation of one of the two methyl groups of the resulting 3,5-dimethylpyrazole gives 5-methyl-pyrazole-3-carboxylic acid (Rothenburg, *Chem. Ber.*, 1894, 27, 1097). Alternatively, this compound may be prepared in one step by treatment of commercially available 2,4-dioxovaleric acid with hydrazine. The methyl group may then be converted to bromomethyl as previously described.

Alternatively, in the event of unwanted ring bromination during treatment with NBS, one may make use of ethyl 5-(benzoyloxy)-2,4-dioxo-valerate (Tschesche, *Chem. Ber.*, 2958, 91, 2074, 2079) to prepare an hydroxymethyl-substituted pyrazole intermediate which may then be transformed into an chloromethyl group by standard methods (Scheme XVIIIa).

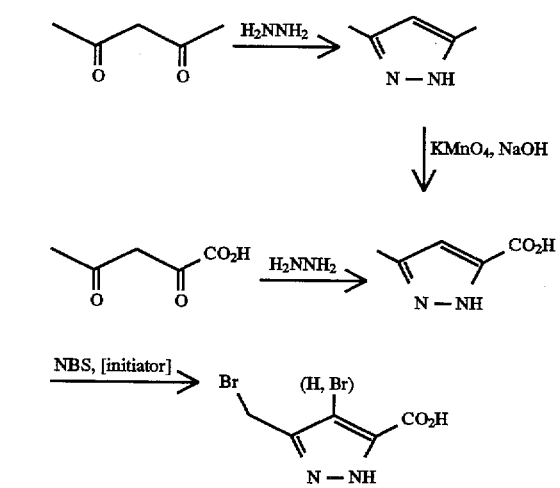

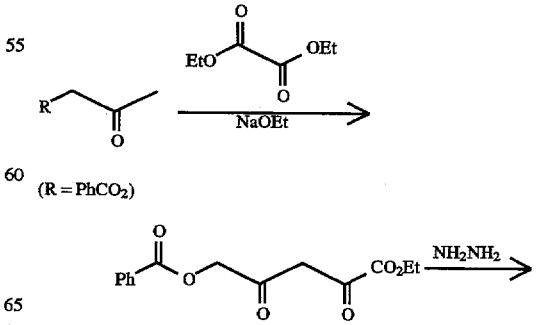

-continued
Scheme XVIIIa

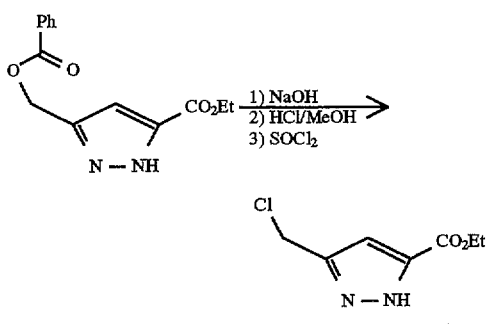

f) 1,2,4-Triazole

Synthesis of methyl 5-(bromomethyl)-1,2,4-triazole-3-carboxylate can be accomplished using the approach shown in Scheme XIX. The key intermediate, 3-(hydroxymethyl)-5-methyl-1,2,4-triazole, can be prepared according to the method of Francis (*Tetrahedron Lett.*, 1987, 28, 5133) whereby hydroxyacetylhydrazide is condensed with acetamidine under base catalyzed conditions followed by thermolytic ring closure. The synthesis then proceeds in a similar fashion to some of the previously described linkers above in which the aldehyde is oxidatively esterified using Corey's procedure and the methyl group converted to bromomethyl as described above.

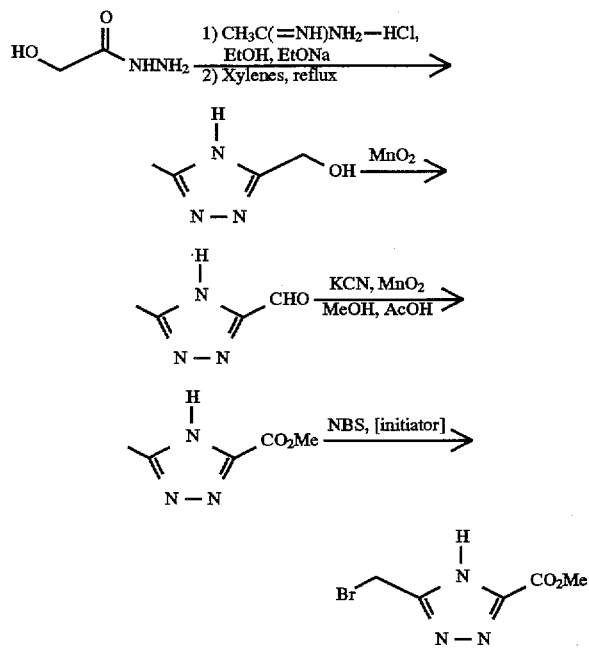

g) Oxazoles and Oxazolines

Yokokawa (*Synthetic Lett.*, 1992, 2, 153) has recently described the preparation and cyclization of N-acylserine ester derivatives to give 2-substituted-4,5-dihydrooxazole-4-carboxylate esters which, after oxidation, give the corresponding 2-substituted-oxazole-4-carboxylate esters. By inference, N-acylation of serine methyl ester with t-butoxyacetic acid, followed by cyclization, oxidation, deprotection and conversion to the chloride by standard methods should give methyl 2-(chloromethyl)oxazole-4-carboxylate, as outlined in Scheme XX below. Eliminiation of the oxidation step will give the corresponding oxazoline.

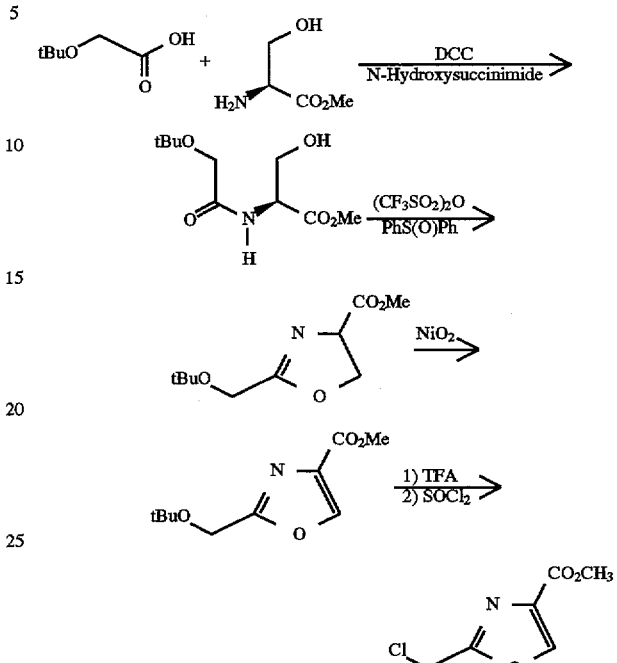

Tanimoto (*Chem. Pharm. Bull.*, 1984, 32, 1032) has reported the synthesis of ethyl 5-methyloxazole-2-carboxylate. The transformation of the methyl group to the bromomethyl, as previously described above, should lead to the ethyl 5-(bromomethyl)-2-carboxylate linker, as shown in Scheme XXa.

Scheme XXa

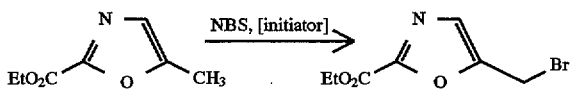

h) Thiazoles

Synthesis of ethyl 2-(hydroxymethyl)thiazole-5-carboxylate (and the corresponding carboxylic acid) has been reported (Poittevin, Hardy; Fr. Pat. DE2548505, [1976]). As illustrated in Scheme XXI below, further transformation of the hydroxymethyl group to chloromethyl as previously described should provide the 2-(chloromethyl) thiazole-5-carboxylic acid linker.

Scheme XXI

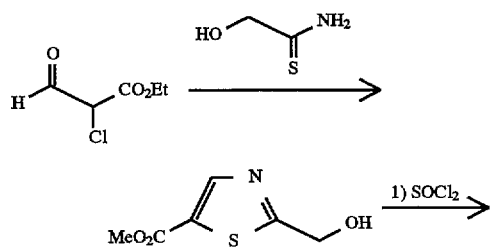

-continued
Scheme XXI

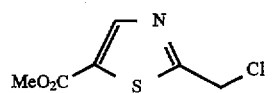

Synthesis of ethyl 5-methylthiazole-2-carboxylate has been accomplished by condensation of 2-bromopropionaldehyde with ethyl thiooxalamide (Erlenmeyer, Schmidt, *Helv. Chim. Acta.*, 1946, 29, 1957). As shown in Scheme XXIa, further transformation of the methyl group into a bromomethyl, provides 5-(bromomethyl)thiazole-2-carboxylic acid.

Scheme XXIa

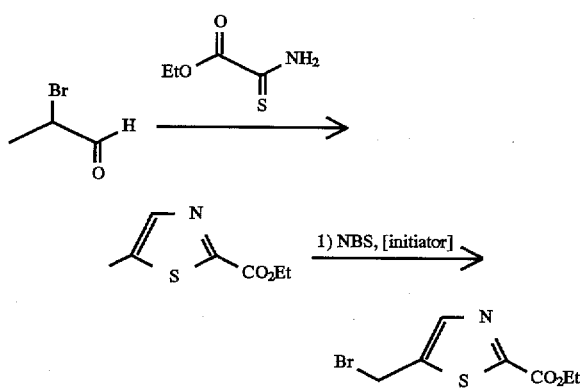

In the event of undesired ring bromination in the above scheme, one may make use of 2-chloro-3-(benzoyloxy) propionaldehyde (Hartman, *Theory Pract. Affinity Tech.* [*Int. Symp.*], 1978, 113) instead of 2-bromopropionaldehyde. Following comparable formation of the thiazole ring system, selective hydrolysis of the benzoate ester and conversion of hydroxymethyl to chloromethyl as described above, (Scheme XXIb). Related known propionaldehyde derivatives such as 2-bromo-3-acetoxypropionaldehyde and 2-bromo-3-methoxypropionaldehyde may also serve as useful inroads to this series of thiazole compounds.

Scheme XXIb

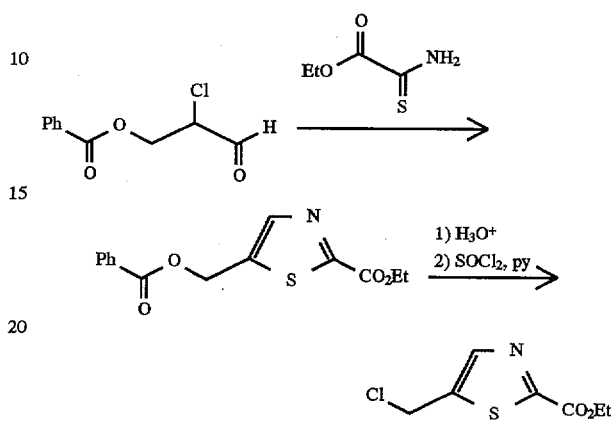

i) Isoxazoles and Isothiazoles

Analogous to the preparation of the pyrazole linker described above, an appropriate ester of 2,4-dioxovaleric acid (or the commercially available carboxylic acid itself) may be condensed with hydroxylamine to give, in this case, a mixture of the isomeric 3,5-disubstituted isoxazoles. Following separation of these isomers, the methyl group is converted to the bromomethyl as previously described. Again, as with the pyrazole case, in the event of unwanted ring bromination during treatment with NBS, one may instead start the synthesis using ethyl 5-(benzoyloxy)-2,4-dioxovalerate (Tschesche, *Chem. Ber.*, 1958, 91, 2074, 2079). See Scheme XXII Scheme XXII

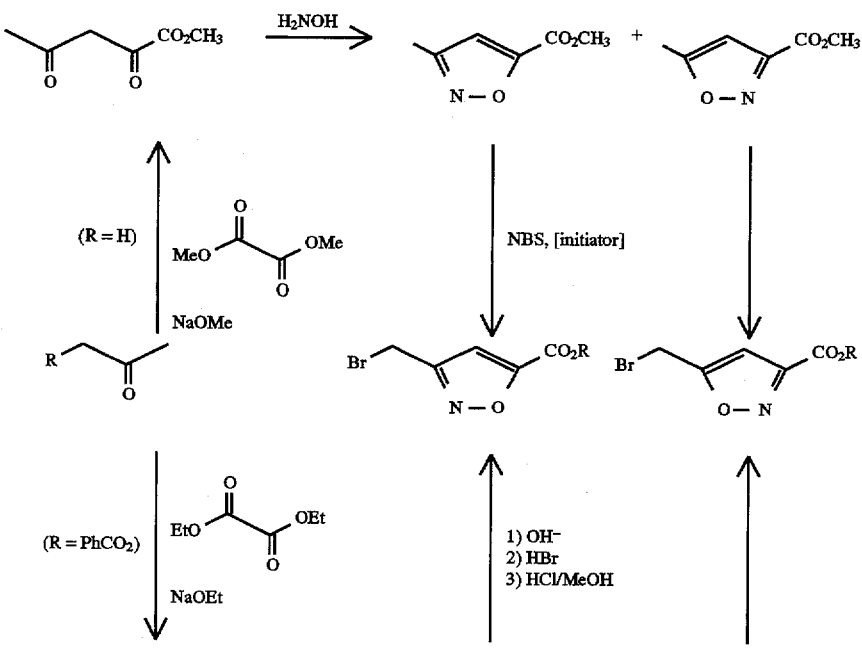

-continued
Scheme XXII

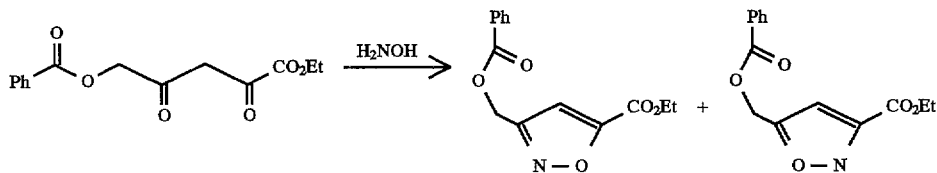

The corresponding isothiazoles can be prepared from their oxygen cogeners via a three step process involving reductive ring opening, replacement of oxygen by sulfur using phosphorus pentasulfide, and oxidative ring closure (Newkome and Paudler, "Contemporary Heterocyclic Chemistry", Wiley-Interscience, N.Y., 1982; p41). Scheme XXIIa illustrates the approach.

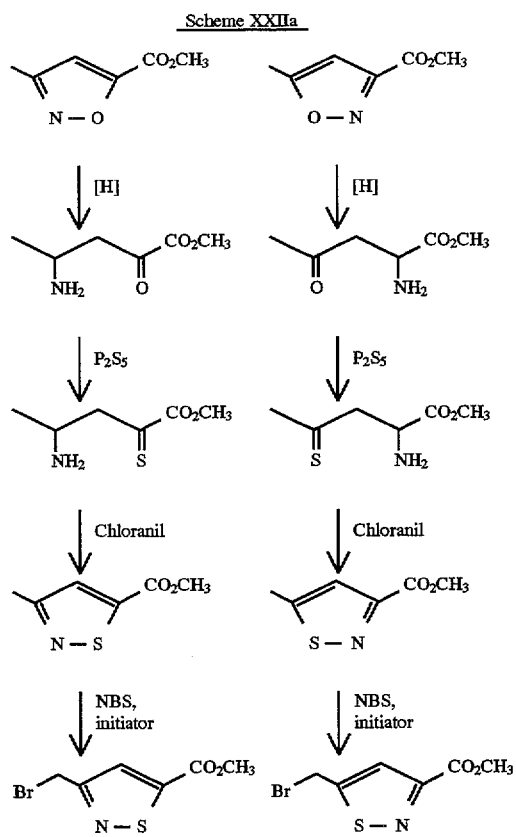

j) Oxadiazoles and Thiadiazoles

The transformation of 3,5-dimethyl-1,2,4-oxadiazole to 3-oximino-5-methyl-1,2,4-oxadiazole has been described (Bedford, J. Med. Chem., 1986, 29, 2174). As further illustrated in Scheme XXIII, oxidative esterification of this oxime according to Said (Synth. Commun., 1992, 22, 1851) leads to the corresponding ester. Conversion of methyl to chloromethyl as described above gives the desired chloroester.

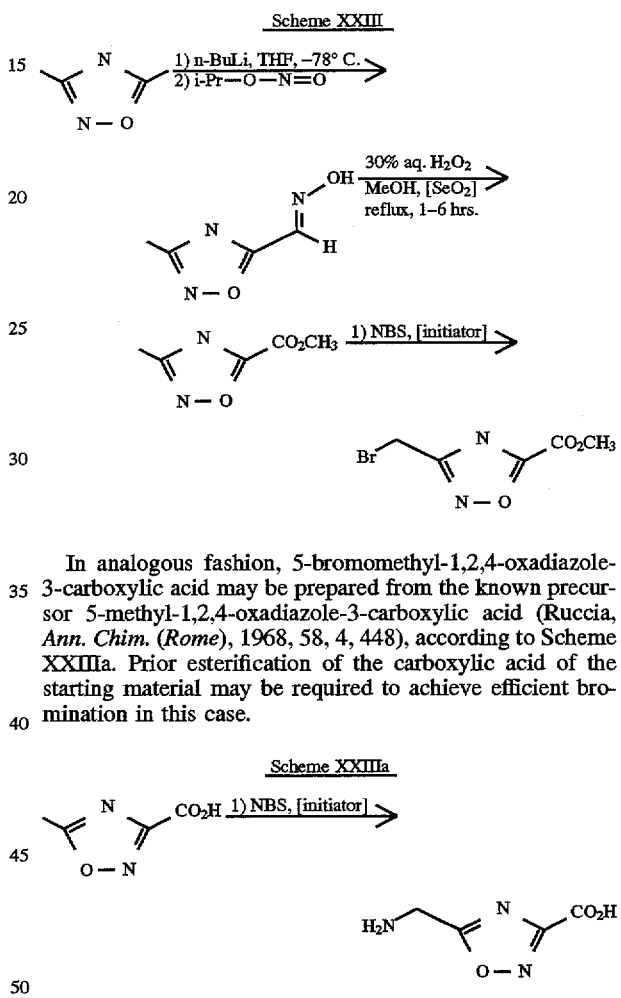

In analogous fashion, 5-bromomethyl-1,2,4-oxadiazole-3-carboxylic acid may be prepared from the known precursor 5-methyl-1,2,4-oxadiazole-3-carboxylic acid (Ruccia, Ann. Chim. (Rome), 1968, 58, 4, 448), according to Scheme XXIIIa. Prior esterification of the carboxylic acid of the starting material may be required to achieve efficient bromination in this case.

The condensation of acetamidine with trichloromethylsulfenyl chloride to give 3-methyl-5-chloro-1,2,4-thiadiazole has been reported (Goerdeler, Chem. Ber., 1957, 90, 182, 184). Furthermore, MacLead (J. Med. Chem., 1990, 33, 2052) has demonstrated displacement of the chlorine with various carbon and heteroatomic nucleophiles. Consequently, as shown in Scheme XXIIIb, displacement with cyanide followed by conversion of methyl to bromomethyl, and standard hydrolysis of the cyano group to the acid leads to 3-bromomethyl-5-carboxy-1,2,4-thiadiazole. In an alternative approach also shown in Scheme XXIIIb, 3,5-dimethyl-1,2,4-thiadiazole (Troyanski, Izv. Akad., Nauk. SSSR, Ser. Khim., 1986, 5, 1143) may be treated with isoamylnitrite in the presence of potassium ethoxide to give 3-oximino-5-methyl-1,2,4-thiadiazole (Benschop, J. Med. Chem., 1979, 22, 1306). Oxidation of the oxime to the methyl ester (Said, Synth. Commun., 1992, 22, 1851) followed by transformation of methyl to bromomethyl as previously described also leads to the desired compound.

Scheme XXIIIb

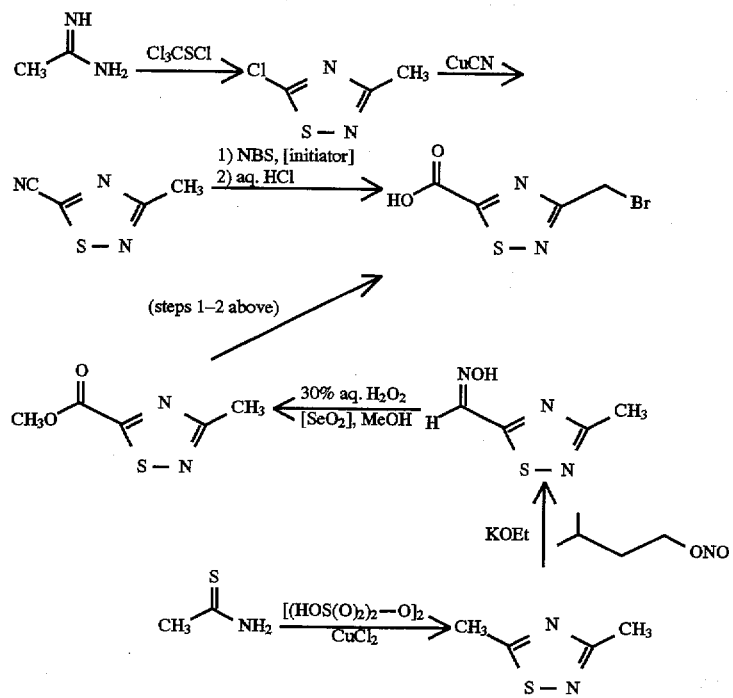

In Scheme XXIIIc, methyl 5-methyl-1,3,4-oxadiazole-2-carboxylate (Werber, *Atti. Scand. Accad. Sci. Lett., Arti Palermo Parte* 1, 1969–1970, 30, 175) is transformed to methyl 5-bromomethyl-1,3,4-oxadiazole-2-carboxylate using the methods described above.

Scheme XXIIIc

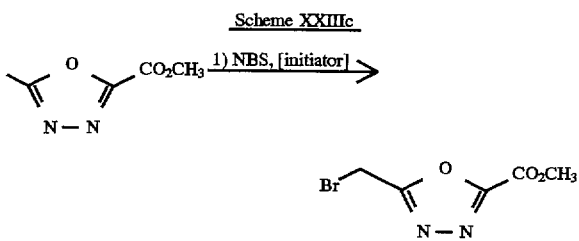

Analogously, methyl 5-methyl-1,3,4-thiadiazole-2-carboxylyate, prepared from the corresponding aldehyde precursor (Conway, EP125094 [1984]), is transformed by standard techniques to methyl 5-bromomethyl-1,3,4-thiadiazole-2-carboxylic acid as outlined in Scheme XXIIId.

Scheme XXIIIc

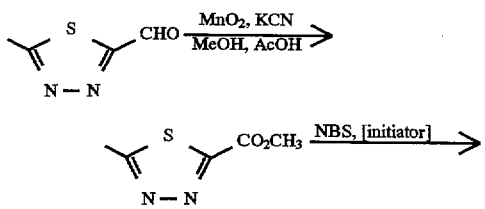

-continued
Scheme XXIIIc

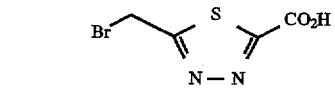

2) Six-Membered Heterocycles

Table 2 lists representative six-membered aromatic heterocyclic starting materials suitable for use in the preparation of compounds of the present invention.

TABLE 2

Six-membered Heterocycles

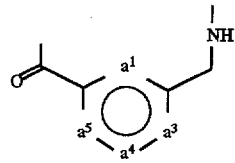

| Class | $a^2$ | $a^3$ | $a^4$ | $a^5$ |
|---|---|---|---|---|
| pyridine | N | CH | CH | CH |
| pyridine | CH | CH | CH | N |
| pyridine | CH | CH | N | CH |
| pyridine | CH | N | CH | CH |
| pyrazine | N | CH | N | CH |
| pyrimidine | N | CH | CH | N |
| pyrimidine | N | N | CH | CH |
| pyrimidine | CH | N | CH | N |

TABLE 2-continued

Six-membered Heterocycles

| Class | $a^a$ | $a^3$ | $a^4$ | $a^5$ |
|---|---|---|---|---|
| pyridazine | CH | N | N | CH |
| pyridazine | CH | CH | N | N |
| 1,2,3-triazine | CH | N | N | N |
| 1,2,4-triazine | N | N | N | CH |
| 1,2,4-triazine | N | CH | N | N | a) Pyridines

The 2,6-substituted linker may be prepared from commercially available 6-methylpicolinic acid (TCI, Japan) via Scheme XXIV. Esterification followed by previously discussed benzylic-type bromination, gives methyl 6-(bromomethyl)picolinate.

Scheme XXIV

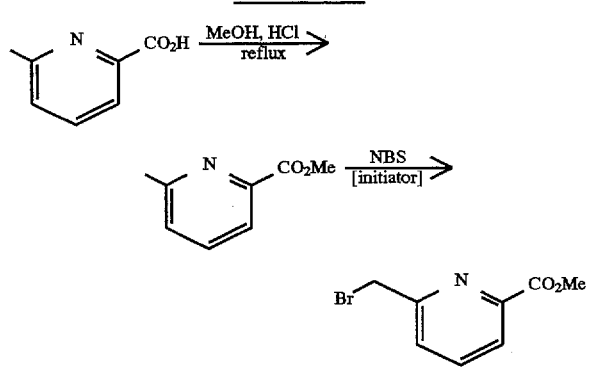

Synthesis of ethyl 4-(bromomethyl)picolinate is depicted in Scheme XXIVa beginning with 4-picoline which is converted to 2-amino-4-picoline according to Tschitchibabin (*J. Russ. Phys. Chem. Soc.*, 1914, 46, 1216). The amine in turn is subjected to Sandmeyer conditions to give the corresponding bromide. Halogen-metal exchange followed by quenching with ethyl chloroformate gives ethyl 4-methylpicolinate which is brominated using the conditions described above.

Scheme XIVa

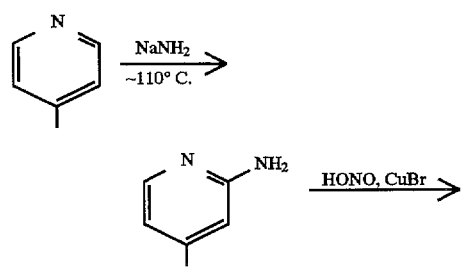

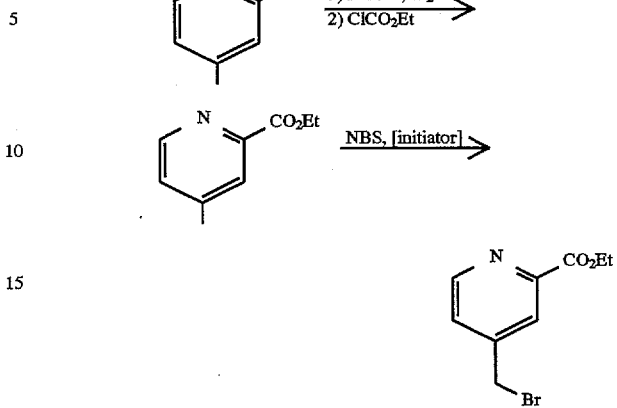

Selective reduction of the half acid/ester of methyl pyridine-3,5-dicarboxylate (Delarge, *J. Pharm. Helv.*, 1969, 44,637) with diborane to methyl 5-(hydroxymethyl) pyridine-3-carboxylate followed by conversion of hydroxymethyl to the corresonding chloride ethyl 5-(chloromethyl)-pyridine-3-carboxylate as illustrated in Scheme XIVb below.

Scheme XIVb

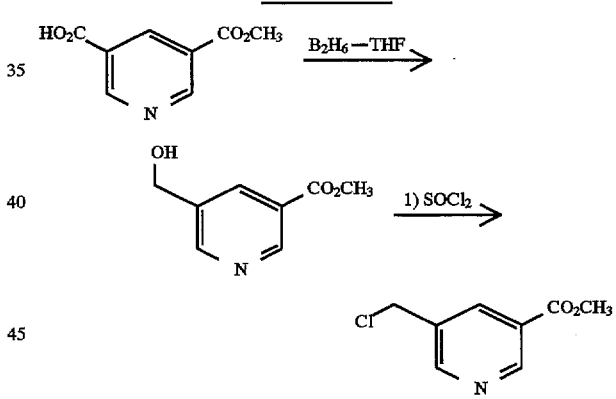

Synthesis of ethyl 2-(chloromethyl)pyridine-4-carboxylate (Scheme XIVc) may be carried out starting with 2-bromo-4-methylpicoline. Halogen/metal exchange followed by quenching with DMF gives the formyl compound, which is further converted to the chloromethyl compound by reduction and treatment with thionyl chloride. Acidic deprotection completes the sequence.

Scheme XIVc

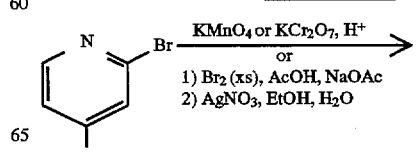

-continued
Scheme XIVc

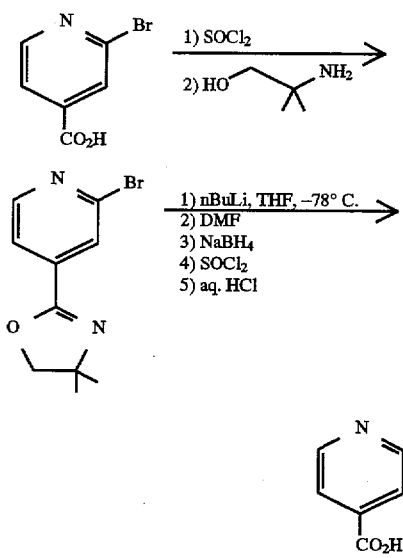

b) Pyrazine

-continued
Scheme XXV

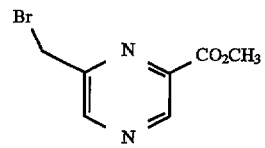

c) Pyrimidines

Scheme XXVI illustrates the preparation of either methyl 4-(chloromethyl)pyrimidine-2-carboxylate or 2-(chloromethyl)pyrimidine-4-carboxylic acid from the common intermediate 2-formyl-4-cyanopyrimidine (Stenck, EP335832, 1989; CA: 112, 21, 197872w). For the former target, the aldehyde is oxidized to the ester (Corey procedure). Reduction of the nitrile to the aldehyde using the Stephen reaction (Mosettig, Org. React. 8, 219–257, 1954) borohydride reduction and reaction with thionyl chloride provides the desired ester.

Alternatively, selective reduction of the aldehyde to the hydroxymethyl group followed by its conversion to the chloride and hydrolysis of the nitrile gives the corresponding carboxylic acid.

Scheme XXVI

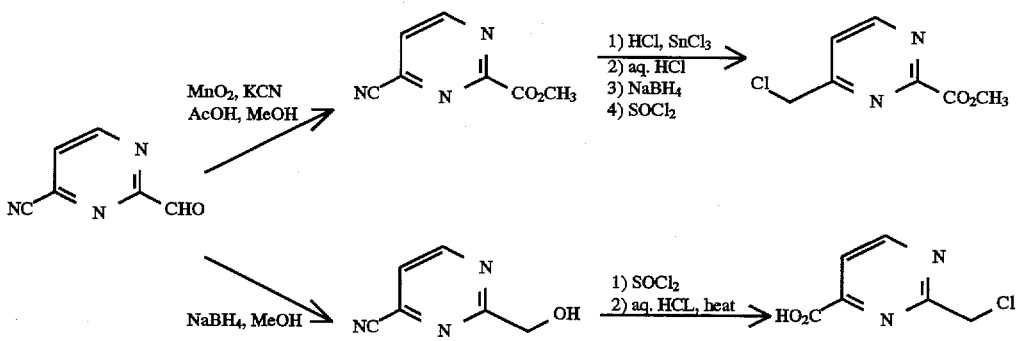

The pyrazine linker may be prepared as shown in Scheme XXV from 6-methylpyrazine-2-carboxylic acid (Felder, *Chem. Ber.,* 1967, 100, 2, 255; Spoerri, *J. Amer. Chem. Soc.,* 1946, 68, 526) by esterification and conversion of the methyl group to a bromomethyl as previously described.

The third possible isomer in this series, methyl 6-(bromomethyl)-pyrimidine-3-carboxylate can be prepared from 6-methylpyrimidine-3-carboxylic acid (Kiener, EP 442430; CA: 116, 7, 57572f). Analogous to Scheme XXV (and others above), esterification followed by transformation of methyl to aminomethyl gives the desired linker, as shown in Scheme XXVIa.

Scheme XXV

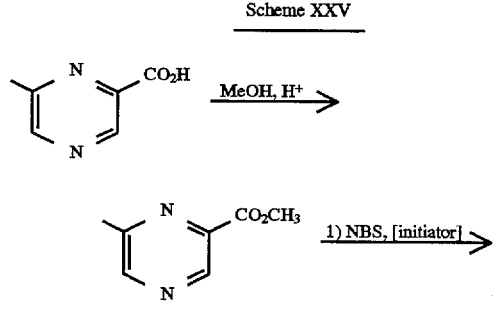

Scheme XXVIa

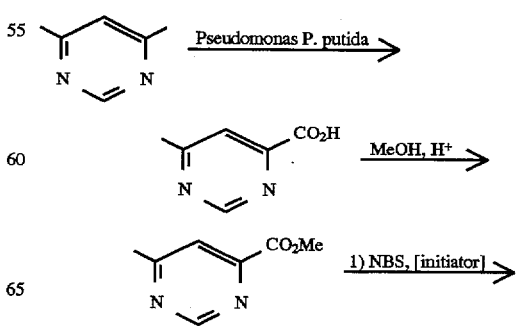

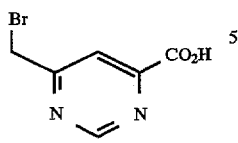

d) Pyridazines

Ethyl 6-methylpyridazine-4-carboxylate has been described (Heinisch, *Tetrahedron*, 1985, 41, 1199; Turck, C. R. Acad. Sci., Ser. C, 1973, 277, 33). Conversion of methyl to bromomethyl as previously described in several other schemes above, is illustrated in Scheme XXVII.

Scheme XXVII

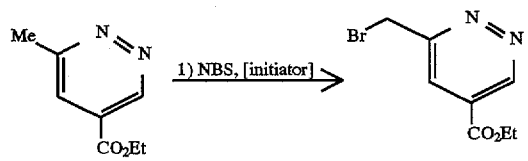

e) Triazines

Various methods have been described for the oxidative ring expansion of N-amino-pyrazoles to 1,2,3-triazines (Ohsawa, *J. Chem. Soc., Chem. Commun.*, 1980, 1182; Ibid, 1981, 1174; Ohsawa, *J. Org. Chem.*, 1985, 50, 5520; Ogata, *Chem. Pharm. Bull.*, 1988, 36, 3838). Thus, N(1)-amino-5-methylpyrazole-3-carboxylic acid, obtained from the corresponding pyrazole described above and hydroxylamine-O-sulfonic acid (Neunhoeffer, *Liebigs Ann. Chem.*, 1985, 9, 1732) is converted to 6-methyl-1,2,3-triazine-4-carboxylic acid according to Scheme XXVIII. Standard transformation of methyl to bromomethyl then provides ethyl 6-(bromomethyl)-1,2,3-triazine-4-carboxylate.

Scheme XXVIII

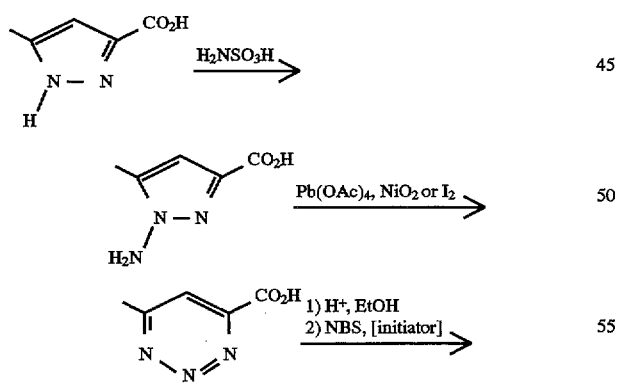

-continued
Scheme XXVIII

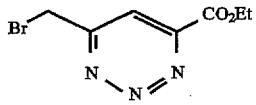

Rykowski has described the base-catalysed oximation of 3-methyl-1,2,4-triazine to give 3-methyl-5-oximino-1,2,4-triazine (*Tetrahedron Lett.*, 1984, 4795). Oxidative esterification of the oxime group according to Said (*Synth. Commun.*, 1992, 22, 1851) followed by bromination leads to methyl 3-bromomethyl-1,2,4-triazine-5-carboxylate. (Scheme XXVIIIa)

Scheme XXVIIIa

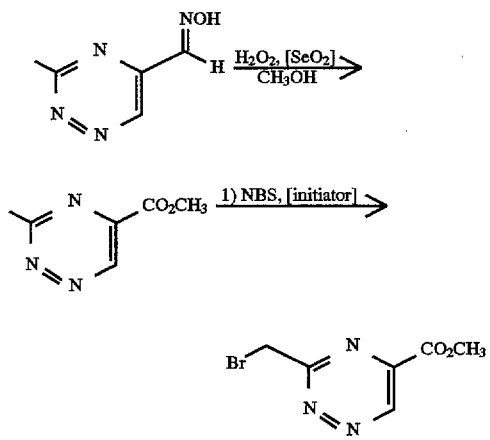

Compounds which have an aryl amidine connected to a central heterocyclic ring, for example isoxazole, by a $CH_2$—O linking group can be prepared as shown in Scheme XIXa.

Scheme XIXa

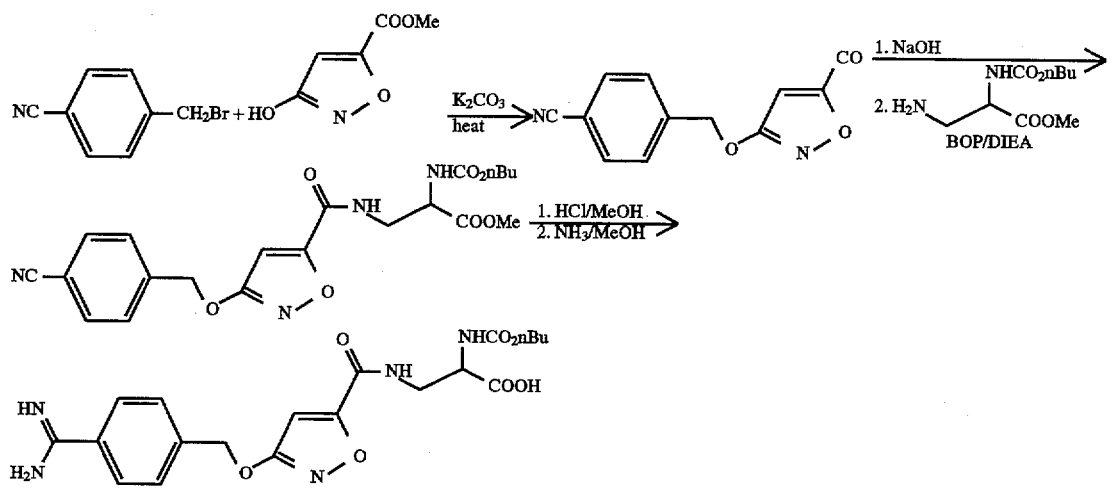

Alkylation of methyl 3-hydroxyisoxazole-5-carboxylate with 4-cyano-α-bromotoluene in the presence of a base, such as potassium carbonate, gives cyanophenylmethoxy)-5-carboxymethylisoxazole. Saponification of the ester and condensation with an appropriately substituted and protected diaminopropionic acid derivative gives the amide.

diaminpropionate using conditions described above. The piperidine nitrogen is deprotected and treated with N,N,-diCBz-S-methylisothiourea to give a protected amidinopiperdine. Hydrogenation gives the amidinopiperidine compounds as the methyl esters.

Scheme XIXb

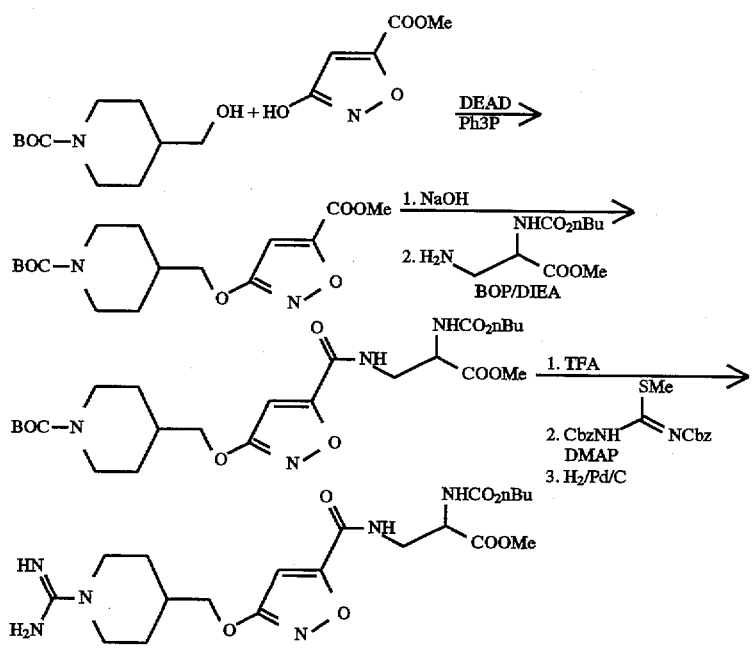

Conversion of the nitrile to the amidine as described above and hydrolysis of the ester gives the desired product.

Scheme XIXb outlines the synthesis of the analogous compounds where $R^1$ is 4-(1-amidinopiperidinyl) instead of 4-amidinophenyl. After initial condensation of N-BOC-4-piperidinylcarbinol with methyl 3-hydroxyisoxazole-5-carboxylate under Mitsunobu conditions, the intermediate ester is saponified and condensed with a 1,3-

The detailed processes for preparing the compounds of Formula I are illustrated by the following Examples. It is, however, understood that this invention is not limited to the specific details of these examples. Melting points are uncorrected. Proton nuclear magnetic resonance spectra ($^1$H NMR) were measured in chloroform-d ($CDCl_3$) unless otherwise specified and the peaks are reported in parts per million (ppm) downfield from tetramethylsilane (TMS). The coupling patterns are reported as follows: s, singlet; d, doublet; t, triplet; q, quartet; qt, quintet; m, multiplet.

Example 2a

Methyl $N^2$-t-butoxycarbonyl-$N^3$-(3-(4-amidinophenyloxymethyl)benzoyl)-L-2,3-diaminopropionate, TFA salt 2.0 g of 3-N-[3-(4-amidinophenyloxymethyl)benzoyl]-L-2,3-diaminopropionate (5.4 mole) was dissolved in 30 ml solvent mixture (AcCN:$H_2O$:DMF 5:4:1). 1.25 ml di-t-butyldicarbonate (5.4 mmole) was added, then about 5 ml saturated $NaHCO_3$ solution was added, to bring the pH to 7.2 The solution was stirred 1½ hours at room temperature. Analytical HPLC (Vydac $C_{18}$ column, 1 ml/min., 0–50% B/50 min., A=99.9% $H_2O$/0.1% TFA, B=90% ACN/9.9% $H_2O$/0.1% TFA) showed the starting material was gone, and the appearance of a new peak. The reaction mixture was diluted 1:1 with 50% HOAc and purified directly on a Vydac prep $C_{18}$ HPLC column, 10 ml/min., 22–42% B/40 min., detection at 290 nm. After lyophilization the overall yield was about 10% purified material. The identify of the material was confirmed by mass spec. (DCI) (Predicted MW 471.2; actual 471).

Example 6

Methyl $N^2$-(3-phenylpropionyl)-$N^3$-(3-(4-amidinophenyloxymethyl)benzoyl)-L-2,3-diaminopropionate TFA salt (XXXX).

This compound was synthesized using the similar procedure as for XXXVIII from XXXVI (1 mmol, 520 mg), hydrocinnamoyl chloride (1 mmol, 0.15 mL) and $NaHCO_3$ (2.5 mmol, 200 mg). Purification on reversed phase HPLC gave 130 mg product. NMR (DMSO-$d_6$): δ9.14 (s, 2H); 8.90 (s, 2H); 8.64 (t, 1H); 8.35 (d, 1H); 7.91 (s, 1H); 7.80 (d, 2H); 7.78 (d, 1H); 7.63 (d, 1H); 7.52 (t, 1H); 7.20 (m, 7H); 5.30 (s, 2H); 4.50 (m, 1H); 3.59 (s, 3H); 3.56 (m, 2H); 2.80 (m, 2H); 2.44 (m, 2H).

$N^2$-(3-phenylpropionyl)-$N^3$-(3-(4-amidinophenyloxymethyl)benzoyl)-L-2,3-diaminopropionic acid TFA salt (XXXXI).

XXXX (50 mg) was treated with 2 mL methanol and 1 mL 1 N NaOH for 1 hour and the solution was acidified with acetic acid. Purification on reversed phase HPLC gave 35 mg product.

Example 9

Methyl $N$-$^2$-1-butyloxycarbonyl-$N^3$-(3-(4-ammidinophenyloxymethyl)benzoyl)-L-2,3-diaminopropionate TFA salt (XXXVIII).

To a solution containing XXXVI (4 mmol, 2.05 g) and $NaHCO_3$ (10 mmol, 0.8 g) in 5 mL water, mL acetonitrile and 2 mL DMF cooled in an ice bath was added butyl chloroformate (4 mmol, 0.51 mL). The solution was stirred for 1 hour, filtered, and acidified with acetic acid. Purification on reversed phase HPLC gave 450 mg product. NMR (DMSO-$d_6$): δ9.15 (s, 2H); 8.92 (s, 2H); 8.62 (t, 1H); 7.92 (s, 1H); 7.81 (d, 2H); 7.79 (d, 1H); 7.62 (d, 1H); 7.57 (d, 1H); 7.50 (t, 1H); 7.24 (d, 2H); 5.30 (s, 2H); 4.28 (m, 1H); 3.95 (t, 2H); 3.60 (s, 3H); 3.59 (m, 2H); 1.50 (m, 2H); 1.30 (m, 2H); 0.86 (t, 3H).

$N^2$-1-butyloxycarbonyl-$N^3$-(3-(4-amidinophenyloxymethyl)benzoyl)-L-2,3-diaminopropionic acid TFA salt (XXXIX).

XXXVIII (150 mg) was treated with 3 mL methanol and 3 mL 1 N NaOH for 1 hour and the solution was acidified with acetic acid. Purification on reversed phase HPLC gave 110 mg product.

Example 9b

Valeric acid, N-hydroxysuccinimide ester

N,N-Dicyclohexylcarbodiimide (4.12 g; 0.02 mole) was added to a solution of valeric acid (2.04 g; 0.02 mole) and hydroxysuccinimide(2.3 g; 0.02 mole) in 60 ml of dioxane with cooling. The reaction mixture was allowed to stand overnight at room temperature. The formed dicyclohexylurea was filtered and washed with dioxane. The filtrate was evaporated under reduced pressure to give crude N-hydroxysuccinimide ester of valeric acid as an oil which was used without further purification.

Ethyl $N^2$-butyryl-$N^3$-(3-(4-amidinophenyloxymethyl) benzoyl)-L-2,3-diaminopropionate, TFA salt A solution of the N-hydroxysuccinimide of valeric acid (0.24 g; 0.001 mole) in 4 ml dimethylformamide was added to a solution of ethyl $N^3$-[3-(4-Aminidophenyloxymethyl) benzoyl]-L-2,3-diaminoprpionate (0.48 g, 0.001 mole) and N-methylmorpholine (0.13 g; 0.001 mole) in 4 ml dimethylformamide. After 2 hrs the solvent was removed under vacu The dry residue was dissolved in 10% acetic acid/water, purified using HPLC(Vydac C-18 prep column; program from 10% to 50% buffer 1% per min., 10 ml per min. Buffer A: 99.9% water +0.1% TFA Buffer B: 90% Acetonitrile +9.9 % water +0.1% TFA) and lyophilized to give the title compound. (M+1)=455.

Example 14

Methyl $N^2$-1-butanesulfonyl-$N^3$-Boc-L-2,3-diaminopropionate (XXX). To a solution of XXIII (3 mmol, 767 mg) in 10 mL THF was added 1-butanesulfonyl chloride (3 mmol, 0.393 mL) followed by triethylamine (7 mmol, 0.974 mL) and the solution was stirred at 50° C. overnight and then at 60° C. for 6 hours and concentrated. The residue was taken up in ethyl acetate and the solution was washed with 1% citric acid, brine, $NaHCO_3$ and brine, dried ($MgSO_4$), and concentrated. Crystallization from ether gave 570 mg (56%) product. NMR (DMSO-$d_6$): δ7.66 (d, 1H); 6.92 (t, 1H); 4.04 (m, 1H); 3.64 (s, 3H); 3.21 (m, 2H); 2.96 (m, 2H); 1.61 (m, 2H); 1.37 (s, 9H); 1.36 (m, 2H); 0.88 (t, 3H).

Methyl $N^2$-1-butanesulfonyl-L-2,3-diaminopropionate TFA Salt (XXXI).

XXX (1.68 mmol, 570 mg) was treated with 60% TFA in methylene chloride (5 mL) for 1 hour and the solution was concentrated. Yield 600 mg (100%). NMR (DMSO-$d_6$): δ8.06 (b, 3H); 7.95 (d, 1H); 4.30 (m, 1H); 3.72 (s, 3H); 3.20 (m, 1H); 3.08 (m, 2H); 3.00 (m, 1H); 1.66 (m, 2H); 1.39 (m, 2H); 0.89 (t, 3H).

Methyl $N_2$-1-butanesulfonyl-$N^3$-(3-chloromethylbenzoyl)-L-2,3-diaminopropionate (XXXII). This compound was synthesized using a similar procedure as for I from 3-chloromethylbenzoyl chloride (2 mmol, 284 mg), XXXI (2 mmol, 704 mg) and triethylamine (5 mmol, 0.70 mL). Purification on a silica gel column using ethyl acetate/hexane gave 490 mg (63%) crystalline product. NMR (DMSO-$d_6$): δ8.63 (t, 1H); 7.90 (s, 1H); 7.82 (d, 1H); 7.79 (d, 1H); 7.61 (d, 1H); 7.50 (t, 1H); 4.82 (s, 2H); 4.23 (m, 1H); 3.64 (s, 3H); 3.57 (m, 2H); 2.95 (m, 2H); 1.60 (m, 2H); 1.28 (m, 2H); 0.80 (t, 3H).

Methyl $N^2$-1-butanesulfonyl-$N^3$-(3-(4-cyanophenyloxymethyl)benzoyl)-L-2,3-diaminopropionate (XXXIII). This compound was synthesized in a similar way as for II from XXXII (1.15 mmol, 450 mg), 4-cyanophenol (1.15 mmol, 137 mg) and potassium carbonate (2.3 mmol, 318 mg). Yield 470 mg (86%). NMR (DMSO-$d_6$): δ8.64 (t, 1H); 7.94 (s, 1H); 7.80 (m, 4H); 7.64 (d, 1H); 7.52 (t, 1H);

7.20 (d, 2H); 5.26 (s, 2H); 4.24 (m, 1H); 3.64 (s, 3H); 3.58 (m, 2H); 2.95 (m, 2H); 1.60 (m, 2H); 1.27 (m, 2H); 0.80 (t, 3H).

Methyl N$^2$-1-butanesulfonyl-N$^3$-(3-(4-amidinophenyloxymethyl)benzoyl)-L-2,3-diaminopropionate TFA salt (XXXIV). This compound was synthesized from XXXIII (0.95 mmol, 450 mg) in a similar way as for XX. Yield 250 mg (43%). NMR (DMSO-d$_6$): δ9.15 (s, 2H); 8.92 (s, 2H); 8.66 (t, 1H); 7.94 (s, 1H); 7.80 (m, 4H); 7.64 (d, 1H); 7.50 (t, 1H); 7.25 (d, 2H); 5.30 (s, 2H); 4.22 (m, 1H); 3.64 (s, 3H); 3.57 (m, 2H); 2.95 (m, 2H); 1.60 (m, 2H); 1.28 (m, 2H); 0.80 (t, 3H).

N$^2$-1-butanesulfonyl-N$^3$-(3-(4-amidinophenyloxymethyl)benzoyl)-2,3-diaminopropionic acid TFA salt (XXXV). This compound was synthesized by saponification of XXXIV (50 mg) with NaOH in methanol and purification on reversed phase HPLC. Yield 30 mg. ESI (M+H)$^+$: Calcd. 477.2; Found 477.3.

Example 16

Methyl N$^2$-Cbz-N$^3$-Boc-L-2,3-diaminopropionate (XXII). To a solution of V (13.9 mmol, 4 g) and di-tert-butyl dicarbonate (13.9 mmol, 3.03 g) in 30 mL THF cooled in an ice bath was added triethylamine (15 mmol, 2.1 mL) and the solution was stirred for 4 hours. Dilute citric acid solution was added followed by ethyl acetate. The organic layer was separated, washed with dilute citric acid, brine, NaHCO$_3$ and brine, dried (MgSO$_4$), and concentrated. Crystallization from ether-petroleum ether gave 4.68 g (96%) crystalline product. NMR (DMSO-d$_6$): δ7.60 (d, 1H); 7.35 (m, 5H); 6.88 (t, 1H); 5.02 (s, 2H); 4.14 (m, 1H); 3.60 (s, 3H); 3.28 (m, 2H); 1.37 (s, 9H).

Methyl N$^3$-Boc-L-2,3-diaminopropionate HCl salt (XXIII). A mixture of XXII (12.2 mmol, 4.32 g), concentrated HCl (14.7 mmol, 0.87 mL) and 10% Pd/C (432 mg) in 30 mL methanol was hydrogenated at atmospheric pressure for 4 hours. The catalyst was filtered off and the solution was concentrated. Ether was added and the solid was filtered, washed with ether to give 2.46 g (80%) product. NMR (DMSO-d$_6$): δ8.55 (b, 3H); 7.13 (t, 1H); 3.96 (m, 1H); 3.70 (s, 3H); 3.44 (m, 2H); 1.38 (s, 9H).

Methyl N$^2$-p-toluenesulfonyl-N$^3$-Boc-L-2,3-diaminopropionate (XXIV). To a solution of XXIII (3 mmol, 767 mg) in 10 mL THF was added p-toluenesulfonyl chloride (3 mmol, 572 mg) followed by triethylamine (7 mmol, 0.98 mL) and the solution was stirred for 4 hours. Ethyl acetate was added and the solution was washed with dilute citric acid, brine, NaHCO$_3$ and brine, dried (MgSO$_4$), and concentrated. crystallization from ether-petroleum ether gave 890 mg (79%) product. NMR (DMSO-d$_6$): δ8.20 (d, 1H); 7.64 (d, 2H); 7.38 (d, 2H); 6.84 (t, 1H); 3.90 (m, 1H); 3.38 (s, 3H); 3.10 (m, 2H); 2.39 (s, 3H); 1.32 (s, 9H).

Methyl N$^2$-p-toluenesulfonyl-L-2,3-diaminopropionate TFA salt (XXV). XXIV (2.37 mmol, 880 mg) was treated with 10 mL 60% TFA in methylene chloride for 1 hour and the solution was concentrated. The residue was triturated with ether-petroleum ether to give 700 mg (76%) product. NMR (DMSO-d$_6$): δ8.52 (d, 1H); 8.08 (b, 3H); 7.66 (d, 2H); 7.40 (d, 2H); 4.16 (m, 1H); 3.36 (s, 3H); 3.10 (m, 1H); 2.90 (m, 1H); 2.38 (s, 3H).

Methyl N$^2$-p-toluenesulfonyl-N$^3$-(3-chloromethylbenzoyl)-L-2,3-diaminopropionate (XXVI). This compound was synthesized in a similar was as for I from 3-chloromethylbenzoyl chloride (1.5 mmol, 0.21 mL), XXV (1.6 mmol, 621 mg) and triethylamine (3.5 mmol, 0.49 mL). Yield 638 mg (100%). NMR (DMSO-d$_6$): δ8.56 (t, 1H); 8.35 (d, 1H); 7.80 (s, 1H); 7.62 (m, 4H); 7.46 (t, 1H); 7.26 (d, 2H); 4.80 (s, 2H); 4.08 (m, 1H); 3.50 (m, 2H); 3.40 (s, 3H); 2.30 (s, 3H).

Methyl N$^2$-p-toluenesulfonyl-N$^3$-(3-cyanophenyloxymethyl)benzoyl)-L-2,3-diaminopropionate (XXVII). This compound was synthesized in a similar way as for II from XXVI (1.5 mmol, 637 mg), 4-cyanophenol (1.5 mmol, 179 mg) and potassium carbonate (3 mmol, 415 mg). Purification on a silica gel column using ethyl acetate/hexane gave 340 mg (45%) solid product. NMR (DMSO-d$_6$): δ8.56 (t, 1H); 8.35 (d, 1H); 7.84 (s, 1H); 7.80 (d, 2H); 7.70 (d, 1H); 7.61 (m, 3H); 7.50 (t, 1H); 7.28 (d, 2H); 7.20 (d, 2H); 5.26 (s, 2H); 4.06 (m, 1H); 3.50 (m, 2H); 3.38 (m, 1H); 3.39 (s, 3H); 2.30 (s, 3H).

Methyl N$^2$-p-toluenesulfonyl-N$^3$-(3-(4-amidinophenyloxymethyl)benzoyl)-L-2,3-diaminopropionate TFA salt (XXVIII). This compound was synthesized from XVII (0.63 mmol, 320 mg) using the similar procedure as for XX. Purification on reversed phase HPLC gave 125 mg (31%) product. NMR (DMSO-d$_6$): δ9.14 (s, 2H); 8.94 (s, 2H); 8.59 (t, 1H); 8.35 (d, 1H); 7.86 (s, 1H); 7.81 (d, 2H); 7.70 (d, 1H); 7.60 (m, 3H); 7.50 (t, 1H); 7.28 (d, 2H); 7.25 (d, 2H); 5.30 (s, 2H); 4.08 (m, 1H); 3.44 (m, 2H); 3.38 (s, 3H); 2.30 (s, 3H).

N$^2$-p-toluenesulfonyl-N$^3$-(3-(4-amidinophenyloxymethyl)benzoyl)-L-2,3-diaminopropionic acid TFA salt (XXIX). This compound was synthesized by saponification of XXVIII with NaOH in methanol and then purification on reversed phase HPLC. ESI (M+H)$^+$: Calcd. 511.2; Found 511.2.

Example 19a

Methyl-N$^2$-nicotinoyl-N$^3$-[3-(4-amidinophenyloxymethyl)benzoyl]-L-2,3-diaminopropionate TFA salt Methyl-N$^2$-tertbutyloxycarbonyl)-N$^3$-[3-(4-amidinophenyloxymethyl)-benzoyl]-L-2,3-diaminopropionate (25 mg, 0.043 mmol) was dissolved in 300 mL of trifluoroacetic acid and stirred at room temperature for 5 minutes. Cold diethyl ether was added to the reaction mixture and a white precipitate formed. The supernatant was removed and the precipitate was washed with diethyl ether and dried. To this material was added nicotinic acid (5.25 mg, 0.043 mmol), HBTU (16.3 mg, 0.043 mmol) and 300 mL of DMF. N-methylmorpholine (9.5 mL, 0.086 mmol) was then added to adjust the pH to 8–9. The reaction mixture was stirred at room temperature and monitored by HPLC until complete. The sample was then diluted with H$_2$O and purified directly by reversed-phase HPLC (preparative Vydac C18 column (2.5 cm), 0.45%/min gradient of 9 to 27% acetonitrile containing 0.1% trifluoroacetic acid) to afford the title compound as the di-trifluoroacetate salt. (9.72 mg, 32.1%) Mass spec (ESI): 476.2

Example 27

Benzyl N-(3-chloromethylbenzoyl)-3-aminopropionate (XVIII). This compound was synthesized in a similar way as for I from 3-chloromethylbenzoyl chloride (3 mmol, 426 mL), benzyl 3-aminopropionate toluenesulfonic acid salt (3.2 mmol, 1.12 g) and triethylamine (7 mmol, 0.98 mL). Crystallization from ether-petroleum ether gave 1.0 g (100%) product. NMR (DMSO-d$_6$): δ8.62 (t, 1H); 7.88 (s, 1H); 7.78 (d, 1H); 7.46 (t, 1H); 7.32 (m, 5H); 5.10 (s, 2H); 4.80 (s, 2H); 3.52 (m, 2H); 3.65 (t, 2H).

Benzyl N-(3-(4-cyanophenyloxymethyl)benzoyl)-3-aminopropionate (XIX) A mixture of XVIII (2.5 mmol, 829 mg), 4-cyanophenol (2.5 mmol, 298 mg) and potassium carbonate (5 mmol, 691 mg) in 15 mL DMF was stirred at 80° C. for 5 hours and then cooled to room temperature. The same work-up as for II and crystallization from ether-petroleum ether gave 1 g (97%) crystalline product. NMR (DMSO-$d_6$): δ8.62 (t, 1H); 7.92 (s, 1H); 7.80 (d, 2H); 7.78 (d, 1H); 7.62 (d, 1H); 7.50 (t, 1H); 7.32 (m, 5H); 7.20 (d, 2H); 5.24 (s, 2H); 5.10 (s, 2H); 3.52 (m, 2H); 2.66 (t, 2H).

Methyl N-(3-(4-amidinophenyloxymethyl) benzoyl)-3-aminopropionate TFA salt (XX). XIX (2 mmol, 830 mg) was dissolved in 20 mL methanol and HCl gas was bubbled through for 1 hour. The solution was stirred for 1 hour and then concentrated. The residue was taken up in 20 mL 2M ammonia in methanol and the solution was stirred for 5 hours and then concentrated. The residue was taken up in methanol and water. The solution was filtered and purified on reversed phase HPLC to give 650 mg (69%) product. NMR (DMSO-$d_6$): δ9.18 (s, 2H); 8.90 (s, 2H); 8.62 (t, 1H); 7.85 (s, 1H); 7.82 (d, 2H); 7.80 (d, 1H); 7.61 (d, 1H); 7.50 (t, 3H); 7.24 (d, 2H); 5.30 (s, 2H); 3.60 (s, 3H); 3.50 (m, 2H); 2.60 (t, 2H).

N-(3-(4-amidinophenyloxymethyl)benzoyl)-3-aminopropionic acid TFA salt (XXI). XX (0.21 mmol, 100 mg) was dissolved in 2 mL methanol and 2 mL 1N NaOH and after 1 hour the solution was acidified with TFA to pH 3. Purification on reversed phase HPLC gave 85 mg (88%) product. ESI (M+H)$^+$: Calc. 342.2; Found 342.2.

Example 53 (=Example 1)

Methyl $N^2$-Cbz-L-2,3-diaminopropionate HCl salt (V). $N^2$-Cbz-L-2,3-diaminopropionic acid (10 mmol, 2.39 g) was dissolved in 20 mL methanol and 20 mL 4N HCl in dioxane and the solution was stirred for 2 hours and then concentrated to give 2.74 g (95%) solid product. NMR (DMSO-$d_6$): δ8.38 (b, 3H); 7.96 (d, 1H); 7.38 (m, 5H); 5.05 (s, 2H); 4.44 (m, 1H); 3.66 (s, 3H); 3.14 (m, 2H).

Methyl $N^2$-Cbz-$N^3$-(3-chloromethylbenzoyl)-L-2,3-diaminopropionate (VI). To a solution of 3-chloromethylbenzoyl chloride (5 mmol, 0.71 mL) and V (5.3 mmol, 1.53 g) in 20 mL chloroform cooled in an ice bath was added triethylamine (11 mmol, 1.53 mL). The solution was stirred for 3 hours and then concentrated. The residue was taken up in ethyl acetate and the solution was washed with citric acid, brine, sodium bicarbonate and brine, dried (MgSO$_4$), and concentrated to give 2.1 g (100%) oily crude product. NMR (DMSO-$d_6$): δ8.62 (t, 1H); 7.86 (s, 1H); 7.79 (d, 1H); 7.60 (d, 1H); 7.48 (t, 1H); 7.34 (m, 5H); 5.02 (s, 2H); 4.82 (s, 2H); 4.35(m, 1H); 3.62 (s, 3H); 3.55 (m, 2H).

Methyl $N^2$-Cbz-$N^3$-(3-(4-cyanophenyloxymethyl) benzoyl)-L-2,3-diaminopropioate (VII). A solution of VI (5 mmol, 2.0 g), 4-cyanophenol (5 mmol, 596 mg) and potassium carbonate (8 mmol, 1.1 g) in 10 mL DMF was heated at 80° C. for 16 hours and then cooled to room temperature. Dilute citric acid solution was added followed by ethyl acetate. The organic layer was separated, washed with citric acid, brine, sodium bicarbonate and brine, dried (MgSO$_4$), and concentrated. Purification on a silica gel column using ethyl acetate/hexane gave 1.35 g (55%) pure product. NMR (DMSO-$d_6$): δ8.61 (t, 1H); 7.91 (s, 1H); 7.80 (d, 2H); 7.78 (d, 1H); 7.62 (d, 1H); 7.52 (t, 1H); 7.34 (m, 5H); 7.20 (d, 2H); 5.25 (s, 2H); 5.02 (s, 2H); 4.34 (m, 1H); 3.61 (s, 3H); 3.60 (m, 2H).

Methyl $N^2$-Cbz -$N^3$-(3-(4-amidinophenyloxymethyl) benzoyl)-L-2,3-diaminopropionate TFA salt (VIII). VII (2 mmol, 975 mg) was dissolved in 20 mL methanol and 20 ml 4N HCl in dioxane and the solution was stirred for 36 hours and then concentrated. The residue was taken up in 30 mL 2M ammonia in methanol and the solution was stirred for one day. Insoluble material was filtered off and the solution was concentrated. The residue was taken up in DMF and water and the solution was purified by reversed phase HPLC to give 150 mg pure product. NMR (DMSO-$d_6$): δ9.15 (s, 2H); 8.92 (s, 2H); 7.9.1 (s, 1H); 7.80 (d, 2H); 7.78 (d, 1H); 7.62 (d, 1H); 7.52 (t, 1H); 7.34 (m, 5H); 7.22 (d, 2H); 5.30 (s, 2H); 5.02 (s, 2H); 4.35 (m, 1H); 3.61 (s, 3H); 3.60 (m, 2H).

$N^2$-Cbz -$N^3$-(3-(4-amidinophenyloxymethyl)benzoyl)-L-2,3-diaminopropionic acid TFA salt (IX). VIII (50 mg) was dissolved in 2 mL methanol and 2 mL 1N NaOH and after One hour, the solution was acidified with HCl-Purification on reversed phase HPLC gave 30 mg product. ESI (M+H)$^+$: Calcd 491.2; Found 491.2.

Example 72a 1-t-butoxycarbonyl-4-hydroxypiperidine

A solution of 4-hydroxypiperidine (5.05 g; 0.05 mole) in 100 ml of tetrahydrofuran was stirred and cooled in an ice-water bath. Di-tert.butylcarbonate (10.9 g; 0.05 mole) was added and stirring was continued at room temperature for 3 hrs. The solvent was removed under reduced pressure. An oily residue was triturated with petroleum ether. Recrystallization from petroleum ether yielded 9.21 g (92%)-Rf (silica gel)=0.42 (ethyl acetate/n-hexane 1:9).

Ethyl 3-(N-BOC-piperidinooxymethyl)benzoate

N-Boc-4-hydroxypiperidine (1.98 g; 0.01 mole) was dissolved in 10 ml of dimethylformamide and cooled in a 0° C. ice bath. To this mixture sodium hydride, 60% suspension in an oil (0.6 g; 0.015 mole) was added an argon was passed through the reaction flask. The mixture was stirred 60 min. in the ice bath (under an argon atmosphere) before adding ethyl-3-(chloromethyl) benzoate. The reaction mixture was stirred at room temp. for 48 hrs and reaction was quenched with 30 ml of ethyl alcohol. The solvents were removed under reduced pressure. The residue was dissolved in ethyl acetate and extracted with 5% citric acid, brine and water. An organic fraction was dried over anhydrous magnesium sulfate, This material was further purified by flash chromatography (silica gel) using chloroform to give the title compound (B). Rf=0.29 (Ethyl acetate/n-hexane 2:8) (M+1) =363

3-(BOC-piperidinooxymethyl)benzoic acid

To a solution of ethyl 3-(Boc-piperidinooxymethyl) benzoate (0.7 g; 0.0019 mole) in ethanol (40 ml), cooled to 0° C. in an ice bath wag added a solution of sodium hydroxide (24 ml; 1N). After 2 hrs the reaction mixture was reduced to ½ of starting volume, pH adjusted to 3 with HCl and the solvent removed under reduced pressure. The white precipitate (NaCl) formed upon the addition of the ethanol to the dry residue was filtered off. The filtrate was concentrate under reduced pressure to the colorless oil. This material was taken to the next step of synthesis without further purification. Yield: 0.58 g (89.2%) Rf=0.65 Chloroform/methanol 9:1

Ethyl $N^3$-[3-(BOC-piperidinooxymethyl)benzoyl]-$N^2$-Cbz-2,3-diaminopropionate To a solution of 3-(BOC-piperidinooxymethyl)benzoic acid (0.56 g; 0.0016 mole) and $N^3$Cbz-L-2,3diaminopropionic acid hydrochloride (0.5 g; 0.0016 mole) in 5 ml dimethylforamide was added diisopropyl-ethyl amine (0.81 ml; 0.0046 mole). The mixture was stirred 10 min. and HBTU [2-(1H-benzotriazol-1-yl)-1,1,3,3-tetramethyluroniumhexafluorophosphate] (0.56 g; 0.0016 mole) was added as a coupling reagent. The reaction was allowed to proceed overnight at room temperature with stirring. The solvent was evaporated under reduced pressure, the residue was dissolved in 100 ml ethyl acetate. This solution was extracted with 5% citric acid, sat. $NaCO_3$ and brine. The organic layer was dried over anhydrous magnesium sulfate, filtered off and the solvent was evaporated under reduced pressure. This material was taken to the next step of synthesis without further purification. Yield: 0.91 g (95.7%) Rf=0.48 Choroform/methanol 95:5 (M+Na)=606

Ethyl $N^3$-[3-(piperidinooxymethyl)benzoyl]-$N^2$-Cbz-2,3-diaminopropionate

Ethyl $N^3$-[3-(Boc-piperidinooxymethyl)benzoyl)-L-$N^2$-Cbz-2,3-diaminopropionate) 0.9 g was dissolved in 100 ml 35% trifluoroacetic acid/methylene chloride and 10% of an anisole. The reaction at room temp. was allowed to proceed for 30 min. The progress of reaction was followed by TLC (silica gel; chloroform/methanol 95:%). The solvent was evaporated under reduced pressure and the residue was triturated with ethyl ether (3X). The new compound gave a positive Ninhydrin test and was taken to the next step of the synthesis.

Ethyl $N^3$-[3-(1-amidinopiperidinooxymethyl)benzoyl]-$N^2$-Cbz -2,3-diaminopropionate, TFA salt To a solution of ethyl $N^3$-[3-(piperidinooxymethyl)benzoyl]-L-$N^2$-Cbz-2,3-di-aminopropionate (0.06 g; 0.0001 mole) and dimethylaminopyridine (0.02 g; 0.0002 mole) in 1 ml ethanol/water (3:1) was added formamidine sulfonic acid. The progress of reaction was followed HPLC (Vydac C-18 analytical from 10% to 70% buffer B; 1% per min. Buffer A: 99.9% water 0.1% TFA Buffer B: 90.9% acetonitrile,9.9% water, 0.1%TFA). The reaction was allowed to proceed overnight. Purification was accomplished by HPLC on a preparative Vydac C-18 column (the same program as above) and than lyophilized to give TFA salt of the title compound. (M+1)=526.

Example 84b 3-(Piperidin-4-yl)propan-1-ol p-toluenesulfonate: To a solution of 3-(4-pyridyl)propan-1-ol (15.13 g, 0.1103 mol) in EtOH (100 mL) was added p-TsOH (20.98 g, 0.1103 mol) and $PtO_2$ (1.5 g, 6.6 mmol). The resulting mixture was placed on a Parr apparatus and hydrogenated at 55 p.s.i. After 6 hr, the mixture was filtered (EtOH wash) and the filtrate concentrated in vacuo, giving 36.78 g (>100%) of the desired piperidine; $^1$H NMR (300 MHz, $CDCl_3$) δ7.7 (d, 2H), 7.2 (d, 2H), 3.55 (t, 2H), 3.3 (m, 4H), 2.95 (bt, 2H), 2.38 (s, 3H), 1.95 (bd, 2H), 1.58 (m, 2H), 1.3 (m, 3H).

3-(N-t-Butyloxycarbonylpiperidin-4-yl)propan-1-ol: To a mixture of 3-(piperidin-4-yl)propan-1-ol p-toluenesulfonate (19.0 g, 57 mmol) in 2M NaOH (40 mL, 80 mmol) and t-BuOH (50 mL) was added di-tert-butyl dicarbonate (13.7 g, 62.7 mmol). After stirring for 18 hr, it was concentrated in vacuo and water added. The aqueous was extracted with ether (4 x) and the ethereal phase washed with saturated $Na_2CO_3$, saturated NaCl and dried ($MgSO_4$). Concentration in vacuo, then under vacuum afforded 11.37 g (82%) of the title compound; $^1$H NMR (300 MHz, $CDCl_3$) δ4.05 (bs, 2H), 3.63 (b, 2H), 2.7 (bt, 2H), 1.6 (m, 5H), 1.45 (s, 9H), 1.3 (m, 3H), 1.1 (m, 2H).

Methyl 4-[3-(N-t-butyloxycarbonylpiperidin-4-yl)propyl-1-oxy]benzoate: To a solution of 3-(N-t-butyloxycarbonylpiperidin-4-yl) propan-1-ol (6.08 g, 25.0 mmol), methyl 4-hydroxybenzoate (4.11 g, 27.0 mmol) and $PPh_3$ (9.18 g, 35.0 mmol) in THF (180 mL) at −10° C. was added a solution of DEAD (6.09 g, 35.0 mmol) in THF (30 mL) over 1.25 hr. During the addition, a deep red solution resulted, which changed to a golden color upon warming to room temperature overnight (18 hours). At this time the solution was concentrated and redissolved in EtOAc. It was then washed with water, 0.1M HCl, 1M NaOH, sat. NaCl and dried ($MgSO_4$). Concentration gave a solid (~20 g), which was purified using flash chromatography (5–20% EtOAc/hexanes step gradient), affording 5.46 g (58%) of the desired ether after pumping to constant weight; mp 83.0°–83.9° C.

4-[3-(N-t-Butyloxycarbonylpiperidin-4-yl)propyl-1-oxy] benzoic acid: To a solution of methyl 4-[3-(N-t-butyloxycarbonylpiperidin-4-yl)propyl-1-oxy]benzoate (5.37 g, 14.2 mmol) in THF (70 mL) was added 0.5M LiOH (57 mL, 28.5 mmol) and the resulting mixture heated at reflux overnight (18 hr). After cooling to room temperature, the mixture was acidified to pH 4 using 1M HCl and extracted using ether. The ethereal layer was washed with saturated NaCl, dried ($MgSO_4$) and concentrated in vacuo followed by pumping under vacuum, giving 5.82 g (89%) of the title compound; CIMS: $(M+NH_4)^+$=381 (100%).

4-[3-(N-t-Butyloxycarbonylpiperidin-4-yl)propyl-1-oxy]-N-3-(ethoxycarbonyl)propylbenzamide: To a solution of 4-[3-(N-t-butyloxycarbonylpiperidin-4-yl)propyl-1-oxy] benzoic acid (727 mg, 2.00 mmol) in DMF (10 mL) was added $Et_3N$ (0.32 mL, 2.3 mmol) followed by TBTU (706 mg, 2.20 mmol). After 15 min, a mixture of β-alanine ethyl ester hydrochloride (338 mg, 2.70 mmol) and $Et_3N$ (0.38 mL, 2.2 mmol) in DMF (10 mL) was added and the resulting mixture stirred for 18 hr at room temperature. The mixture is then diluted with EtOAc, washed with water (4x), 1M HCl, saturated $NaHCO_3$, saturated NaCl and dried ($MgSO_4$). Concentration in vacuo then under vacuum afforded 695 mg (78%) of the desired amide; CIMS: $(M+NH_4)^+$=480 (100%).

4-[3-(N-t-Butyloxycarbonylpiperidin-4-yl)propyl-1-oxy]-N-3-carboxypropylbenzamide: To a solution of 4-[3-(N-t-butyloxycarbonylpiperidin-4-yl)propyl-1-oxy]-N-3-(ethoxycarbonyl)propylbenzamide (639 mg, 1.38 mmol) in THF (10 mL) was added 0.5M LiOH (6 mL, 3 mmol) and the resulting mixture heated at reflux for 5 min. It was then cooled to room temperature, and acidified to pH 4 using 0.1M HCl. The aqueous was washed with $CHCl_3$, and the combined extracts dried ($MgSO_4$) and concentrated in vacuo. Purification of the oily residue using flash chromatography (5% MeOH-$CHCl_3$) afforded 252 mg (42%) of the acid as a light yellow oil that solidified upon standing; mp 109.6°–110.5° C.

4-[3-(Piperidin-4-yl)propyl-1-oxy]-N-3-carboxypropylbenzamide, TFA salt: To a solution of 4-[3-(N-t-butyloxycarbonylpiperidin-4-yl)propyl-1-oxy]-N-3-carboxypropylbenzamide (250 mg, 1.38 mmol) in $CH_2Cl_2$ (5 mL) was added TFA (2 mL, 11.8 mmol) and the resulting solution allowed to stand at room temperature for 60 hr. The solvent was evaporated in vacuo and the residue triturated with ether, then with EtOAc, giving 187 mg (41%) of the title compound as a white powder; mp 172.1°–172.9° C.

Example 85

Benzyl N-(3-chloromethylbenzoyl)-DL-3-aminobutyrate (I).

To a solution of 3-chloromethylbenzoyl chloride (10 mmol, 1.42 mL) and benzyl DL-3-aminobutyrate toluenesulfonic acid salt (10.5 mmol, 3.84 g) in 30 mL chloroform cooled in an ice bath was added triethylamine (21 mmol, 2.93 mL) and the solution was stirred for 2 h and then concentrated. The residue was taken up in ethyl acetate and washed with dilute citric acid, brine, sodium bicarbonate and brine, dried (MgSO$_4$), and concentrated. Crystallization from ether-petroleum ether gave 2.9 g (84%) crystalline product. NMR (DMSO-d$_6$): δ8.41 (d, 1H); 7.88 (s, 1H); 7.78 (d, 1H); 7.59 (d, 1H), 7.48 (t, 1H); 7.32 (m, 5H); 5.06 (s, 2H); 4.80 (s, 2H); 4.42 (m, 1H); 2.62 (m, 2H); 1.20 (d, 3H).

Benzyl N-(3-(4-cyanophenyloxymethyl)benzoyl)-DL-3-aminobutyrate (II). A solution of I (5 mmol, 1.73 g), 4-cyanophenol (5 mmol, 596 mg), and potassium carbonate (10 mmol, 1.38 g) in 10 mL DMF was heated at 60° C. for 18 hours and then cooled to room temperature. Dilute citric acid solution was added followed by ethyl acetate. The organic phase was separated, washed with dilute citric acid, brine, sodium bicarbonate and brine, dried (MgSO$_4$), and concentrated to give 2.1 g (98%) solid product. NMR (DMSO-d$_6$): δ8.40 (d, 1H); 7.90 (s, 1H); 7.78 (m, 3H); 7.61 (d, 1H); 7.48 (t, 1H); 7.28 (m, 5H); 7.20 (d, 2H); 5.23 (s, 2H); 5.04 (s, 2H); 4.41 (m, 1H); 2.62 (m, 2H); 1.20 (d, 3H).

Methyl N-(3-(4-amidinophenyloxymethyl)benzoyl)-DL-3-aminobutyrate, TFA salt (III). II (2 mmol, 857 mg) was dissolved in 20 mL methanol and 20 mL 4N HCl in dioxane. The mixture was stirred for 24 hours and then concentrated. The residue was taken up in 20 mL 2M ammonia in methanol and the solution was stirred overnight and then concentrated. The residue was dissolved in DMF and the solution was filtered, diluted with water and purified on HPLC to give 100 mg product. NMR (DMSO-d$_6$): δ9.16 (s, 2H); 8.94 (s, 2H); 8.40 (d, 1H); 7.90 (s, 1H); 7.81 (d, 2H); 7.80 (d, 1H); 7.61 (d, 1H); 7.50 (t, 1H); 7.25 (d, 2H); 5.30 (s, 2H); 4.38 (m, 1H); 3.59 (s, 3H); 2.58 (m, 2H); 1.20 (d, 3H).

N-(3-(4-Amidinophenyloxymethyl)benzoyl)-DL-3-aminobutyric acid TFA salt (IV). III (40 mg) was dissolved in 1 mL methanol and 1 ml 1N NaOH and after 2 hours, the solution was acidified with HCl to pH 3. Purification on reversed phase HPLC gave 30 mg product. ESI (M+H)$^+$: Calcd 356.2; Found 356.2.

Example 91

Methyl 3-(4-cyanobenzyloxy)benzoate (X). A mixture of 4-cyanobenzyl bromide (40 mmol, 7.84 g), methyl 3-hydroxybenzoate (40 mmol, 6.08 g) and potassium carbonate (60 mmol, 8.29 g) in 50 mL DMF was stirred at 60° C. overnight and the solution was cooled to room temperature. To it was added dilute citric acid followed by ethyl acetate. The organic layer was separated, washed with brine, NaHCO$_3$ and brine, dried (MgSO$_4$), and concentrated to give a solid. The solid was washed with ether two times to give 6.2 g (60%) product. NMR (DMSO-d$_6$): δ7.88 (d,2H) ;7.66(d,2H);7.58 (m, 2H); 7.46 (t, 1H); 7.32 (dd, 1H); 5.30 (s, 2H); 3.84 (s, 3H).

3-(4-cyanobenzyloxy)benzoic acid (XI). X (21.3 mmol, 5.7 g) was dissolved in 50 mL methanol and 50 mL THF and to it was added 30 mL 1N NaOH. The solution was stirred for 5 hours and acidified with 1N HCl to give a solid. The solid was isolated by filtration and washed with water to give 5.4 g (100%) product. NMR (DMSO-d$_6$): δ7.88 (d, 2H); 7.68 (d, 2H); 7.58 (m, 2H); 7.43 (t, 1H); 7.30 (dd, 1H); 5.32 (s, 2H).

Benzyl N-(3-(4-cyanobenzyloxy)benzoyl)-DL-3-aminobutyrate (XII). To a solution of XI (4 mmol, 1.01 g) and benzyl DL-3-aminobutyrate toluenesulfonic acid salt (4.2 mmol, 1.53 g) in 10 mL DMF were added BOP (4.2 mmol, 1.53 g) and triethylamine (15 mmol, 2.1 mL) and the solution was stirred overnight. Dilute citric acid solution was added followed by ethyl acetate. The organic layer was separated, washed with dilute citric acid, brine, NaHCO$_3$ and brine, dried (MgSO$_4$), and concentrated to give 1.6 g (94%) oily product. NMR (DMSO-d$_6$): δ8.35 (d, 1H); 7.86 (d, 2H); 7.65 (d, 2H); 7.18–7.45 (m, 9H); 5.26 (s, 2H); 5.08 (s, 2H); 4.40 (m, 1H); 2.64 (m, 2H); 1.1S (d, 3H).

Methyl N-(3-(4-amidinobenzyloxy)benzoyl)-DL-3-aminobutyrate TFA salt (XIII). To a solution of XII (2 mmol, 857 mg) in 30 mL methanol was bubbled through with HCl gas for 1 hour and the solution was stirred for 20 hours and then concentrated. The residue was taken up in 30 mL methanol and ammonia gas was bubbled through for one hour. The mixture was stirred overnight and then concentrated at room temperature. The solid was washed with ether and dissolved in DMF and water. Purification on reversed phase HPLC gave 240 mg pure product. NMR (DMSO-d$_6$): δ9.30 (s, 2H); 9.02 (s, 2H); 8.31 (d, 1H); 7.82 (d, 2H); 7.68 (d, 2H); 7.18–7.45 (m, 4H); 5.30 (s, 2H); 4.34 (m, 1H); 3.58 (s, 3H); 2.58 (m, 2H); 1.18 (d, 3H).

N-(3-(4-amidinobenzyloxy)benzoyl)-DL-3-aminobutyric acid TFA salt (XIV). XIII (50 mg) was dissolved in 2 mL methanol and 2 mL 1N NaOH and after one hour, the solution was acidified with TFA to pH 3. Purification on reversed phase HPLC gave 40 mg product. ESI (M+H)$^+$: Calc. 356.2; Found 356.2.

Example 92

Methyl DL-3-amino-4,4,4-trifluorobutyrate HCl salt (XV). DL-3-Amino-4,4,4-trifluorobutyric acid (19.1 mmol, 3 g) was dissolved in 20 mL methanol and 20 mL 4N HCl in dioxane. The solution stood at room temperature overnight and then concentrated to give 4.2 g (100%) solid product. NMR (DMSO-d$_6$): δ9.58 (b, 3H); 4.50 (m, 1H); 3.68 (s, 3H); 3.02 (m, 2H).

Methyl N-(3-(4-cyanobenzyloxy)benzoyl)-DL-3-amino-4,4,4-trifluorobutyrate (XVI). This compound was synthesized in a similar way as for XII from XI (4 mmol, 1.01 g), XV (4.2 mmol, 872 mg), BOP (4.2 mmol, 1.86 g) and triethylamine (15 mmol, 2.1 mL). Purification on a silica gel column using ethyl acetate/hexane gave 720 mg (44%) product. NMR (DMSO-d$_6$): δ8.92 (d, 1H); 7.88 (d, 2H); 7.68(d, 2H); 7.5 (m, 3H); 7.24 (dd, 1H); 5.28 (s, 2H); 5.18 (m, 1H); 3.61 (s, 1H); 2.95 (d, 2H).

N-(3-(4-amidinobenzyloxy)benzoyl)-DL-3-amino-4,4,4-trifluorobutyric acid TFA salt (XVII). XVI (1.7 mmol, 700 mg) was dissolved in 20 mL methanol and HCl gas was bubbled through for 1 hour. The solution was stirred overnight and then concentrated. The residue was taken up in 20 mL methanol and ammonia gas was bubbled through for 1 hour. The solution was stirred overnight and then concentrated. The major product from this reaction was isolated and characterized by NMR to be N-(3-(4-amidinobenzyloxy)benzoyl)-DL-3-amino-4,4,4-trifluorobutyramide. The small amount of the desired product was isolated by reversed phase HPLC and then saponified with NaOH in methanol to give the title compound. NMR (DMSO-d$_6$): δ9.32 (s, 2H); 9.12 (s, 2H); 8.88 (d, 1H); 7.84 (d, 2H); 7.70 (d, 2H); 7.48 (m, 3H); 7.24 (d, 1H); 5.32 (s, 2H); 5.12 (m, 1H); 2.82 (d, 2H). ESI (M+H)$^+$: Calc. 410.2; Found 410.2.

Example 117

Methyl N$^3$-(3-(4-amidinophenyloxymethyl)benzoyl)-L-2,3-diaminopropionate di-HCl salt (XXXVI). VII (22.5 mmol, 11 g) was dissolved in 100 mL methanol and HCl gas was bubbled through for 1 hour. The solution was stirred overnight and concentrated to give a solid. The solid was dissolved in 100 mL methanol and ammonia gas was bubbled through at 0° C. for 30 min. The solution was stirred for 1 hour and concentrated to give 12 g crude product which was used for the next reaction without purification.

$N^3$-(3-(4-amidinophenyloxymethyl)benzoyl)-L-2,3-diaminopropionic acid di-TFA salt (XXXVII). XXXVI (100 mg) was purified on reversed phase HPLC to give 20 mg pure product. The product was treated with 1 mL methanol and 0.5 mL 1N NaOH for 1 hour and then acidified with acetic acid. Purification on reversed phase HPLC gave 15 mg pure product.

Example 118

Ethyl $N^2$-Cbz-L-2,3-diaminopropionate HCl salt (XXXXII). This compound was synthesized from $N^2$-Cbz-L-2,3-diaminopropionic acid (10 mmol, 2.4 g) in a similar way as for V. Yield 2.67 g (88%). NMR (DMSO-$d_6$): δ8.42 (b, 3H); 7,96 (d, 1H); 7.36 (m, 5H); 5.08 (s, 2H); 4.44 (m, 1H); 4.13 (q, 2H); 3.20 (m, 1H); 3.08 (m, 1H); 1.18 (t, 3H).

Ethyl $N^2$-Cbz-$N^3$-(3-chloromethylbenzoyl)-L-2,3-diaminopropionate (XXXXIII). This compound was synthesized in a similar way as for VI from XXXXII (8.8 mmol, 2.67 g), 3-chloromethylbenzoyl chloride (9.8 mmol, 1.39 mL) and triethylamine (12 mmol, 1.67 mL). Crystallization from ether-petroleum ether gave 2.26 g (61%) product. NMR (DMSO-$d_6$): δ8.61 (t, 1H); 7.87 (s, 1H); 7.77 (m, 2H); 7.60 (d, 1H); 7.48 (t, 1H); 7.34 (m, 5H); 5.04 (s, 2H); 4.81 (s, 2H); 4.32 (m, 1H); 4.05 (q, 2H); 3.61 (m, 2H); 1.12 (t, 3H).

Ethyl $N^2$-Cbz-$N^3$-(3-(4-cyanophenyloxymethyl)benzoyl)-L-2,3-diaminopropionate (XXXXIV). This compound was synthesized in a similar way as for VII from XXXXIII (5 mmol, 2.09 g), 4-cyanophenol (5 mmol, 596 mg) and potassium carbonate (10 mmol, 1.38 g). Yield 2.4 g (96%). NMR (DMSO-$d_6$): δ8.62 (t, 1H); 7.94 (s, 1H); 7.80 (m, 4H); 7.64 (d, 1H); 7.52 (t, 1H); 7.34 (m, 5H); 7.20 (d, 2H); 5.27 (s, 2H); 5.05 (s, 2H); 4.34 (m, 1H); 4.04 (q, 2H).; 3.64 (m, 2H); 1.12 (t, 3H).

Ethyl $N^3$-(3-(4-amidinophenyloxymethyl)benzoyl)-L-2,3-diaminopropionate di-HCl salt (XXXXV). This compound was made in a similar way as for XXXVI by treating XXXXIV (4.6 mmol, 2.3 g) with HCl in ethanol and then with ammonia in ethanol. Yield 2.6 g. The crude product was directly used for the next reaction without purification.

Ethyl $N^2$-butyryl-$N^3$-(3-(4-amidinophenyloxymethyl)benzoyl)-L-2,3-diaminopropionate TFA salt (XXXXVI). To a solution containing XXXXV (0.57 mmol, 400 mg) and NaHCO$_3$ (1.5 mmol, 120 mg) in 2 mL water, 2 mL acetonitrile and 1 mL DMF cooled in an ice bath was added butyryl chloride (0.8 mmol, 83 μL). The solution was stirred for 2 hours, filtered and acidified with TFA. Purification on reversed phase HPLC gave 80 mg pure product. NMR (DMSO-$d_6$): δ9.15 (s, 2H); 8.93 (s, 2H); 8.64 (t, 1H); 8.24 (d, 1H); 7.93 (s, 1H); 7.81 (d, 2H); 7.79 (d, 1H); 7.63 (d, 1H); 7.52 (t, 1H); 7.25 (d, 2H); 5.30 (s, 2H); 4.45 (m, 1H); 4.04 (q, 2H); 3.59 (m, 2H); 2.10 (t, 2H); 1.50 (m, 2H); 1.10 (t, 3H); 0.84 (t, 3H).

$N^2$-butyryl-$N^3$-(3-(4-amidinophenyloxymethyl)benzoyl)-L-2,3-diaminopropionic acid TFA salt (XXXXVII). This compound was obtained by treating XXXXVI (50 mg) with 2 mL methanol and 1 mL 1N NaOH and then purification on reversed phase HPLC. Yield 35 mg.

Example 119a

Methyl-$N^2$-3-pyridylacetoyl-$N^3$-[3-(4-amidinophenyloxymethyl)benzoyl]-L-2,3-diaminopropionate Methyl-$N^2$-tertbutyloxycarbonyl-$N^3$-[3-(4-amidinophenyloxymethyl)-benzoyl]-L-2,3-diaminopropionate (18.7 mg, 0.032 mmol) was dissolved in 200 mL of trifluoroacetic acid and stirred at room temperature for 5 minutes. Cold diethyl ether was added to the reaction mixture and a white precipitate formed. The supernatant was removed and the precipitate was washed with diethyl ether and dried. To this material was added 3-pyridylacetic acid hydrochoride (5.6 mg, 0.032 mmol), HBTU (12.1 mg, 0.032 mmol) and 250 mL of DMF. N-methylmorpholine (10.5 uL, 0.096 mmol) was then added to adjust the pH to 8–9. The reaction mix was stirred at room temperature and monitored by HPLC until complete. The sample was then diluted with H$_2$O and purified directly by reversed-phase HPLC (preparative Vydac C18 column (2.5 cm), 0.45%/min gradient of 9 to 27% acetonitrile containing 0.1% trifluoroacetic acid) to afford the title compound as the di-trifluoroacetate salt (7.9 mg, 34.4%) Mass spec (ESI): 490.1.

Example 123

$N^2$-n-butyloxycarbonyl-$N^3$-[3-(4-amidinobenzyloxy)-5-isoxazolecarbonyl)-L-2,3-diaminopropionate TFA salt. The compound of Example 142 (0.26 mmol, 150 mg) was dissolved in 2 mL methanol and 2 mL 1N NaOH and after 45 min, the solution was acidified with acetic acid. Purification on reversed phase HPLC gave 125 mg (86%) product. ESI (M+H)+: Calcd 448.2; Found 448.2.

Example 142

Methyl $N^2$-n-butyloxycarbonyl-$N^3$-[3-(4-amidinobenzyloxy)-5 isoxazolecarbonyl]-L-2,3-diaminopropionate TFA salt A. Methyl $N^2$-Cbz-$N^3$-Boc-L-2,3-diaminopropionate HCl salt $N^2$-Cbz-L-2,3 diaminopropionic acid (10 mmol, 2.39 g) was dissolved in 20 mL methanol and 20 mL 4N HCl in dioxane and the solution was stirred for 4 hours and then concentrated to give a solid. The solid was washed with ether several times to give 2.50 g (87%) product. NMR (DMSO-$d_6$): δ8.38 (b, 3H); 7.96 (d, 1H); 7.38 (m, 5H); 5.05 (s, 2H); 4.44 (m, 1H); 3.66 (s, 3H); 3.14 (m, 2H).

B. Methyl $N^2$-Cbz -$N^3$-Boc-L-2,3-diaminopropionate To a solution of the compound of Part A (16.3 mmol, 4.7 g) and di-tert-butyl dicarbonate (16.3 mmol, 3.56 g) in 30 mL chloroform cooled in an ice bath was added triethylamine (34 mmol, 4.7 mL) and the solution was stirred in the ice bath for 1 hour and at room temperature for 3 hours and concentrated. The residue was taken up in ethyl acetate and the solution was washed with dilute citric acid, brine, NaHCO$_4$ and brine, dried (MgSO$_4$), and concentrated. Crystallization from ether/petroleum ether gave 5.2 g (92%) product. NMR (DMSO-$d_6$): δ7.60 (d, 1H); 7.35 (m, 5H); 6.88 (t, 1H); 5.02 (s, 2H); 4.14 (m, 1H); 3.60 (s, 3H); 3.28 (m, 2H); 1.37 (s,9H).

C. Methyl $N^3$-Boc-L-2,3-diaminopropionate HCO$_2$H salt A mixture of the compound of Part B (14 mmo, 5.0 g), formic acid (42 mmol, 1.6 mL) and 10% Pd/C (500 mg) in 40 mL methanol was stirred at room temperature for 1 hour and filtered through a celite. The filtrate was concentrated and the residue was triturated with ether-petroleum ether to give 3.7 g (100%) solid product. NMR (DMSO-$d_6$):δ8.20 (s, 1H); 6.90 (t, 1H); 5.36 (b, 3H); 3.61 9s, 3H); 3.51 (t, 1H); 3.18 (t, 2H); 1.38 (s, 9H).

D. Methyl $N^2$-n-butyloxycarbonyl-$N^3$-Boc-L-2.3-diaminopropionate To a mixture of the compound of Part C (14 mmol, 3.7 g) and NaHCO$_3$ (40 mmol, 3.4 g) in 10 mL water and 10 mL THF cooled in an ice bath was added slowly n-butyl chloroformate (16 mmol, 2 mL) over 15 min. After stirring for 1 hour, ethyl acetate was added and the solution was washed with dilute citric acid, brine, NaHCO$_3$ and brine, dried (MgSO4), and concentrated to give 4.4 g. (100%) oily product. NMR (DMSO-d$_6$): δ7.37 (d, 1H); 6.84 (t, 1H); 4.10 (m, 1H); 3.96 (t, 2H); 3.60 (s, 3H); 3.26 (m, 2H); 1.52 (m, 2H); 1.38 (s, 9H); 1.36 (m, 2H); 0.88 (t, 3H).

E. Methyl N$^2$-butyloxycarbonyl-L-2,3-diaminopropionate TFA salt The compound of Part D (13.9 mmol, 4.4 g) was dissolved in 25 mL methylene chloride and 35 mL TFA and after 1 hour, the solution was concentrated to give an oily product. Yield 4.8 g (100%). NMR (DMSO-d$_6$): δ8.02 (b, 3H); 7.68 (d, 2H); 4.38 (m, 1H); 3.99 (t, 2H); 3.68 (s, 3H); 3.22 (m, 1H); 3.06 (m, 1H); 1.55 (m, 2H); δ0.34 (m, 2H); 0.89 (t, 3H).

F. Methyl 3-(4-cyanobenzyloxy)-5-isoxazolecarboxylate. A mixture of o-bromo-p-tolunitrile (18.8 mmol, 3.69 g), methyl 3-hydroxy-5-isoxazolecarboxylate (18.8 mmol, 2.69 g) and potassium carbonate (25 mmol, 3.5 g) was heated at 50° C. overnight. After cooling to room temperature, the solution was added to 1% citric acid and the precipitate was filtered, washed with water and cold ether several times and dried. Yield 4.2 g (87%). NMR (DMSO-d6): δ7.90 (d, 2H); 7.68 (d, 2H); 7.18 (s, 1H); 5.43 (s, 2H); 3.90 (s, 3H).

G. 3-(4-cyanobenzyloxy)-5-isoxazolecarboxylic acid. The compound of part F (15 mmol, 3.87 g) was dissolved in 20 mL THF and 30 mL methanol and to it was added 30 mL 1N NaOH. After stirring at room temperature for 1 hour, the solution was reduced to 50 mL by concentration at 25° C. and acidified with 1N HCl to pH 3. The precipitate was filtered, washed with water several times and dried. Crystallization from ethyl acetate/petroleum ether gave 3.9. g (87%) product. NMR (DMSO-d$_6$): δ7.90 (d, 2H); 7.68 (d, 2H); 7.02 (s, 1H); 5.42 (s, 2H).

H. Methyl N$^2$-n-butyloxycarbonyl-N$^3$-3-(cyanobenzyloxy)-5-carbonyl]-L -2,3-diaminopropionate. To a solution of the compound of part E (14 mmol, 4.8 g) and the compound of part G (14 mmol, 3.2 g) in 30 mL DMF was added triethylamine (45 mmol, 6.3 mL) followed by BOP (14 mmol, 6.2 g) and the solution was stirred at room temperature for 5 hours. Ethyl acetate was added and the solution was washed with dilute citric acid, brine, NaHCO3 and brine, dried (MgSO4), and concentrated. The solid was washed with cold ether to give 4.1 g (66%) product. NMR (DMSO-d$_6$): δ8.97 (t, 1H); 7.90 (d, 2H); 7.68 (d, 2H); 7.58 (d, 1H); 6.91 (s, 1H); 5.41 (s, 2H); 4.28 (m, 1H); 3.95 (t, 2H); 3.61 (s, 3H); 3.59 (m, 2H); 1.52 (m, 2H); 1.32 (m, 2H); 0.87 (t, 3H).

I. Methyl N$^2$-n-butyloxycarbonyl-N$^3$-amidinobenzyloxy)-5-isocazolecarbonyl]-L-2,3-diaminopropionate TFA salt. The compound of Part H (9.2 mmol, 9.2 g) was suspended in 60 mL methanol and to it was bubbled with HCl gas in an ice bath for 1 hour. The solution was stirred at room temperature overnight and concentrated. The residue was taken up in 50 mL methanol and ammonium carbonate (25 mmol, 2.4 g) was added. The mixture was stirred overnight and concentrated. Purification on reversed phase HPLC gave 3.45 g (65%) product. ESI (M+H)+: Calcd 462.2; Found 462.3.

Example 479

(A). Methyl 3-(N-Boc-4-piperidinylmethoxy)-5-isoxazolecarboxylate. To a solution of piperidinylmethanol (15 mmol, 3.22 g), methyl 3-hydroxy-5-isoxazolecarboxylate (10 mmol, 1.43 g) and triphenyl phosphine (15 mmol, 3.93 g) in 20 mL THF was added diethyl azodicarboxylate (15 mmol, 2.36 g) and the solution was stirred overnight. The solution was reduced to a small amount by concentration and purification on silica gel column using 25% ethyl acetate/petroleum ether gave 1.88 g (40%) product. NMR (DMSO-d$_6$): δ7.08 (s, 1H); 4.12 (d, 2H); 3.97 (m, 2H); 3.88 (s, 3H); 2.72 (m, 2H); 1.96 (m, 1H); 1.70 (m, 2H); 1.40 (s, 9H); 1.14 (m, 2H).

B. 3-(N-Boc -4-piperidinylmethoxy)-5-isoxazolecarboxylic acid. The compound of Part A (5.5 mmol, 1.7 g) was dissolved in 10 mL methanol and 7 mL 1N NaOH and after 1 hour, the solution was acidified with 10% citric acid and extracted with ether. The ether layer was washed with brine, dried (MgSO$_4$), and concentrated to give 1.62 (100%) product. NMR (DMSO-d$_6$): δ6.94 (s, 1H); 4.10 (d, 2H); 3.97 (m, 2H); 2.72 (m, 2H); 1.96 (m, 1H); 1.70 (m, 2H); 1.39 (s, 9H); 1.14 (m, 2H).

C. Methyl N$^2$-n-butyloxycarbonyl-N$^3$-[3-(N-Boc-4-piperidinylmethoxy)-5-isoxazolecarbonyl]-L-2,3-diaminopropionate. To a solution of the compound of Part B (5.7 mmol, 1.7 g) and the compound of Example 142, Part E (6.84 mmol, 1.74 g) in 10 mL DMF cooled in an ice bath was added diisopropylethylamine (22.8 mmol, 3.97 mL) followed by BOP (6.27 mmol, 2.77 g). The mixture was stirred at room temperature overnight. Ethyl acetate was added and the solution was washed with 0.5N HCl, brine, NaHCO$_3$ and brine, dried (MgSO$_4$), and concentrated to give 2.8 g (98%) product. NMR (DMSO-d$_6$): δ8.92 (t, 1H); 7.56 (d, 1H); 6.81 (s, 1H); 4.27 (m, 1H); 4.10 (cl, 2H); 3.96 (m, 4H); 3.61 (s, 3H); 3.57 (m, 2H); 2.72 (m, 2H); 1.96 (m, 1H); 1.70 (m, 2H); 1.50 (m, 2H); 1.40 (s, 9H); 1.32 (m, 2H); 1.14 (m, 2H); 0.88 (t, 3H).

D. Methyl N$^2$-n-butyloxycarbonyl-N$^3$-[3-piperinylmethoxy)-5-isoxazolecarbonyl]-L-2,3-diaminopropionate TFA salt. The compound of part C (5.6 mmol, 2.8 g) was dissolved in 50 mL 60% TFA/methylene chloride and after 30 min, the solution was concentrated. Ether was added and no precipitation formed. The ether was removed and the residue was dried to give 3.3 g (>100%) product. NMR (DMSO-d$_6$): δ8.98 (t, 1H); 8.68 (b, 1H); 8.34 (b, 1H); 7.58 (d, 1H); 6.83 (s, 1H); 4.27 (m, 1H); 4.14 (d, 2H); 3.95 (t, 2H); 3.60 (s, 3H); 3.57 (m, 2H); 3.32 (m, 2H); 2.92 (m, 2H); 2.10 (m, 1H); 1.50 (m, 2H); 1.44 (M, 2H); 0.88 (t, 3H).

E. Methyl N$^2$-n-butyloxycarbonyl-N$^3$-[3-(N,N'-diCbzamidino-4-piperidinylinethoxy)-5-isoxazolecarbonyl]-L-2,3-diaminopropionate. A solution of the compound of Part D (2 mmol, 1.02 g), N,N'-diCbz-S-methylisothiourea (1.7 mmol, 585 mg) and 4-dimethylaminopyridine (2 mmol, 244 mg) in 6 mL DMF was stirred at room temperature for 2 days. Ethyl acetate was added and the solution was washed with 0.5N HCl, brine, NaHCO3 and brine, dried (MgSO$_4$), and concentrated. The crude product was purified on a silica gel column using ethyl acetate/hexane (2:3) to give 870 mg (63%) product. NMR (DMSO-d$_6$): δ10.08 (s, 1H); 8.92 (t, 1H); 7.57 (d, 1H); 7.35 (m, 10H); 6.82 (s, 1H); 5.08 (b, 2H); 4.94 (b, 2H); 4.26 (m, 1H); 4.12 (d, 2H); 4.08 (m, 2H); 3.95 (t, 2H); 3.61 (s, 3H); 3.57 (m, 2H); 2.92 (m, 2H); 2.06 (m, 1H); 1.76 (m, 211); 1.50 (m, 2H); 1.30 (m, 2H); 1.25 (m, 2H); 0.88 (t, 3H).

F. Methyl N$^2$-n-butyloxycarbonyl-N-[3-(N-amidino-4-piperidinylinethoxy)-5-isoxazolecarbonyl]-L -2,3-diaminopropionate TFA salt. A mixture of the compound of Part E (1.09 mmol, 800 mg), 10% Pd/C and methanesulfonic acid (2 mmol, 130 uL) in S mL DMF was hydrogenated at atmospheric pressure overnight. The catalyst was filtered off and the solution was diluted with water. Purification on reversed phase HPLC gave 325 mg (50%) product. NMR (DMSO-d$_6$): δ8.96 (t, 1H); 7.58 (d, 1H); 7.34 (s, 4H); 6.84 (s, 1H); 4.27 (m, 1H); 4.13 (d, 2H); 3.95 (t, 2H); 3.88 (m, 2H); 3.61 (s, 3H); 3.57 (m, 2H); 3.04 (m, 2H); 2.10 (m, 1H); 1.80 (m, 2H); 1.50 (m, 2H); 1.32 (m, 2H); 1.26 (m, 2H); 0.88 (t, 3H).

Utility

The compounds of this invention possess antiplatelet efficacy, as evienced by their activity in standard platelet aggregation assays or platelet fibrinogen binding assays, as described below. A compound is considered to be active in these assays if it has an IC$_{50}$ value of less than about 1 nM. Platelet aggregation and fibrinogen binding assays which may be used to demonstrate the antiplatelet activity of the compounds of the invention are described below.

Platelet Aggregation Assay: Venous blood was obtained from the arm of a healthy human donor who was drug-free and aspirin-free for at least two weeks prior to blood collection. Blood was collected into 10 mL citrated Vacutainer tubes. The blood was centrifuged for 15 minutes at 150 x g at room temperature, and platelet-rich plasma (PRP) was removed. The remaining blood was centrifuged for 15 minutes at 1500 x g at room temperature, and platelet-poor plasma (PPP) was removed. Samples were assayed on a aggregometer (PAP-4 Platelet Aggregation Profiler), using PRP as the blank (100% transmittance). 200 μL of PRP was added to each micro test tube, and transmittance was set to 0%. 20 μL of various agonists (ADP, collagen, arachidonate, epinephrine, thrombin) were added to each tube, and the aggregation profiles were plotted (% transmittance versus time). The results are expressed as % inhibition of agonist-induced platelet aggregation. For the IC$_{50}$ evaluation, the test compounds were added at various concentrations prior to the activation of the platelets.

Purified GPIIb/IIIa-Fibrinogen Binding ELISA

The following reagents are used in the GPIIb/IIIa-fibrinogen binding ELISA:

purified GPIIb/IIIa (148.8 ug/mL);

biotinylated fibrinogen (~1 mg/mL or 3000 nM);

anti-biotin alkaline phosphatase conjugate (Sigma no. A7418);

flat-bottom, high binding, 96-well plates (Costar Cat. no. 3590);

phosphatase substrate (Sigma 104) (40 mg capsules);

bovine serum albumin (BSA) (Sigma no. A3294);

Alkaline Phosphatase buffer –0.1M glycine-HCl, 1 mM MgCl$_2$.6H$_2$O, 1 mM ZnCl$_2$, pH 10.4;

Binding buffer 20 mM Tris-HCl, 150 mM NaCl, 1 mM CaCl$_2$.2H$_2$O, 0.02% NaN$_3$, pH 7.0;

Buffer A –50 mM Tris-HCl, 100 mM NaCl, 2 mM CaCl$_2$.2H$_2$O, 0.02% NAN$^3$, pH 7.4;

Buffer A+3.5% BSA (Blocking buffer);

Buffer A+0.1% BSA (Dilution buffer);

2N NaOH.

The following method steps are used in the GPIIb/IIIa-fibrinogen binding ELISA:

Coat plates with GPIIb/IIIa in Binding buffer (125 ng/100 uL/well) overnight at 4° C. (Leave first column uncoated for non-specific binding). Cover and freeze plates at –70° C. until used. Thaw plate 1 hour at room temperature or overnight at 4° C. Discard coating solution and wash once with 200 uL Binding buffer per well. Block plate 2 hours at room temperature on shaker with 200 ul Buffer A+3.5% BSA (Blocking buffer) per well. Discard Blocking buffer and wash once with 200 uL Buffer A+0.1% BSA (Dilution buffer) per well. Piper 11 uL of test compound (10X the concentration to be tested in Dilution buffer) into duplicate wells. Pipet 11 ul Dilution buffer into non-specific and total binding wells. Add 100 uL Biotinylated fibrinogen (1/133 in Dilution buffer, final concentration=20 nM) to each well. Incubate plates for 3 hours at room temperature on a plate shaker. Discard assay solution and wash twice with 300 uL Binding buffer per well. Add 100 uL Anti-biotin alkaline phosphatase conjugate (1/1500 in Dilution buffer) to each well. Incubate plates for 1 hour at room temperature on plate shaker. Discard conjugate and wash twice with 300 51 Binding buffer per well. Add 100 uL Phosphatase substrate (1.5 mg/ml in Alkaline phosphatase buffer) to each well. Incubate plate at room temperature on shaker until color develops. Stop color development by adding 25 uL 2N NaOH per well. Read plate at 405 nm. Blank against non-specific binding (NSB) well. % Inhibition is calculated as 100-(Test Compound Abs/Total Abs)x100.

Platelet-Fibrinogen Binding Assay: Binding of $^{125}$I-fibrinogen to platelets was performed as described by Bennett et al. (1983) Proc. Natl. Acad. Sci. USA 80: 2417–2422, with some modifications as described below. Human PRP (h-PRP) was applied to a Sepharose column for the purification of platelet fractions. Aliquots of platelets (5×10$^8$ cells) along with 1 mM calcium chloride were added to removable 96 well plates prior to the activation of the human gel purified platelets (h-GPP). Activation of the human gel purified platelets was achieved using ADP, collagen, arachidonate, epinephrine, and/or thrombin in the presence of the ligand, $^{125}$I-fibrinogen. The $^{125}$I-fibrinogen bound to the activated platelets was separated from the free form by centrifugation and then counted on a gamma counter. For an IC$_{50}$ evaluation, the test compounds were added at various concentrations prior to the activation of the platelets.

The compounds of Formula I of the present invention may also possess thrombolytic efficacy, that is, they are capable of lysing (breaking up) already formed platelet-rich fibrin blood clots, and thus are useful in treating a thrombus formation, as evidenced by their activity in the tests described below. Preferred compounds of the present invention for use in thrombolysis include those compounds having an IC$_{50}$ value (that is, the molar concentration of the compound capable of achieving 50% clot lysis) of less than about 1 mM, more preferably an IC$_{50}$ value of less than about 0.1 mM.

Thrombolytic Assay: Venous blood was obtained from the arm of a healthy human donor who was drug-free and aspirin free for at least two weeks prior to blood collection, and placed into 10 ml citrated Vacutainer tubes. The blood was centrifuged for 15 minutes at 1500 x g at room temperature, and platelet rich plasma (PRP) was removed. To the PRP was then added 1×10$^{-3}$M of the agonist ADP, epinephrine, collagen, arachidonate, serotonin or thrombin, or a mixture thereof, and the PRP incubated for 30 minutes. The PRP was centrifuged for 12 minutes at 2500 x g at room temperature. The supernatant was then poured off, and the platelets remaining in the test tube were resuspended in platelet poor plasma (PPP), which served as a plasminogen source. The suspension was then assayed on a Coulter Counter (Coulter Electronics, Inc., Hialeah, Fla.), to determine the platelet count at the zero time point. After obtaining the zero time point, test compounds were added at various concentrations. Test samples were taken at various time points and the platelets were counted using the Coulter Counter. To determine the percent of lysis, the platelet count at a time point subsequent to the addition of the test compound was subtracted from the platelet count at the zero time point, and the resulting number divided by the platelet count at the zero time point. Multiplying this result by 100 yielded the percentage of clot lysis achieved by the test compound. For the $IC_{50}$ evaluation, the test compounds were added at various concentrations, and the percentage of lysis caused by the test compounds was calculated.

The compounds of Formula I of the present invention are also useful for administration in combination with anticoagulant agents such as warfarin or heparin, or antiplatelet agents such as aspirin, piroxicam or ticlopidine, or thrombin inhibitors such as boropeptides, hirudin or argatroban, or thrombolytic agents such as tissue plasminogen activator, anistreplase, urokinase or streptokinase, or combinations thereof.

Table A below sets forth the biological activity of representative compounds of the present invention.

TABLE A

| Example Number | $IC_{50}$ |
| --- | --- |
| 85 | +++ |
| 53 | +++ |
| 110 | ++ |
| 91 | +++ |
| 92 | + |
| 27 | +++ |
| 16 | +++ |
| 16a | ++ |
| 6a | +++ |
| 3a | +++ |
| 14 | +++ |
| 18a | +++ |
| 19a | +++ |
| 20a | +++ |
| 84a | +++ |
| 84b | +++ |
| 119a | +++ |
| 123 | +++ |
| 142 | +++ |
| 479 | +++ |
| 480 | ++ |
| 481 | ++ |
| 482 | + |
| 500a | +++ |
| 501a | +++ |

In Table A the biological activity of the compounds is indicated as the $IC_{50}$ value in the platelet aggregation assay described above. The $IC_{50}$ values are expressed as: +++= $IC_{50}$ of <10 uM; ++=$IC_{50}$ value of 10 uM to 50 uM; +=$IC_{50}$ of 51–100 uM. As used herein "uM" means micromolar.

Dosage and Formulation

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiaggregation agent.

The compounds of this invention can be administered by any means that produces contact of the active agent with the agent's site of action, glycoprotein IIb/IIIa (GPIIb/IIIa), in the body of a mammal. They can be administered by any conventional means available for use in conjunction with pharmaceuticals, either as individual therapeutic agents or in a combination of therapeutic agents, such as a second antiplatelet agent such as aspirin or ticlopidine which are agonist-specific. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the Compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxybutyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension:

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent selected from: an anti-coagulant agent such as warfarin or heparin; an anti-platelet agent such as aspirin, piroxicam or ticlopidine; a thrombin inhibitor such as a boropeptide thrombin inhibitor, or hirudin; or a thrombolytic agent such as plasminogen activators, such as tissue plasminogen activator, anistreplase, urokinase or streptokinase. The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent (anti-coagulant agent, anti-platelet agent, thrombin inhibitor, and/or thrombolytic agent) may be administered essentially at the same time, or in any order; for example the compound of Formula I may be administered first, followed by administration of the second agent (anti-coagulant agent, anti-platelet agent, thrombin inhibitor, and/or thrombolytic agent). When not administered at the same time, preferably the administration of the compound of Formula and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent (anti-coagulant agent, anti-platelet agent, thrombin inhibitor, and/or thrombolytic agent) are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Although the proper dosage of the compound of Formula I when administered in combination with the second therapeutic agent will be readily ascertainable by a medical practitioner skilled in the art, once armed with the present disclosure, by way of general guidance, where the compounds of this invention are combined with anti-coagulant agents, for example, a daily dosage may be about 0.1 to 100 milligrams of the compound of Formula I and about 1 to 7.5 milligrams of the anti-coagulant, per kilogram of patient body weight. For a tablet dosage form, the novel compounds of this invention generally may be present in an amount of about 5 to 10 milligrams per dosage unit, and the anti-coagulant in an amount of about 1 to 5 milligrams per dosage unit.

Where the compounds of Formula I are administered in combination with a second anti-platelet agent, by way of general guidance, typically a daily dosage may be about 0.01 to 25 milligrams of the compound of Formula I and about 50 to 150 milligrams of the additional anti-platelet agent, preferably about 0.1 to 1 milligrams of the compound of Formula I and about 1 to 3 milligrams of antiplatelet agents, per kilogram of patient body weight.

Further, by way of general guidance, where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the inhibition of platelet aggregation, the treatment of blood clots, and/or the treatment of thromboembolic disorders, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

The Tables below provide representative compounds of Formula I of the present invention. Also specifically disclosed by the present invention are those compounds listed in the Tables below wherein $R^{16}$ is selected from:

$C_1$ to $C_{10}$ alkyl;
methylcarbonyloxymethyl-;
ethylcarbonyloxymethyl-;
t-butylcarbonyloxymethyl-;
cyclohexylcarbonyloxymethyl-;
1-(methylcarbonyloxy)ethyl-;
1-(ethylcarbonyloxy)ethyl-;
1-(t-butylcarbonyloxy)ethyl-;
1-(cyclohexylcarbonyloxy)ethyl-;
1-propyloxycarbonyloxymethyl-;
cyclohexylcarbonyloxymethyl-;
t-butyloxycarbonyloxymethyl-;
1-(i-propyloxycarbonyloxy)ethyl-;
1-(cyclohexyloxycarbonyloxy)ethyl-;
1-(t-butyloxycarbonyloxy)ethyl-;
dimethylaminoethyl-;

diethylaminoethyl -;
(1,3-dioxa-5-methyl-cyclopenten-2-one-4-yl)methyl-;
(5-(t-butyl)-1,3-dioxa-cyclopenten-2-one-4-yl)methyl-;
(1,3-dioxa-5-phenyl-cyclopenten-2-one-4-yl)methyl-;
1-(2-(2-methoxypropyl)carbonyloxy)ethyl-.

TABLE 1

| Example Number | R⁹ | R¹⁶ | FAB MS (M + H)⁺ |
|---|---|---|---|
| 1 | NHC(=O)OCH$_2$(C$_6$H$_5$) | H | 491.2 |
| 2 | NHC(=O)OC(CH$_3$)$_3$ | H | 471 |
| 3 | NHC(=O)O(CH$_2$)$_3$CH$_3$ | H | |
| 4 | NHC(=O)OCH$_2$CH$_3$ | H | |
| 5 | NHC(=O)OCH$_3$ | H | |
| 6 | NHC(=O)CH$_2$CH$_2$(C$_6$H$_5$) | H | |
| 7 | NHC(=O)CH$_2$C(CH$_3$)$_3$ | H | |
| 8 | NHC(=O)(CH$_2$)$_4$CH$_3$ | H | |
| 9 | NHC(=O)(CH$_2$)$_3$CH$_3$ | H | 455 |
| 10 | NHC(=O)CH$_2$CH$_3$ | H | |
| 11 | NHC(=O)—CH$_3$ | H | |
| 12 | NHS(=O)$_2$CH$_3$ | H | |
| 13 | NHS(=O)$_2$CH$_2$CH$_3$ | H | |
| 14 | NHS(=O)$_2$(CH$_2$)$_3$CH$_3$ | H | 477.2 |
| 15 | NHS(=O)$_2$(C$_6$H$_5$) | H | |
| 16 | NHS(=O)$_2$-4-(methyl)phenyl | H | 511.2 |
| 17 | NHS(=O)$_2$CH$_2$(C$_6$H$_5$) | H | |
| 18 | NHC(=O)-2-pyridyl | H | |
| 19 | NHC(=O)-3-pyridyl | H | 476 |
| 20 | NHC(=O)-4-pyridyl | H | |
| 21 | CH$_3$ | H | |
| 22 | CH$_2$CH$_3$ | H | |
| 23 | C$_6$H$_5$ | H | |
| 24 | 2-pyridyl | H | |
| 25 | 3-pyridyl | H | |
| 26 | 4-pyridyl | H | |
| 27 | H | H | 342.2 |
| 117 | NH$_2$ | H | |
| 118 | NHC(=O)O(CH$_2$)$_2$CH$_3$ | H | |
| 1a | NHC(=O)OCH$_2$(C$_6$H$_5$) | CH$_3$ | |
| 2a | NHC(=O)OC(CH$_3$)$_3$ | CH$_3$ | 471 |
| 3a | NHC(=O)O(CH$_2$)$_3$CH$_3$ | CH$_3$ | 471 |
| 4a | NHC(=O)OCH$_2$CH$_3$ | CH$_3$ | |
| 5a | NHC(=O)OCH$_3$ | CH$_3$ | |
| 6a | NHC(=O)CH$_2$CH$_2$(C$_6$H$_5$) | CH$_3$ | 503 |
| 7a | NHC(=O)CH$_2$C(CH$_3$)$_3$ | CH$_3$ | |
| 8a | NHC(=O)(CH$_2$)$_4$CH$_3$ | CH$_3$ | |
| 9a | NHC(=O)(CH$_2$)$_3$CH$_3$ | CH$_3$ | |
| 10a | NHC(=O)CH$_2$CH$_3$ | CH$_3$ | |
| 11a | NHC(=O)—CH$_3$ | CH$_3$ | |
| 12a | NHC(=O)$_2$CH$_3$ | CH$_3$ | |
| 13a | NHS(=O)$_2$CH$_2$CH$_3$ | CH$_3$ | |
| 14a | NHS(=O)$_2$(CH$_2$)$_3$CH$_3$ | CH$_3$ | |
| 15a | NHS(=O)$_2$(C$_6$H$_5$) | CH$_3$ | |
| 16a | NHS(=O)$_2$-4-(methyl)phenyl | CH$_3$ | 511.2 |
| 18a | NHC(=O)-2-pyridyl | CH$_3$ | 476.2 |
| 19a | NHC(=O)-3-pyridyl | CH$_3$ | 476 |
| 20a | NHC(=O)-4-pyridyl | CH$_3$ | 476.1 |
| 21a | CH$_3$ | CH$_3$ | |
| 22a | CH$_2$CH$_3$ | CH$_3$ | |
| 23a | C$_6$H$_5$ | CH$_3$ | |
| 24a | 2-pyridyl | CH$_3$ | |
| 25a | 3-pyridyl | CH$_3$ | |
| 26a | 4-pyridyl | CH$_3$ | |
| 27a | H | CH$_3$ | |
| 117a | NH$_2$ | CH$_3$ | |
| 118a | NHC(=O)O(CH$_2$)$_2$CH$_3$ | CH$_3$ | |
| 119a | NHC(=O)CH$_2$(3-pyridyl) | CH$_3$ | 490 |
| 500a | NHC(=O)CH$_2$(2-pyridyl) | CH$_3$ | 490.2 |
| 501a | NHC(=O)CH$_2$(4-pyridyl) | CH$_3$ | 490.3 |
| 3b | NHC(=O)(CH$_2$)$_3$CH$_3$ | C$_2$H$_5$ | 455 |

TABLE 2

| Example Number | R⁹ | FAB MS (M + H)⁺ |
|---|---|---|
| 28 | NHC(=O)OCH$_2$(C$_6$H$_5$) | |
| 29 | NHC(=O)OC(CH$_3$)$_3$ | |
| 30 | NHC(=O)O(CH$_2$)$_3$CH$_3$ | |
| 31 | NHC(=O)OCH$_2$CH$_3$ | |
| 32 | NHC(=O)OCH$_3$ | |
| 33 | NHC(=O)CH$_2$CH$_2$(C$_6$H$_5$) | |
| 34 | NHC(=O)CH$_2$C(CH$_3$)$_3$ | |
| 35 | NHC(=O)(CH$_2$)$_4$CH$_3$ | |
| 36 | NHC(=O)(CH$_2$)$_3$CH$_3$ | |
| 37 | NHC(=O)CH$_2$CH$_3$ | |
| 38 | NHC(=O)—CH$_3$ | |
| 39 | NHS(=O)$_2$CH$_3$ | |
| 40 | NHS(=O)$_2$CH$_2$CH$_3$ | |
| 41 | NHS(=O)$_2$(CH$_2$)$_3$CH$_3$ | |
| 42 | NHS(=O)$_2$(C$_6$H$_5$) | |
| 43 | NHS(=O)$_2$CH$_2$(C$_6$H$_5$) | |
| 44 | NHC(=O)-2-pyridyl | |
| 45 | NHC(=O)-3-pyridyl | |
| 46 | NHC(=O)-4-pyridyl | |
| 47 | CH$_3$ | |
| 48 | CH$_2$CH$_3$ | |
| 49 | C$_6$H$_5$ | |
| 50 | 2-pyridyl | |
| 51 | 3-pyridyl | |
| 52 | 4-pyridyl | |

TABLE 3

| Example Number | U | FAB MS (M + H)⁺ |
|---|---|---|
| 53 | OCH$_2$ | 491.2 |
| 54 | CH$_2$O | |
| 55 | SCH$_2$ | |
| 56 | CH$_2$S | |
| 57 | NHCH$_2$ | |
| 58 | CH$_2$NH | |
| 59 | N(CH$_3$)CH$_2$ | |
| 60 | CH$_2$N(CH$_3$) | |
| 61 | S(=O)CH$_2$ | |
| 62 | CH$_2$S(=O) | |
| 63 | S(=O)$_2$CH$_2$ | |
| 64 | CH$_2$S(=O)$_2$ | |
| 65 | S(=O)$_2$NH | |
| 66 | NHS(=O)$_2$ | |
| 67 | CH$_2$CH$_2$ | |
| 68 | CH=CH | |
| 69 | C≡C | |

TABLE 4
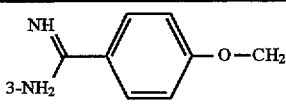
| Ex. No. | R¹—U | R⁹ | R¹⁶ | FAB MS (M + H)⁺ |
|---|---|---|---|---|
| 70 | 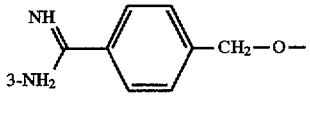 | NHCbz | H | |
| 71 | 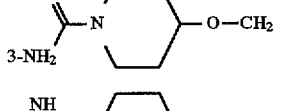 | NHCbz | H | |
| 72 | 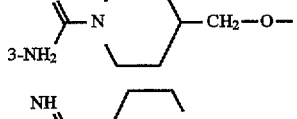 | NHCbz | H | |
| 73 | 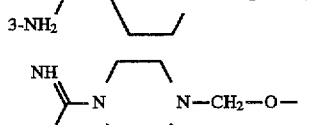 | NHCbz | H | |
| 74 | 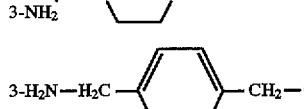 | NHCbz | H | |
| 75 | 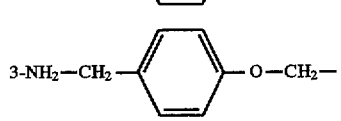 | NHCbz | H | |
| 76 | 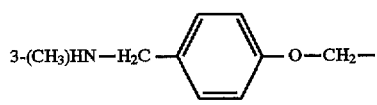 | NHCbz | H | |
| 77 | 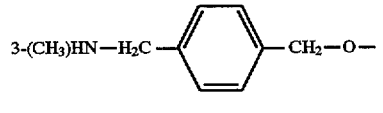 | NHCbz | H | |
| 78 | 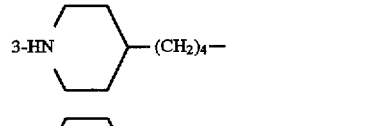 | NHCbz | H | |
| 79 | 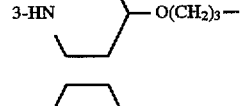 | NHCbz | H | |
| 80 | 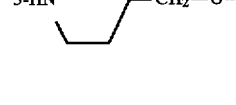 | NHCbz | H | |
| 81 |  | NHCbz | H | |
| 82 |  | NHCbz | H | |

TABLE 4-continued

Structure: R¹—U—(phenyl)—C(=O)—NH—CH(R⁹)—C(=O)—OR¹⁶

| Ex. No. | R¹—U | R⁹ | R¹⁶ | FAB MS (M + H)⁺ |
|---|---|---|---|---|
| 83 | 3-HN-piperidinyl—CH₂—CH₂—O—CH₂— | NHCbz | H | |
| 84 | 3-HN-piperidinyl—(CH₂)₃—O— | NHCbz | H | |
| 84a | 3-HN-piperidinyl—(CH₂)₃—O— | H | H | 335 |
| 84b | 4-HN-piperidinyl—(CH₂)₃—O— | H | H | 335 |
| 72a | N-(amidino)-piperidin-4-yl—O—CH₂— | NHCbz | CH₃ | 526 |
| 83a | HN-piperidinyl—CH₂—CH₂—O—CH₂— | NHCbz | CH₃ | 498 |
| 120b | HN-piperazinyl—N—CH₂—CH₂—O—CH₂— | NHCbz | C₂H₅ | 513 |

TABLE 4a

Structure: R¹—U—(phenyl)—C(=O)—W

| Ex. No. | R¹—U | W | FAB MS (M + H)⁺ |
|---|---|---|---|
| 480 | 4-HN-piperidinyl—(CH₂)₃—O— | piperidin-1-yl-2-CH₂COOH | 389 |
| 481 | 4-HN-piperidinyl—(CH₂)₃—O— | azepan-1-yl | 403 |
| 482 | 4-HN-piperidinyl—(CH₂)₂—O— | piperidin-1-yl-2-CH₂COOH | 375 |

TABLE 5

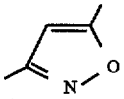

| Example Number | U | R⁸ | FAB MS (M + H)⁺ |
|---|---|---|---|
| 85 | $OCH_2$ | $CH_3$ | 356.2 |
| 86 | $OCH_2$ | $CF_3$ | |
| 87 | $OCH_2$ | $C_6H_5$ | |
| 88 | $OCH_2$ | 2-pyridyl | |
| 89 | $OCH_2$ | 3-pyridyl | |
| 90 | $OCH_2$ | 4-pyridyl | |
| 91 | $CH_2O$ | $CH_3$ | 356.2 |
| 92 | $OCH_2$ | $CF_3$ | 410.2 |
| 93 | $CH_2O$ | $C_5H_5$ | |
| 94 | $CH_2O$ | 2-pyridyl | |
| 95 | $CH_2O$ | 3-pyridyl | |
| 96 | $CH_2O$ | 4-pyridyl | |

TABLE 6

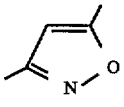

| Example Number | U | R⁹ | R⁸ | R¹⁶ | FAB MS (M + H)⁺ |
|---|---|---|---|---|---|
| 97 | $OCH_2$ | $CH_3$ | H | $CH_3$ | |
| 98 | $OCH_2$ | $CH_3$ | H | $CH_2CH_3$ | |
| 99 | $OCH_2$ | $C_6H_5$ | H | $CH_3$ | |
| 100 | $OCH_2$ | $C_6H_5$ | H | $CH_2CH_3$ | |
| 101 | $CH_2O$ | $CH_3$ | H | $CH_3$ | |
| 102 | $CH_2O$ | $CH_3$ | H | $CH_2CH_3$ | |
| 103 | $CH_2O$ | $C_6H_5$ | H | $CH_3$ | |
| 104 | $CH_2O$ | C6H5 | H | $CH_2CH_3$ | |
| 105 | $OCH_2$ | $NH-SO_2$-4-(methyl)phenyl | $CH_3$ | $CH_3$ | |
| 106 | $OCH_2$ | $NH-SO_2$-4-(methyl)phenyl | H | $CH_2CH_3$ | |
| 107 | $OCH_2$ | $NHSO_2(CH_2)_3CH_3$ | H | $CH_3$ | |
| 108 | $OCH_2$ | $NHSO_2(CH_2)_3CH_3$ | H | $CH_2CH_3$ | |
| 109 | $OCH_2$ | NH—Cbz | H | $CH_3$ | |
| 110 | $OCH_2$ | NH—Cbz | H | $CH_2CH_3$ | |
| 111 | $CH_2O$ | $NH-SO_2$-4-(methyl)phenyl | $CH_3$ | $CH_3$ | |
| 112 | $CH_2O$ | $NH-SO_2$-4-(methylphenyl) | H | $CH_2CH_3$ | |
| 113 | $CH_2O$ | $NHSO_2(CH_2)_3CH_3$ | H | $CH_3$ | |
| 114 | $CH_2O$ | $NHSO_2(CH_2)_3CH_3$ | H | $CH_2CH_3$ | |
| 115 | $CH_2O$ | NH—Cbz | H | $CH_3$ | |
| 116 | $CH_2O$ | NH—Cbz | H | $CH_2CH_3$ | |

TABLE 7

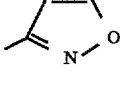

| Ex. No. | U | HET | R⁸ | R⁹ | R¹⁶ | FAB MS (M + H)⁺ |
|---|---|---|---|---|---|---|
| 121 | $CH_2O$ | dimethylisoxazolyl | H | $NHC(=O)OCH_2(C_6H_5)$ | H | |
| 122 | $CH_2O$ | dimethylisoxazolyl | H | $NHC(=O)OC(CH_3)_3$ | H | |
| 123 | $CH_2O$ | dimethylisoxazolyl | H | $NHC(=O)O(CH_2)_3CH_3$ | H | |

TABLE 7-continued

[Structure: 4-amidino-phenyl-U-HET-C(=O)-N(H)-CH(R8)-CH(R9)-C(=O)-O-R16]

| Ex. No. | U | HET | R8 | R9 | R16 | FAB MS (M + H)+ |
|---|---|---|---|---|---|---|
| 124 | CH2O | 3,5-dimethylisoxazole | H | NHC(=O)OCH2CH3 | H | |
| 125 | CH2O | 3,5-dimethylisoxazole | H | NHC(=O)OCH3 | H | |
| 126 | CH2O | 3,5-dimethylisoxazole | H | NHC(=O)(CH2)2—(C6H5) | H | |
| 127 | CH2O | 3,5-dimethylisoxazole | H | NHC(=O)CH2C(CH3)3 | H | |
| 128 | CH2O | 3,5-dimethylisoxazole | H | NHC(=O)(CH2)4CH3 | H | |
| 129 | CH2O | 3,5-dimethylisoxazole | H | NHC(=O)(CH2)3CH3 | H | |
| 130 | CH2O | 3,5-dimethylisoxazole | H | NHC(=O)CH2CH3 | H | |
| 131 | CH2O | 3,5-dimethylisoxazole | H | NHC(=O)—CH3 | H | |
| 132 | CH2O | 3,5-dimethylisoxazole | H | NHS(=O)2CH2CH3 | H | |
| 133 | CH2O | 3,5-dimethylisoxazole | H | NHS(=O)2(CH2)3CH3 | H | |
| 134 | CH2O | 3,5-dimethylisoxazole | H | NHS(=O)2(C6H5) | H | |
| 135 | CH2O | 3,5-dimethylisoxazole | H | NHS(=O)2-4-(methyl)phenyl | H | |

TABLE 7-continued

Structure: 4-amidinophenyl-U-HET-C(=O)-N(H)-CH(R8)-CH(R9)-C(=O)-O-R16

| Ex. No. | U | HET | R8 | R9 | R16 | FAB MS (M + H)+ |
|---|---|---|---|---|---|---|
| 136 | CH$_2$O | 3,5-disubstituted isoxazole | H | NHS(=O)$_2$CH$_2$(C$_6$H$_5$) | H | |
| 137 | CH$_2$O | 3,5-disubstituted isoxazole | H | NHC(=O)-2-pyridyl | H | |
| 138 | CH$_2$O | 3,5-disubstituted isoxazole | H | NHC(=O)-3-pyridyl | H | |
| 139 | CH$_2$O | 3,5-disubstituted isoxazole | H | NHC(=O)-4-pyridyl | H | |
| 140 | CH$_2$O | 3,5-disubstituted isoxazole | H | NHC(=O)OCH$_2$(C$_6$H$_5$) | Me | |
| 141 | CH$_2$O | 3,5-disubstituted isoxazole | H | NHC(=O)OC(CH$_3$)$_3$ | Me | |
| 142 | CH$_2$O | 3,5-disubstituted isoxazole | H | NHC(=O)O(CH$_2$)$_3$CH$_3$ | Me | |
| 143 | CH$_2$O | 3,5-disubstituted isoxazole | H | NHC(=O)OCH$_2$CH$_3$ | Me | |
| 144 | CH$_2$O | 3,5-disubstituted isoxazole | H | NHC(=O)OCH$_3$ | Me | |
| 145 | CH$_2$O | 3,5-disubstituted isoxazole | H | NHC(=O)(CH$_2$)2-(C$_6$H$_5$) | Me | |
| 146 | CH$_2$O | 3,5-disubstituted isoxazole | H | NHC(=O)CH$_2$C(CH$_3$)$_3$ | Me | |
| 147 | CH$_2$O | 3,5-disubstituted isoxazole | H | NHC(=O)(CH$_2$)$_4$CH$_3$ | Me | |

TABLE 7-continued
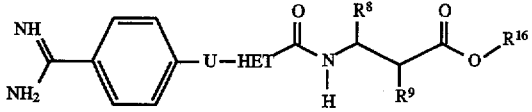
| Ex. No. | U | HET | R⁸ | R⁹ | R¹⁶ | FAB MS (M + H)⁺ |
|---|---|---|---|---|---|---|
| 148 | $CH_2O$ | 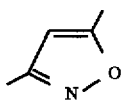 | H | $NHC(=O)(CH_2)_3CH_3$ | Me | |
| 149 | $CH_2O$ | 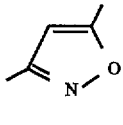 | H | $NHC(=O)CH_2CH_3$ | Me | |
| 150 | $CH_2O$ | 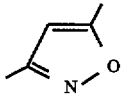 | H | $NHC(=O)-CH_3$ | Me | |
| 151 | $CH_2O$ | 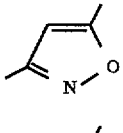 | H | $NHS(=O)_2CH_2CH_3$ | Me | |
| 152 | $CH_2O$ | 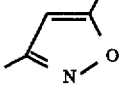 | H | $NHS(=O)_2(CH_2)_3CH_3$ | Me | |
| 153 | $CH_2O$ | 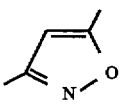 | H | $NHS(=O)_2(C_6H_5)$ | Me | |
| 154 | $CH_2O$ | 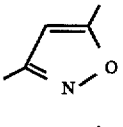 | H | $NHS(=O)_2$-4-(methyl)phenyl | Me | |
| 155 | $CH_2O$ | 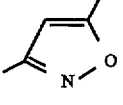 | H | $NHS(=O)_2CH_2(C_6H_5)$ | Me | |
| 156 | $CH_2O$ | 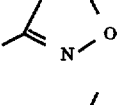 | H | $NHC(=O)$-2-pyridyl | Me | |
| 157 | $CH_2O$ | 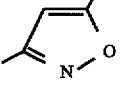 | H | $NHC(=O)$-3-pyridyl | Me | |
| 158 | $CH_2O$ | 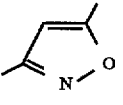 | H | $NHC(=O)$-4-pyridyl | Me | |
| 159 | $OCH_2$ | 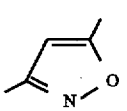 | H | $NHC(=O)O(CH_2)_3CH_3$ | H | |

TABLE 7-continued

| Ex. No. | U | HET | R⁸ | R⁹ | R¹⁶ | FAB MS (M + H)⁺ |
|---|---|---|---|---|---|---|
| 160 | OCH₂ | 3,5-dimethylisoxazole (N-O, methyls at 3,5) | H | NHS(=O)₂-4-(methyl)phenyl | H | |
| 161 | OCH₂ | 3,5-dimethylisoxazole | H | NHC(=O)O(CH₂)₃CH₃ | Me | |
| 162 | OCH₂ | 3,5-dimethylisoxazole | H | NHS(=O)₂-4-(methyl)phenyl | Me | |
| 163 | CH₂O | 3,5-dimethylisoxazole (O-N) | H | NHC(=O)O(CH₂)₃CH₃ | H | |
| 164 | CH₂O | 3,5-dimethylisoxazole (O-N) | H | NHS(=O)₂-4-(methyl)phenyl | H | |
| 165 | CH₂O | 3,5-dimethylisoxazole (O-N) | H | NHC(=O)O(CH₂)₃CH₃ | Me | |
| 166 | CH₂O | 3,5-dimethylisoxazole (O-N) | H | NHS(=O)₂-4-(methyl)phenyl | Me | |
| 167 | OCH₂ | 3,5-dimethylisoxazole (O-N) | H | NHC(=O)O(CH₂)₃CH₃ | H | |
| 168 | OCH₂ | 3,5-dimethylisoxazole (O-N) | H | NHS(=O)₂-4-(methyl)phenyl | H | |
| 169 | OCH₂ | 3,5-dimethylisoxazole (O-N) | H | NHC(=O)O(CH₂)₃CH₃ | Me | |
| 170 | OCH₂ | 3,5-dimethylisoxazole (O-N) | H | NHS(=O)₂-4-(methyl)phenyl | | |
| 171 | CH₂O | 2,5-dimethylfuran | H | NHC(=O)O(CH₂)₃CH₃ | H | |
| 172 | CH₂O | 2,5-dimethylfuran | H | NHS(=O)₂-4-(methyl)phenyl | H | |

TABLE 7-continued

Structure:

$H_2N-C(=NH)-$[phenyl]$-U-HET-C(=O)-N(H)-CH(R^8)-CH(R^9)-C(=O)-O-R^{16}$

| Ex. No. | U | HET | R⁸ | R⁹ | R¹⁶ | FAB MS (M + H)⁺ |
|---|---|---|---|---|---|---|
| 173 | CH₂O | 2,5-furan (dimethyl) | H | NHC(=O)O(CH₂)₃CH₃ | Me | |
| 174 | CH₂O | 2,5-furan (dimethyl) | H | NHS(=O)₂-4-(methyl)phenyl | Me | |
| 175 | OCH₂ | 2,5-furan (dimethyl) | H | NHC(=O)O(CH₂)₃CH₃ | H | |
| 176 | OCH₂ | 2,5-furan (dimethyl) | H | NHS(=O)₂-4-(methyl)phenyl | H | |
| 177 | OCH₂ | 2,5-furan (dimethyl) | H | NHC(=O)O(CH₂)₃CH₃ | Me | |
| 178 | OCH₂ | 2,5-furan (dimethyl) | H | NHS(=O)₂-4-(methyl)phenyl | Me | |
| 179 | CH₂O | 2,5-furan | H | NHC(=O)O(CH₂)₃CH₃ | H | |
| 180 | CH₂O | 2,5-furan | H | NHS(=O)₂-4-(methyl)phenyl | H | |
| 181 | CH₂O | 2,5-furan | H | NHC(=O)O(CH₂)₃CH₃ | Me | |
| 182 | CH₂O | 2,5-furan | H | NHS(=O)₂-4-(methyl)phenyl | Me | |
| 183 | OCH₂ | 2,5-furan | H | NHC(=O)O(CH₂)₃CH₃ | H | |
| 184 | OCH₂ | 2,5-furan | H | NHS(=O)₂-4-(methyl)phenyl | H | |
| 185 | OCH₂ | 2,5-furan | H | NHC(=O)O(CH₂)₃CH₃ | Me | |

TABLE 7-continued

| Ex. No. | U | HET | R⁸ | R⁹ | R¹⁶ | FAB MS (M + H)⁺ |
|---|---|---|---|---|---|---|
| 186 | OCH₂ | (2,4-dimethylfuran) | H | NHS(=O)₂-4-(methyl)phenyl | Me | |
| 187 | CH₂O | (2,4-dimethylfuran) | H | NHC(=O)O(CH₂)₃CH₃ | H | |
| 188 | CH₂O | (2,4-dimethylfuran) | H | NHS(=O)₂-4-(methyl)phenyl | H | |
| 189 | CH₂O | (2,4-dimethylfuran) | H | NHC(=O)O(CH₂)₃CH₃ | Me | |
| 190 | CH₂O | (2,4-dimethylfuran) | H | NHS(=O)₂-4-(methyl)phenyl | Me | |
| 191 | OCH₂ | (2,4-dimethylfuran) | H | NHC(=O)O(CH₂)₃CH₃ | H | |
| 192 | OCH₂ | (2,4-dimethylfuran) | H | MHS(=O)₂-4-(methyl)phenyl | H | |
| 193 | OCH₂ | (2,4-dimethylfuran) | H | NHC(=O)O(CH₂)₃CH₃ | Me | |
| 194 | OCH₂ | (2,4-dimethylfuran) | H | NHS(=O)₂-4-(methyl)phenyl | Me | |
| 195 | CH₂O | (methyloxazole) | H | NHC(=O)O(CH₂)₃CH₃ | H | |
| 196 | CH₂O | (methyloxazole) | H | NHS(=O)₂-4-(methyl)phenyl | H | |
| 197 | CH₂O | (methyloxazole) | H | NHC(=O)O(CH₂)₃CH₃ | Me | |
| 198 | CH₂O | (methyloxazole) | H | NHS(=O)₂-4-(methyl)phenyl | Me | |

TABLE 7-continued

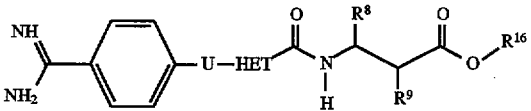

| Ex. No. | U | HET | R⁸ | R⁹ | R¹⁶ | FAB MS (M + H)⁺ |
|---|---|---|---|---|---|---|
| 199 | OCH$_2$ | 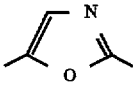 | H | NHC(=O)O(CH$_2$)$_3$CH$_3$ | H | |
| 200 | OCH$_2$ | 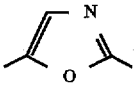 | H | NHS(=O)$_2$-4-(methyl)phenyl | H | |
| 201 | OCH$_2$ | 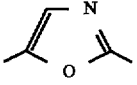 | H | NHC(=O)O(CH$_2$)$_3$CH$_3$ | Me | |
| 202 | OCH$_2$ | 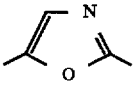 | H | NHS(=O)$_2$-4-(methyl)phenyl | Me | |
| 203 | CH$_2$O | 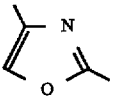 | H | NHC(=O)O(CH$_2$)$_3$CH$_3$ | H | |
| 204 | CH$_2$O | 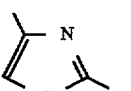 | H | NHS(=O)$_2$-4-(methyl)phenyl | H | |
| 205 | CH$_2$O | 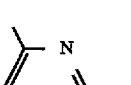 | H | NHC(=O)O(CH$_2$)$_3$CH$_3$ | Me | |
| 206 | CH$_2$O | 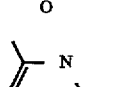 | H | NHS(=O)$_2$-4-(methyl)phenyl | Me | |
| 207 | OCH$_2$ | 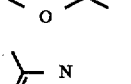 | H | NHC(=O)O(CH$_2$)$_3$CH$_3$ | H | |
| 208 | OCH$_2$ | 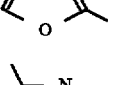 | H | NHS(=O)$_2$-4-(methyl)phenyl | H | |
| 209 | OCH$_2$ | 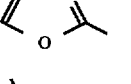 | H | NHC(=O)O(CH$_2$)$_3$CH$_3$ | Me | |
| 210 | OCH$_2$ | 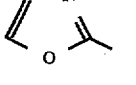 | H | NHS(=O)$_2$-4-(methyl)phenyl | Me | |
| 211 | CH$_2$O | 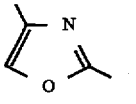 | H | NHC(=O)O(CH$_2$)$_3$CH$_3$ | H | |

TABLE 7-continued

Structure: 4-amidinophenyl–U–HET–C(=O)–N(H)–CH(R8)–CH(R9)–C(=O)–O–R16

| Ex. No. | U | HET | R8 | R9 | R16 | FAB MS (M + H)+ |
|---|---|---|---|---|---|---|
| 212 | CH2O | 2,5-thienyl | H | NHS(=O)2-4-(methyl)phenyl | H | |
| 213 | CH2O | 2,5-thienyl | H | NHC(=O)O(CH2)3 | Me | |
| 214 | CH2O | 2,5-thienyl | H | NHS(=O)2-4-(methyl)phenyl | Me | |
| 215 | OCH2 | 2,5-thienyl | H | NHC(=O)O(CH2)3CH3 | H | |
| 216 | OCH2 | 2,5-thienyl | H | NHS(=O)2-4-(methyl)phenyl | H | |
| 217 | OCH2 | 2,5-thienyl | H | NHC(=O)O(CH2)3CH3 | Me | |
| 218 | OCH2 | 2,5-thienyl | H | NHS(=O)2-4-(methyl)phenyl | Me | |
| 219 | CH2O | 2,5-thienyl | H | NHC(=O)O(CH2)3CH3 | H | |
| 220 | CH2O | 2,5-thienyl | H | NHS(=O)2-4-(methyl)phenyl | H | |
| 221 | CH2O | 2,5-thienyl | H | NHC(=O)O(CH2)3CH3 | Me | |
| 222 | CH2O | 2,5-thienyl | H | NHS(=O)2-4-(methyl)phenyl | Me | |
| 223 | OCH2 | 2,5-thienyl | H | NHC(=O)O(CH2)3CH3 | H | |
| 224 | OCH2 | 2,5-thienyl | H | NHS(=O)2-4-(methyl)phenyl | H | |
| 225 | OCH2 | 2,5-thienyl | H | NHC(=O)O(CH2)3CH3 | Me | |

TABLE 7-continued (Structure: 4-amidinophenyl-U-HET-C(=O)-NH-CHR⁸-CHR⁹-C(=O)-O-R¹⁶)

| Ex. No. | U | HET | R⁸ | R⁹ | R¹⁶ | FAB MS (M + H)⁺ |
|---|---|---|---|---|---|---|
| 226 | OCH₂ | 2,4-dimethylthiophene | H | NHS(=O)₂-4-(methyl)phenyl | Me | |
| 227 | CH₂O | 2,4-dimethylthiophene | H | NHC(=O)O(CH₂)₃CH₃ | H | |
| 228 | CH₂O | 2,4-dimethylthiophene | H | NHS(=O)₂-4-(methyl)phenyl | H | |
| 229 | CH₂O | 2,4-dimethylthiophene | H | NHC(=O)O(CH₂)₃CH₃ | Me | |
| 230 | CH₂O | 2,4-dimethylthiophene | H | NHS(=O)₂-4-(methyl)phenyl | Me | |
| 231 | OCH₂ | 2,4-dimethylthiophene | H | NHC(=O)O(CH₂)₃CH₃ | H | |
| 232 | OCH₂ | 2,4-dimethylthiophene | H | NHC(=O)₂-4-(methyl)phenyl | H | |
| 234 | OCH₂ | 2,4-dimethylthiophene | H | NHC(=O)O(CH₂)₃CH₃ | Me | |
| 235 | OCH₂ | 2,4-dimethylthiophene | H | NHS(=O)₂-4-(methyl)phenyl | Me | |
| 236 | CH₂O | 2,4-dimethylthiazole | H | NHC(=O)O(CH₂)₃CH₃ | H | |
| 237 | CH₂O | 2,4-dimethylthiazole | H | NHS(=O)₂-4-(methyl)phenyl | H | |
| 238 | CH₂O | 2,4-dimethylthiazole | H | NHC(=O)O(CH₂)₃CH₃ | Me | |
| 239 | CH₂O | 2,4-dimethylthiazole | H | NHS(=O)₂-4-(methyl)phenyl | Me | |

TABLE 7-continued

| Ex. No. | U | HET | R⁸ | R⁹ | R¹⁶ | FAB MS (M + H)⁺ |
|---|---|---|---|---|---|---|
| 240 | OCH₂ | thiazole | H | NHC(=O)O(CH₂)₃CH₃ | H | |
| 242 | OCH₂ | thiazole | H | NHS(=O)₂-4-(methyl)phenyl | H | |
| 242 | OCH₂ | thiazole | H | NHC(=O)O(CH₂)₃CH₃ | Me | |
| 243 | OCH₂ | thiazole | H | NHS(=O)₂-4-(methyl)phenyl | Me | |
| 244 | CH₂O | thiazole | H | NHC(=O)O(CH₂)₃CH₃ | H | |
| 245 | CH₂O | thiazole | H | NHS(=O)₂-4-(methyl)phenyl | H | |
| 246 | CH₂O | thiazole | H | NHC(=O)O(CH₂)₃CH₃ | Me | |
| 247 | CH₂O | thiazole | H | NHS(=O)₂-4-(methyl)phenyl | Me | |
| 248 | OCH₂ | thiazole | H | NHC(=O)O(CH₂)₃CH₃ | H | |
| 249 | OCH₂ | thiazole | H | NHS(=O)₂-4-(methyl)phenyl | H | |
| 250 | OCH₂ | thiazole | H | NHC(=O)O(CH₂)₃CH₃ | Me | |
| 251 | OCH₂ | thiazole | H | NHS(=O)₂-4-(methyl)phenyl | Me | |
| 252 | CH₂O | isothiazole | H | NHC(=O)O(CH₂)₃CH₃ | H | |

TABLE 7-continued

| Ex. No. | U | HET | R⁸ | R⁹ | R¹⁶ | FAB MS (M + H)⁺ |
|---|---|---|---|---|---|---|
| 253 | CH₂O | isothiazole (S-N) | H | NHS(=O)₂-4-(methyl)phenyl | H | |
| 254 | CH₂O | isothiazole (S-N) | H | NHC(=O)O(CH₂)₃CH₃ | Me | |
| 255 | CH₂O | isothiazole (S-N) | H | NHS(=O)₂-4-(methyl)phenyl | Me | |
| 256 | OCH₂ | isothiazole (S-N) | H | NHC(=O)O(CH₂)₃CH₃ | H | |
| 257 | OCH₂ | isothiazole (S-N) | H | NHS(=O)₂-4-(methyl)phenyl | H | |
| 258 | OCH₂ | isothiazole (S-N) | H | NHC(=O)O(CH₂)₃CH₃ | Me | |
| 259 | OCH₂ | isothiazole (S-N) | H | NHS(=O)₂-4-(methyl)phenyl | Me | |
| 260 | CH₂O | isothiazole (N-S) | H | NHC(=O)O(CH₂)₃CH₃ | H | |
| 261 | CH₂O | isothiazole (N-S) | H | NHS(=O)₂-4-(methyl)phenyl | H | |
| 262 | CH₂O | isothiazole (N-S) | H | NHC(=O)O(CH₂)₃CH₃ | Me | |
| 263 | CH₂O | isothiazole (N-S) | H | NHS(=O)₂-4-(methyl)phenyl | Me | |
| 264 | OCH₂ | isothiazole (N-S) | H | NHC(=O)O(CH₂)₃CH₃ | H | |

TABLE 7-continued

[Structure: NH=C(NH2)-C6H4-U-HET-C(=O)-N(H)-CH(R8)-CH(R9)-C(=O)-O-R16]

| Ex. No. | U | HET | R8 | R9 | R16 | FAB MS (M + H)+ |
|---|---|---|---|---|---|---|
| 265 | OCH2 | 3,5-dimethylisothiazole | H | NHS(=O)2-4-(methyl)phenyl | H | |
| 266 | OCH2 | 3,5-dimethylisothiazole | H | NHC(=O)O(CH2)3CH3 | Me | |
| 267 | OCH2 | 3,5-dimethylisothiazole | H | NHS(=O)2-4-(methyl)phenyl | Me | |
| 268 | CH2O | 2,5-dimethylpyrrole | H | NHC(=O)O(CH2)3CH3 | H | |
| 269 | CH2O | 2,5-dimethylpyrrole | H | NHS(=O)2-4-(methyl)phenyl | H | |
| 270 | CH2O | 2,5-dimethylpyrrole | H | NHC(=O)O(CH2)3CH3 | Me | |
| 271 | CH2O | 2,5-dimethylpyrrole | H | NHS(=O)2-4-(methyl)phenyl | Me | |
| 272 | OCH2 | 2,5-dimethylpyrrole | H | NHC(=O)O(CH2)3CH3 | H | |
| 273 | OCH2 | 2,5-dimethylpyrrole | H | NHS(=O)2-4-(methyl)phenyl | H | |
| 274 | OCH2 | 2,5-dimethylpyrrole | H | NHC(=O)O(CH2)3CH3 | Me | |
| 275 | OCH2 | 2,5-dimethylpyrrole | H | NHS(=O)2-4-(methyl)phenyl | Me | |
| 276 | CH2O | 2,4-dimethylpyrrole | H | NHC(=O)O(CH2)3CH3 | H | |

TABLE 7-continued

Structure: NH=C(NH2)-C6H4-U-HET-C(=O)-N(H)-C(R8)(H)-C(R9)(H)-C(=O)-O-R16

| Ex. No. | U | HET | R8 | R9 | R16 | FAB MS (M + H)+ |
|---|---|---|---|---|---|---|
| 277 | CH2O | 2,4-dimethyl-pyrrole (NH) | H | NHS(=O)2-4-(methyl)phenyl | H | |
| 278 | CH2O | 2,4-dimethyl-pyrrole (NH) | H | NHC(=O)O(CH2)3CH3 | Me | |
| 279 | CH2O | 2,4-dimethyl-pyrrole (NH) | H | NHS(=O)2-4-(methyl)phenyl | Me | |
| 280 | OCH2 | 2,4-dimethyl-pyrrole (NH) | H | NHC(=O)O(CH2)3CH3 | H | |
| 281 | OCH2 | 2,4-dimethyl-pyrrole (NH) | H | NHS(=O)2-4-(methyl)phenyl | H | |
| 282 | OCH2 | 2,4-dimethyl-pyrrole (NH) | H | NHC(=O)O(CH2)3CH3 | Me | |
| 283 | OCH2 | 2,4-dimethyl-pyrrole (NH) | H | NHS(=O)2-4-(methyl)phenyl | Me | |
| 284 | CH2O | 2,4-dimethyl-pyrrole (NH) | H | NHC(=O)O(CH2)3CH3 | H | |
| 285 | CH2O | 2,4-dimethyl-pyrrole (NH) | H | NHS(=O)2-4-(methyl)phenyl | H | |
| 286 | CH2O | 2,4-dimethyl-pyrrole (NH) | H | NHC(=O)O(CH2)3CH3 | Me | |

TABLE 7-continued

[Structure: NH=C(NH₂)-C₆H₄-U-HET-C(=O)-N(H)-C(R⁸)(H)-C(R⁹)(H)-C(=O)-O-R¹⁶]

| Ex. No. | U | HET | R⁸ | R⁹ | R¹⁶ | FAB MS (M + H)⁺ |
|---|---|---|---|---|---|---|
| 287 | CH₂O | 2,4-dimethyl-pyrrole | H | NHS(=O)₂-4-(methyl)phenyl | Me | |
| 288 | OCH₂ | 2,4-dimethyl-pyrrole | H | NHC(=O)O(CH₂)₃CH₃ | H | |
| 289 | OCH₂ | 2,4-dimethyl-pyrrole | H | NHS(=O)₂-4-(methyl)phenyl | H | |
| 290 | OCH₂ | 2,4-dimethyl-pyrrole | H | NHC(=O)O(CH₂)₃CH₃ | Me | |
| 291 | OCH₂ | 2,4-dimethyl-pyrrole | H | NHS(=O)₂-4-(methyl)phenyl | Me | |
| 292 | CH₂O | 2,5-dimethyl-imidazole | H | NHC(=O)O(CH₂)₃CH₃ | H | |
| 293 | CH₂O | 2,5-dimethyl-imidazole | H | NHS(=O)₂-4-(methyl)phenyl | H | |
| 294 | CH₂O | 2,5-dimethyl-imidazole | H | NHC(=O)O(CH₂)₃CH₃ | Me | |
| 295 | CH₂O | 2,5-dimethyl-imidazole | H | NHS(=O)₂-4-(methyl)phenyl | Me | |
| 296 | OCH₂ | 2,5-dimethyl-imidazole | H | NHC(=O)O(CH₂)₃CH₃ | H | |
| 297 | OCH₂ | 2,5-dimethyl-imidazole | H | NHS(=O)₂-4-(methyl)phenyl | H | |

TABLE 7-continued

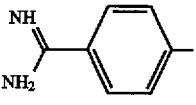

| Ex. No. | U | HET | R⁸ | R⁹ | R¹⁶ | FAB MS (M + H)⁺ |
|---|---|---|---|---|---|---|
| 298 | OCH$_2$ | 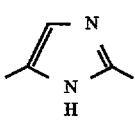 | H | NHC(=O)O(CH$_2$)$_3$CH$_3$ | Me | |
| 299 | OCH$_2$ | 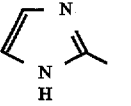 | H | NHS(=O)$_2$-4-(methyl)phenyl | Me | |
| 300 | CH$_2$O | 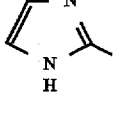 | H | NHC(=O)O(CH$_2$)$_3$CH$_3$ | H | |
| 301 | CH$_2$O | 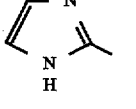 | H | NHS(=O)$_2$-4-(methyl)phenyl | H | |
| 302 | CH$_2$O | 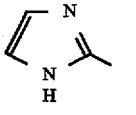 | H | NHC(=O)O(CH$_2$)$_3$CH$_3$ | Me | |
| 303 | CH$_2$O | 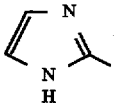 | H | NHS(=O)$_2$-4-(methyl)phenyl | Me | |
| 304 | OCH$_2$ | 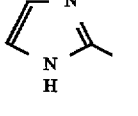 | H | NHC(=O)O(CH$_2$)$_3$CH$_3$ | H | |
| 305 | OCH$_2$ | 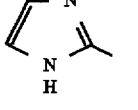 | H | NHS(=O)$_2$-4-(methyl)phenyl | H | |
| 306 | OCH$_2$ | 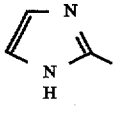 | H | NHC(=O)O(CH$_2$)$_3$CH$_3$ | Me | |
| 307 | OCH$_2$ | 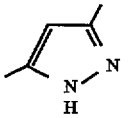 | H | NHS(=O)$_2$-4-(methyl)phenyl | Me | |
| 308 | CH$_2$O |  | H | NHC(=O)O(CH$_2$)$_3$CH$_3$ | H | |

TABLE 7-continued

Structure: NH/NH$_2$-C(=NH)-C$_6$H$_4$-U-HET-C(=O)-N(H)-C(R$^8$)H-C(R$^9$)H-C(=O)-O-R$^{16}$

| Ex. No. | U | HET | R$^8$ | R$^9$ | R$^{16}$ | FAB MS (M + H)$^+$ |
|---|---|---|---|---|---|---|
| 309 | CH$_2$O | 3,5-dimethyl-pyrazole (NH) | H | NHS(=O)$_2$-4-(methyl)phenyl | H | |
| 310 | CH$_2$O | 3,5-dimethyl-pyrazole (NH) | H | NHC(=O)O(CH$_2$)$_3$CH$_3$ | Me | |
| 311 | CH$_2$O | 3,5-dimethyl-pyrazole (NH) | H | NHS(=O)$_2$-4-(methyl)phenyl | Me | |
| 312 | OCH$_2$ | 3,5-dimethyl-pyrazole (NH) | H | NHC(=O)O(CH$_2$)$_3$CH$_3$ | H | |
| 313 | OCH$_2$ | 3,5-dimethyl-pyrazole (NH) | H | NHS(=O)$_2$-4-(methyl)phenyl | H | |
| 314 | OCH$_2$ | 3,5-dimethyl-pyrazole (NH) | H | NHC(=O)O(CH$_2$)$_3$CH$_3$ | Me | |
| 315 | OCH$_2$ | 3,5-dimethyl-pyrazole (NH) | H | NHS(=O)$_2$-4-(methyl)phenyl | Me | |
| 316 | CH$_2$O | methyl-oxadiazole | H | NHC(=O)O(CH$_2$)$_3$CH$_3$ | H | |
| 317 | CH$_2$O | methyl-oxadiazole | H | NHS(=O)$_2$-4-(methyl)phenyl | H | |
| 318 | CH$_2$O | methyl-oxadiazole | H | NHC(=O)O(CH$_2$)$_3$CH$_3$ | Me | |
| 319 | CH$_2$O | methyl-oxadiazole | H | NHS(=O)$_2$-4-(methyl)phenyl | Me | |

TABLE 7-continued

| Ex. No. | U | HET | R⁸ | R⁹ | R¹⁶ | FAB MS (M + H)⁺ |
|---|---|---|---|---|---|---|
| 320 | OCH$_2$ | (N-O-N oxadiazole) | H | NHC(=O)O(CH$_2$)$_3$CH$_3$ | H | |
| 321 | OCH$_2$ | (N-O-N oxadiazole) | H | NHS(=O)$_2$-4-(methyl)phenyl | H | |
| 322 | OCH$_2$ | (N-O-N oxadiazole) | H | NHC(=O)O(CH$_2$)$_3$CH$_3$ | Me | |
| 323 | OCH$_2$ | (N-O-N oxadiazole) | H | NHS(=O)$_2$-4-(methyl)phenyl | Me | |
| 324 | CH$_2$O | (N-N-O oxadiazole) | H | NHC(=O)O(CH$_2$)$_3$CH$_3$ | H | |
| 325 | CH$_2$O | (N-N-O oxadiazole) | H | NHS(=O)$_2$-4-(methyl)phenyl | H | |
| 326 | CH$_2$O | (N-N-O oxadiazole) | H | NHC(=O)O(CH$_2$)$_3$CH$_3$ | Me | |
| 327 | CH$_2$O | (N-N-O oxadiazole) | H | NHS(=O)$_2$-4-(methyl)phenyl | Me | |
| 328 | OCH$_2$ | (N-N-O oxadiazole) | H | NHC(=O)O(CH$_2$)$_3$CH$_3$ | Me | |
| 329 | OCH$_2$ | (N-N-O oxadiazole) | H | NHS(=O)$_2$-4-(methyl)phenyl | H | |
| 330 | OCH$_2$ | (N-N-O oxadiazole) | H | NHC(=O)O(CH$_2$)$_3$CH$_3$ | Me | |
| 331 | OCH$_2$ | (N-N-O oxadiazole) | H | NHS(=O)$_2$-4-(methyl)phenyl | Me | |
| 332 | CH$_2$O | (N-S-N thiadiazole) | H | NHC(=O)O(CH$_2$)$_3$CH$_3$ | H | |

TABLE 7-continued

| Ex. No. | U | HET | R⁸ | R⁹ | R¹⁶ | FAB MS (M + H)⁺ |
|---|---|---|---|---|---|---|
| 333 | CH₂O | (thiazole N=/S-N) | H | NHS(=O)₂-4-(methyl)phenyl | H | |
| 334 | CH₂O | (thiazole N=/S-N) | H | NHC(=O)O(CH₂)₃CH₃ | Me | |
| 335 | CH₂O | (thiazole N=/S-N) | H | NHS(=O)₂-4-(methyl)phenyl | Me | |
| 336 | OCH₂ | (thiazole N=/S-N) | H | NHC(=O)O(CH₂)₃CH₃ | H | |
| 337 | OCH₂ | (thiazole N=/S-N) | H | NHS(=O)₂-4-(methyl)phenyl | H | |
| 338 | OCH₂ | (thiazole N=/S-N) | H | NHC(=O)O(CH₂)₃CH₃ | Me | |
| 339 | OCH₂ | (thiazole N=/S-N) | H | NHS(=O)₂-4-(methyl)phenyl | Me | |
| 340 | CH₂O | (thiadiazole N=/N-S) | H | NHC(=O)O(CH₂)₃CH₃ | H | |
| 341 | CH₂O | (thiadiazole N=/N-S) | H | NHS(=O)₂-4-(methyl)phenyl | H | |
| 342 | CH₂O | (thiadiazole N=/N-S) | H | NHC(=O)O(CH₂)₃CH₃ | Me | |
| 343 | CH₂O | (thiadiazole N=/N-S) | H | NHS(=O)₂-4-(methyl)phenyl | Me | |
| 345 | OCH₂ | (thiadiazole N=/N-S) | H | NHC(=O)O(CH₂)₃CH₃ | H | |

TABLE 7-continued
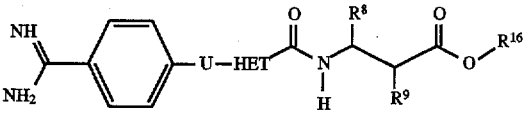
| Ex. No. | U | HET | R⁸ | R⁹ | R¹⁶ | FAB MS (M + H)⁺ |
|---|---|---|---|---|---|---|
| 346 | OCH₂ | 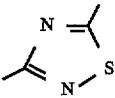 | H | NHS(=O)₂-4-(methyl)phenyl | H | |
| 347 | OCH₂ | 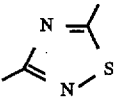 | H | NHC(=O)O(CH₂)₃CH₃ | Me | |
| 348 | OCH₂ | 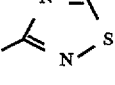 | H | NHS(=O)₂-4-(methyl)phenyl | Me | |
| 349 | CH₂O | 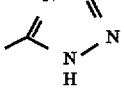 | H | NHC(=O)O(CH₂)₃CH₃ | H | |
| 350 | CH₂O | 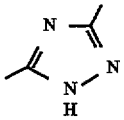 | H | NHS(=O)₂-4-(methyl)phenyl | H | |
| 351 | CH₂O | 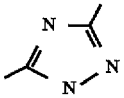 | H | NHC(=O)O(CH₂)₃CH₃ | Me | |
| 352 | CH₂O | 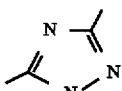 | H | NHS(=O)₂-4-(methyl)phenyl | Me | |
| 353 | OCH₂ | 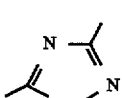 | H | NHC(=O)O(CH₂)₃CH₃ | H | |
| 354 | OCH₂ | 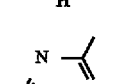 | H | NHS(=O)₂-4-(methyl)phenyl | H | |
| 356 | OCH₂ | 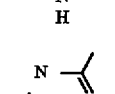 | H | NHC(=O)O(CH₂)₃CH₃ | Me | |
| 357 | OCH₂ | 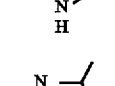 | H | NHS(=O)₂-4-(methyl)phenyl | Me | |

TABLE 7-continued

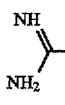

| Ex. No. | U | HET | R[8] | R[9] | R[16] | FAB MS (M + H)+ |
|---|---|---|---|---|---|---|
| 358 | $CH_2O$ | 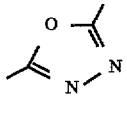 | H | $NHC(=O)O(CH_2)_3CH_3$ | H | |
| 359 | $CH_2O$ | 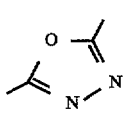 | H | $NHS(=O)_2$-4-(methyl)phenyl | H | |
| 360 | $CH_2O$ | 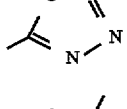 | H | $NHC(=O)O(CH_2)_3CH_3$ | Me | |
| 361 | $CH_2O$ | 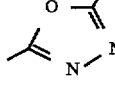 | H | $NHS(=O)_2$-4-(methyl)phenyl | Me | |
| 362 | $OCH_2$ | 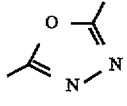 | H | $NHC(=O)O(CH_2)_3CH_3$ | H | |
| 363 | $OCH_2$ | 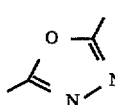 | H | $NHS(=O)_2$-4-(methyl)phenyl | H | |
| 364 | $OCH_2$ | 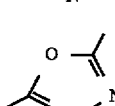 | H | $NHC(=O)O(CH_2)_3CH_3$ | Me | |
| 365 | $OCH_2$ | 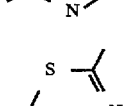 | H | $NHS(=O)_2$-4-(methyl)phenyl | Me | |
| 366 | $CH_2O$ | 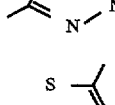 | H | $NHC(=O)O(CH_2)_3CH_3$ | H | |
| 367 | $CH_2O$ | 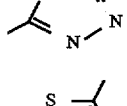 | H | $NHS(=O)_2$-4-(methyl)phenyl | H | |
| 368 | $CH_2O$ | 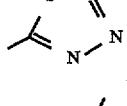 | H | $NHC(=O)O(CH_2)_3CH_3$ | Me | |
| 369 | $CH_2O$ | | H | $NHS(=O)_2$-4-(methyl)phenyl | Me | |

TABLE 7-continued

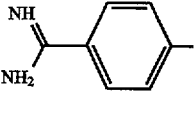

| Ex. No. | U | HET | R⁸ | R⁹ | R¹⁶ | FAB MS (M + H)⁺ |
|---|---|---|---|---|---|---|
| 370 | OCH₂ | 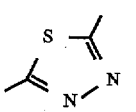 | H | NHC(=O)O(CH₂)₃CH₃ | H | |
| 371 | OCH₂ | 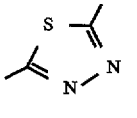 | H | NHS(=O)₂-4-(methyl)phenyl | H | |
| 372 | OCH₂ | 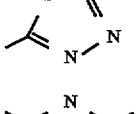 | H | NHC(=O)O(CH₂)₃CH₃ | Me | |
| 373 | OCH₂ | 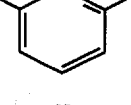 | H | NHS(=O)₂-4-(methyl)phenyl | Me | |
| 374 | CH₂O | 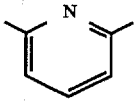 | H | NHC(=O)O(CH₂)₃CH₃ | H | |
| 375 | CH₂O | 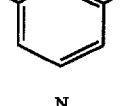 | H | NHS(=O)₂-4-(methyl)phenyl | H | |
| 376 | CH₂O | 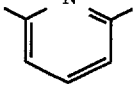 | H | NHC(=O)O(CH₂)₃CH₃ | Me | |
| 377 | CH₂O | 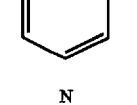 | H | NHS(=O)₂-4-(methyl)phenyl | Me | |
| 378 | OCH₂ | 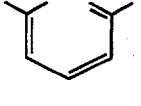 | H | NHC(=O)O(CH₂)₃CH₃ | H | |
| 379 | OCH₂ | 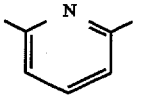 | H | NHS(=O)₂-4-(methyl)phenyl | H | |
| 380 | OCH₂ | 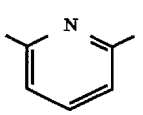 | H | NHC(=O)O(CH₂)₃CH₃ | Me | |
| 381 | OCH₂ | | H | NHS(=O)₂-4-(methyl)phenyl | Me | |

TABLE 7-continued

| Ex. No. | U | HET | R⁸ | R⁹ | R¹⁶ | FAB MS (M + H)⁺ |
|---|---|---|---|---|---|---|
| 382 | CH₂O | 4-pyridyl (2-linked) | H | NHC(=O)O(CH₂)₃CH₃ | H | |
| 383 | CH₂O | 4-pyridyl (2-linked) | H | NHS(=O)₂-4-(methyl)phenyl | H | |
| 384 | CH₂O | 4-pyridyl (2-linked) | H | NHC(=O)O(CH₂)₃CH₃ | Me | |
| 385 | CH₂O | 4-pyridyl (2-linked) | H | NHS(=O)₂-4-(methyl)phenyl | Me | |
| 386 | OCH₂ | 4-pyridyl (2-linked) | H | NHC(=O)O(CH₂)₃CH₃ | H | |
| 387 | OCH₂ | 4-pyridyl (2-linked) | H | NHS(=O)₂-4-(methyl)phenyl | H | |
| 388 | OCH₂ | 4-pyridyl (2-linked) | H | NHC(=O)O(CH₂)₃CH₃ | Me | |
| 389 | OCH₂ | 4-pyridyl (2-linked) | H | NHS(=O)₂-4-(methyl)phenyl | Me | |
| 390 | CH₂O | 3,5-pyridyl | H | NHC(=O)O(CH₂)₃CH₃ | H | |
| 391 | CH₂O | 3,5-pyridyl | H | NHS(=O)₂-4-(methyl)phenyl | H | |
| 392 | CH₂O | 3,5-pyridyl | H | NHC(=O)O(CH₂)₃CH₃ | Me | |
| 393 | CH₂O | 3,5-pyridyl | H | NHS(=O)₂-4-(methyl)phenyl | Me | |
| 394 | OCH₂ | 3,5-pyridyl | H | NHC(=O)O(CH₂)₃CH₃ | H | |

TABLE 7-continued

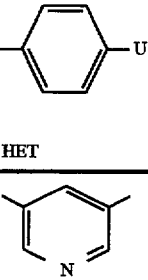

| Ex. No. | U | HET | R[8] | R[9] | R[16] | FAB MS (M + H)+ |
|---|---|---|---|---|---|---|
| 395 | OCH$_2$ | 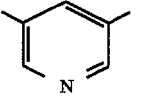 | H | NHS(=O)$_2$-4-(methyl)phenyl | H | |
| 396 | OCH$_2$ | 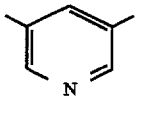 | H | NHC(=O)O(CH$_2$)$_3$CH$_3$ | Me | |
| 397 | OCH$_2$ | 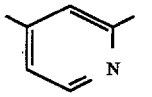 | H | NHS(=O)$_2$-4-(methyl)phenyl | Me | |
| 398 | CH$_2$O | 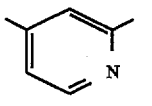 | H | NHC(=O)O(CH$_2$)$_3$CH$_3$ | H | |
| 399 | CH$_2$O | 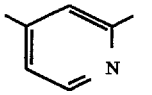 | H | NHS(=O)$_2$-4-(methyl)phenyl | H | |
| 400 | CH$_2$O | 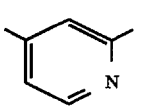 | H | NHC(=O)O(CH$_2$)$_3$CH$_3$ | Me | |
| 401 | CH$_2$O | 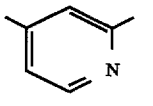 | H | NHS(=O)$_2$-4-(methyl)phenyl | Me | |
| 402 | OCH$_2$ | 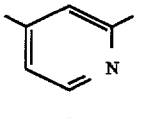 | H | NHC(=O)O(CH$_2$)$_3$CH$_3$ | H | |
| 403 | OCH$_2$ | 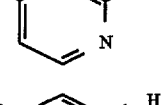 | H | NHS(=O)$_2$-4-(methyl)phenyl | H | |
| 404 | OCH$_2$ | 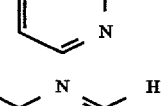 | H | NHC(=O)O(CH$_2$)$_3$CH$_3$ | Me | |
| 405 | OCH$_2$ | 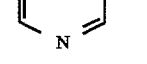 | H | NHS(=O)$_2$-4-(methyl)phenyl | Me | |
| 406 | CH$_2$O | 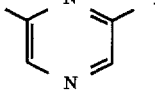 | H | NHC(=O)O(CH$_2$)$_3$CH$_3$ | H | |
| 407 | CH$_2$O | 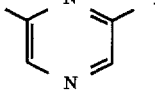 | H | NHS(=O)$_2$-4-(methyl)phenyl | H | |

TABLE 7-continued

[Structure: NH=C(NH2)-C6H4-U-HET-C(=O)-N(H)-CH(R8)-CH(R9)-C(=O)-O-R16]

| Ex. No. | U | HET | R8 | R9 | R16 | FAB MS (M + H)+ |
|---------|-----|---------------------|----|-------------------------------|-----|-----------------|
| 408 | CH2O | pyrimidine (2,4-linked via N1,N3) | H | NHC(=O)O(CH2)3CH3 | Me | |
| 409 | CH2O | pyrimidine | H | NHS(=O)2-4-(methyl)phenyl | Me | |
| 410 | OCH2 | pyrimidine | H | NHC(=O)O(CH2)3CH3 | H | |
| 411 | OCH2 | pyrimidine | H | NHS(=O)2-4-(methyl)phenyl | H | |
| 412 | OCH2 | pyrimidine | H | NHC(=O)O(CH2)3CH3 | Me | |
| 413 | OCH2 | pyrimidine | H | NHS(=O)2-4-(methyl)phenyl | Me | |
| 414 | CH2O | pyrazine | H | NHS(=O)2-4-(methyl)phenyl | Me | |
| 415 | CH2O | pyrazine | H | NHC(=O)O(CH2)3CH3 | H | |
| 416 | CH2O | pyrazine | H | NHS(=O)2-4-(methyl)phenyl | H | |
| 417 | CH2O | pyrazine | H | NHC(=O)O(CH2)3CH3 | Me | |
| 418 | OCH2 | pyrazine | H | NHS(=O)2-4-(methyl)phenyl | Me | |
| 419 | OCH2 | pyrazine | H | NHC(=O)O(CH2)3CH3 | H | |

TABLE 7-continued

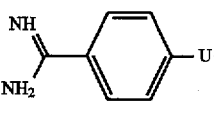

| Ex. No. | U | HET | R⁸ | R⁹ | R¹⁶ | FAB MS (M + H)⁺ |
|---|---|---|---|---|---|---|
| 420 | OCH$_2$ | 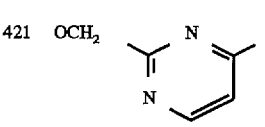 | H | NHS(=O)$_2$-4-(methyl)phenyl | H | |
| 421 | OCH$_2$ | 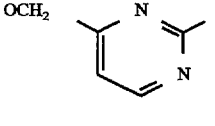 | H | NHC(=O)O(CH$_2$)$_3$CH$_3$ | Me | |
| 422 | OCH$_2$ | 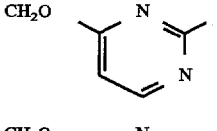 | H | NHS(=O)$_2$-4-(methyl)phenyl | Me | |
| 423 | CH$_2$O | 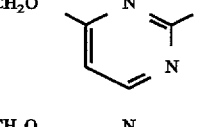 | H | NHC(=O)O(CH$_2$)$_3$CH$_3$ | H | |
| 424 | CH$_2$O | 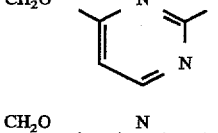 | H | NHS(=O)$_2$-4-(methyl)phenyl | H | |
| 425 | CH$_2$O | 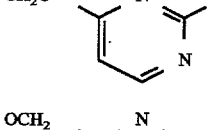 | H | NHC(=O)O(CH$_2$)$_3$CH$_3$ | Me | |
| 426 | CH$_2$O | 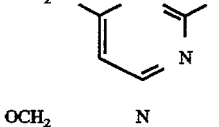 | H | NHS(=O)$_2$-4-(methyl)phenyl | Me | |
| 427 | OCH$_2$ | 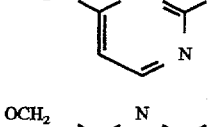 | H | NHC(=O)O(CH$_2$)$_3$CH$_3$ | H | |
| 428 | OCH$_2$ | 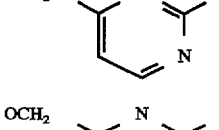 | H | NHS(=O)$_2$-4-(methyl)phenyl | H | |
| 429 | OCH$_2$ | 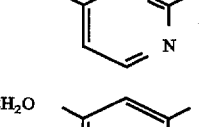 | H | NHC(=O)O(CH$_2$)$_3$CH$_3$ | Me | |
| 430 | OCH$_2$ | 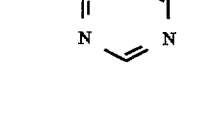 | H | NHS(=O)$_2$-4-(methyl)phenyl | Me | |
| 431 | CH$_2$O | | H | NHC(=O)O(CH$_2$)$_3$CH$_3$ | H | |

TABLE 7-continued

| Ex. No. | U | HET | R⁸ | R⁹ | R¹⁶ | FAB MS (M + H)⁺ |
|---|---|---|---|---|---|---|
| 432 | CH₂O | pyrimidine | H | NHS(=O)₂-4-(methyl)phenyl | H | |
| 433 | CH₂O | pyrimidine | H | NHC(=O)O(CH₂)₃CH₃ | Me | |
| 434 | CH₂O | pyrimidine | H | NHS(=O)₂-4-(methyl)phenyl | Me | |
| 435 | OCH₂ | pyrimidine | H | NHC(=O)O(CH₂)₃CH₃ | H | |
| 436 | OCH₂ | pyrimidine | H | NHS(=O)₂-4-(methyl)phenyl | H | |
| 437 | OCH₂ | pyrimidine | H | NHC(=O)O(CH₂)₃CH₃ | Me | |
| 438 | OCH₂ | pyrimidine | H | NHS(=O)₂-4-(methyl)phenyl | Me | |
| 439 | CH₂O | pyridazine | H | NHC(=O)O(CH₂)₃CH₃ | H | |
| 440 | CH₂O | pyridazine | H | NHS(=O)₂-4-(methyl)phenyl | H | |
| 441 | CH₂O | pyridazine | H | NHC(=O)O(CH₂)₃CH₃ | Me | |
| 442 | CH₂O | pyridazine | H | NHS(=O)₂-4-(methyl)phenyl | Me | |
| 443 | OCH₂ | pyridazine | H | NHC(=O)O(CH₂)₃CH₃ | H | |
| 444 | OCH₂ | pyridazine | H | NHS(=O)₂-4-(methyl)phenyl | H | |

TABLE 7-continued

| Ex. No. | U | HET | R⁸ | R⁹ | R¹⁶ | FAB MS (M + H)⁺ |
|---|---|---|---|---|---|---|
| 445 | OCH$_2$ | pyridazine | H | NHC(=O)O(CH$_2$)$_3$CH$_3$ | Me | |
| 446 | OCH$_2$ | pyridazine | H | NHS(=O)$_2$-4-(methyl)phenyl | Me | |
| 447 | CH$_2$O | pyridazine | H | NHC(=O)O(CH$_2$)$_3$CH$_3$ | H | |
| 448 | CH$_2$O | pyridazine | H | NHS(=O)$_2$-4-(methyl)phenyl | H | |
| 449 | CH$_2$O | pyridazine | H | NHC(=O)O(CH$_2$)$_3$CH$_3$ | Me | |
| 450 | CH$_2$O | pyridazine | H | NHS(=O)$_2$-4-(methyl)phenyl | Me | |
| 451 | OCH$_2$ | pyridazine | H | NHC(=O)O(CH$_2$)$_3$CH$_3$ | H | |
| 452 | OCH$_2$ | pyridazine | H | NHS(=O)$_2$-4-(methyl)phenyl | H | |
| 453 | OCH$_2$ | pyridazine | H | NHC(=O)O(CH$_2$)$_3$CH$_3$ | Me | |
| 454 | OCH$_2$ | pyridazine | H | NHS(=O)$_2$-4-(methyl)phenyl | Me | |
| 455 | CH$_2$O | triazine | H | NHC(=O)O(CH$_2$)$_3$CH$_3$ | H | |
| 456 | CH$_2$O | triazine | H | NHS(=O)$_2$-4-(methyl)phenyl | H | |

TABLE 7-continued

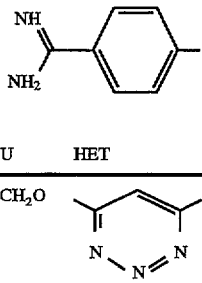

| Ex. No. | U | HET | R[8] | R[9] | R[16] | FAB MS (M + H)+ |
|---|---|---|---|---|---|---|
| 457 | CH$_2$O | triazine | H | NHC(=O)O(CH$_2$)$_3$CH$_3$ | Me | |
| 458 | CH$_2$O | triazine | H | NHS(=O)$_2$-4-(methyl)phenyl | Me | |
| 459 | OCH$_2$ | triazine | H | NHC(=O)O(CH$_2$)$_3$CH$_3$ | H | |
| 460 | OCH$_2$ | triazine | H | NHS(=O)$_2$-4-(methyl)phenyl | | |
| 461 | OCH$_2$ | triazine | H | NHC(=O)O(CH$_2$)$_3$CH$_3$ | Me | |
| 462 | OCH$_2$ | triazine | H | NHS(=O)$_2$-4-(methyl)phenyl | Me | |
| 463 | CH$_2$O | triazine | H | NHC(=O)O(CH$_2$)$_3$CH$_3$ | H | |
| 464 | CH$_2$O | triazine | H | NHS(=O)$_2$-4-(methyl)phenyl | H | |
| 465 | CH$_2$O | triazine | H | NHC(=O)O(CH$_2$)$_3$CH$_3$ | Me | |
| 466 | CH$_2$O | triazine | H | NHS(=O)$_2$-4-(methyl)phenyl | Me | |
| 467 | OCH$_2$ | triazine | H | NHC(=O)O(CH$_2$)$_3$CH$_3$ | H | |
| 468 | OCH$_2$ | triazine | H | NHS(=O)$_2$-4-(methyl)phenyl | H | |

TABLE 7-continued

| Ex. No. | U | HET | R⁸ | R⁹ | R¹⁶ | FAB MS (M + H)⁺ |
|---|---|---|---|---|---|---|
| 469 | OCH$_2$ | pyridazine | H | NHC(=O)O(CH$_2$)$_3$CH$_3$ | Me | |
| 470 | OCH$_2$ | pyridazine | H | NHS(=O)$_2$-4-(methyl)phenyl | Me | |
| 471 | CH$_2$O | pyridazine | H | NHC(=O)O(CH$_2$)$_3$CH$_3$ | H | |
| 472 | CH$_2$O | pyridazine | H | NHS(=O)$_2$-4-(methyl)phenyl | H | |
| 473 | CH$_2$O | pyridazine | H | NHC(=O)O(CH$_2$)$_3$CH$_3$ | Me | |
| 474 | CH$_2$O | pyridazine | H | NHS(=O)$_2$-4-(methyl)phenyl | Me | |
| 475 | OCH$_2$ | pyridazine | H | NHC(=O)O(CH$_2$)$_3$CH$_3$ | H | |
| 476 | OCH$_2$ | pyridazine | H | NHS(=O)$_2$-4-(methyl)phenyl | H | |
| 477 | OCH$_2$ | pyridazine | H | NHC(=O)O(CH$_2$)$_3$CH$_3$ | Me | |
| 478 | OCH$_2$ | pyridazine | H | NHS(=O)$_2$-4-(methyl)phenyl | Me | |

TABLE 8

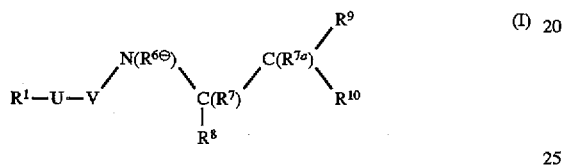

| Ex. No | R¹—U | HET | R⁸ | R⁹ | R¹⁶ | FAB MS (M + H)⁺ |
|---|---|---|---|---|---|---|
| 479 | 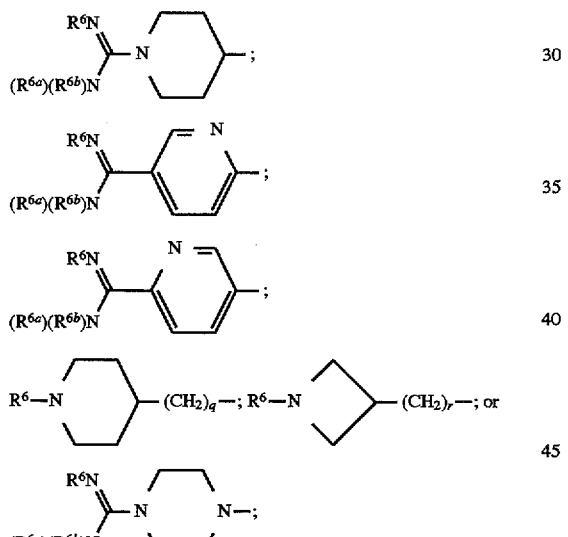 | —CH₂—O— 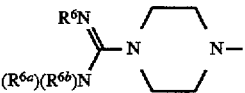 | H | NHCO₂nBu | Me | |

What is claimed is:

1. A compound of Formula I:

$$R^1-U-V \diagup \substack{N(R^{6e}) \\ \diagdown C(R^7) \\ | \\ R^8} \diagup \substack{C(R^{7a}) \\ \diagdown R^{10}} \diagup \substack{R^9}$$ (I)

or a pharmaceutically acceptable salt form thereof wherein:
R¹ is selected from:

[structures]

$R^6N\diagdown$ (with $(R^{6a})(R^{6b})N$)—N piperidine;

pyridine analogs;

$R^6$—N piperidine—$(CH_2)_q$—; $R^6$—N azetidine—$(CH_2)_r$—; or $R^6N$—N piperazine—;

q is 1, 2, or 3;
r is 2, 3, or 4;
$R^6$ and $R^{6a}$ are independently selected from: H, $C_1$–$C_{10}$ alkyl, $C_2$–$C_6$ alkenyl, $C_3$–$C_{11}$ cycloalkyl, $C_4$–$C_{11}$ cycloalkylalkyl, aryl, aryl($C_1$–$C_6$ alkyl)-, ($C_1$–$C_7$ alkyl) carbonyl, arylcarbonyl, ($C_1$–$C_{10}$ alkoxy)carbonyl, $C_4$–$C_{11}$ cycloalkoxycarbonyl, $C_7$–$C_{11}$ bicycloalkoxycarbonyl, aryloxycarbonyl, aryl($C_1$–$C_{10}$ alkyl)carbonyl, or aryl($C_1$–$C_{10}$ alkoxy) carbonyl;

$R^7$ and $R^{7a}$ are selected independently from: H or $C_1$–$C_4$ alkyl;

$R^{6b}$ is selected from: H, $C_1$–$C_{10}$ alkyl, $C_2$–$C_6$ alkenyl, $C_3$–$C_{11}$ cycloalkyl, $C_4$–$C_{15}$ cycloalkylalkyl, aryl, aryl ($C_1$–$C_{10}$ alkyl)-;

$R^{6e}$ is selected from: H, $C_1$–$C_{10}$ alkyl, $C_2$–$C_6$ alkenyl, $C_3$–$C_{11}$ cycloalkyl, $C_4$–$C_{15}$ cycloalkylalkyl, aryl, aryl ($C_1$–$C_{10}$ alkyl)-;

alternatively, $R^{6e}$ and $R^7$ can be taken together with the nitrogen and carbon atom to which they are attached to form a 5–7-membered nitrogen heterocycle, said heterocycle optionally including one additional N, O or S atom;

U is selected from:
—$CH_2$—$CH_2$—$CH_2$-substituted with 0–4 $R^3$,
—X—$CH_2$—$CH_2$-substituted with 0–4 $R^3$,
—$CH_2$—X—$CH_2$-substituted with 0–4 $R^3$,
—$CH_2$—$CH_2$—X-substituted with 0–4 $R^3$,
—$CH_2$—CH=CH-substituted with 0–4 $R^3$,
—CH=CH—$CH_2$-substituted with 0–4 $R^3$,
—$CH_2$—C≡C-substituted with 0–2 $R^3$,
—C≡C—$CH_2$-substituted with 0–2 $R^3$,
—CH=CH-substituted with 0—2 $R^3$,
—C≡C—,
—$CH_2$—$CH_2$-substituted with 0–4 $R^3$,
—X—$CH_2$-substituted with 0—2 $R^3$,
—$CH_2$—X-substituted with 0—2 $R^3$,
—X—, or
—$CH_2$-substituted with 0–2 $R^3$;

X is selected from: O, S, S(=O), $SO_2$, $SO_2N(R^{6c})$, $N(R^{6c})SO_2$, $N(R^{6c})$, $N(R^{12})$, $N(R^{6c})C(=O)$;

with the proviso that when R¹ is $R^6N$—N piperazine—N— then X is not S, S(=O), or $SO_2N(R^{6c})$;

$R^{12}$ and $R^{13}$ are independently selected from: H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, aryl, $C_2$–$C_6$ alkenyl, $C_3$–$C_{11}$ cycloalkyl, $C_4$–$C_{15}$ cycloalkylalkyl, aryl($C_1$–$C_{10}$ alkyl), arylcarbonyl, $C_4$–$C_{11}$ cycloalkoxycarbonyl, $C_7$–$C_{11}$ bicycloalkoxycarbonyl, aryloxycarbonyl, or aryl ($C_1$–$C_{10}$ alkoxy) carbonyl;

$R^{6c}$ is selected from: H, $C_1$–$C_{10}$ alkyl, $C_2$–$C_6$ alkenyl, $C_3$–$C_{11}$ cycloalkyl, $C_4$–$C_{15}$ cycloalkylalkyl, aryl, aryl ($C_1$–$C_{10}$ alkyl)-;

$R^3$ is independently selected from: H, $C_1$–$C_6$ alkyl, $C_3$–$C_6$cycloalkyl, $C_4$–$C_{11}$ cycloalkylalkyl, aryl, aryl ($C_1$–$C_6$ alkyl)-;

v is-Q-Y-;

Q is a heterocyclic ring selected from oxazole, isoxazole, oxazoline, or isoxazoline, said heterocyclic ring being substituted with 0–2 $R^5$, wherein, the bonds between Q and Y and between Q and U are at 1 and 3 positions of Q;

Y is selected from: C(=O) or S(O)$_2$;

R$^5$ is selected independently from: H, F, Cl, Br, I, CF$_3$, CN, CHO, CO$_2$R$^{5a}$, C(=O)R$^{5a}$, CONHR$^{5a}$, CON(R$^{5a}$)$_2$, OC(=O)R$^{5a}$, OCO$_2$R$^{5a}$, OR$^{5a}$, OC(=O) N(R$^{5a}$)$_2$, OCH$_2$CO$_2$R$^{5a}$, CO$_2$CH$_2$CO$_2$R$^{5a}$, N(R$^{12}$)R$^{5a}$, NO$_2$, NR$^{5a}$C(=O)R$^{5a}$, NR$^{5a}$C(=O) OR$^{5a}$, NR$^{5a}$SO$_2$N(R$^{12}$) R$^{5a}$, NR$^{5a}$SO$_2$R$^{5b}$, SR$^{5a}$, S(=O)R$^{5b}$, SO$_2$R$^{5b}$, SO$_2$N (R$^{5a}$)$_2$, C$_1$ to C$_{10}$ alkyl, C$_2$ to C$_6$ alkenyl, C$_2$ to C$_6$ alkynyl, C$_3$ to C$_{11}$ cycloalkyl, C$_4$ to C$_{15}$ cycloalkylalkyl, aryl, aryl(C$_1$–C$_{10}$ alkyl), C$_1$ to C$_6$ alkyl substituted with 0–4 R$^{5c}$,
C$_2$ to C$_6$ alkenyl substituted with 0–4 R$^{5c}$,
C$_2$ to C$_6$ alkynyl substituted with 0–4 R$^{5c}$,
C$_3$ to C$_{11}$ cycloalkyl substituted with 0–3 R$^{5c}$,
C$_4$ to C$_{15}$ cycloalkylalkyl substituted with 0–3 R$^{5c}$,
aryl substituted with 0–3 R$^{5c}$,
aryl(C$_1$–C$_{10}$ alkyl) substituted with 0–3 R$^{5c}$; R$^{5a}$ is selected from: H, C$_1$ to C$_{10}$ alkyl, C$_2$ to C$_6$ alkenyl, C$_3$ to C$_{11}$ cycloalkyl, C$_4$ to C$_{15}$ cycloalkylalkyl, aryl, or aryl(C$_1$–C$_{10}$ alkyl);

R$^{5b}$ is selected from: C$_1$ to C$_{10}$ alkyl, C$_2$ to C$_6$ alkenyl, C$_3$ to C$_{15}$ cycloalkyl, C$_4$ to C$_{11}$ cycloalkylalkyl, aryl, or aryl(C$_1$–C$_{10}$ alkyl);

R$^{5c}$ is selected from: H, halogen, C$_1$–C$_4$ alkyl, C$_1$–C$_3$ haloalkyl, CN, C$_1$–C$_4$ alkoxy, NO$_2$;

R$^8$ is selected from:
H;
C$_1$–C$_6$ alkyl substituted with 0–4 R$^{3a}$;
C$_2$–C$_6$ alkenyl substituted with 0–4 R$^{3a}$;
C$_2$–C$_6$ alkynyl substituted with 0–4 R$^{3a}$;
C$_3$–C$_8$ cycloalkyl substituted with 0–4 R$^{3a}$;
aryl substituted with 0–4 R$^{3a}$;
aryl(C$_1$–C$_6$ alkyl)-substituted with 0–4 R$^{3a}$;
a 5–10 membered heterocyclic ring system having 1–4 heteroatoms selected independently from O, S, and N, said heterocyclic ring being substituted with 0–3 R$^{3a}$;
C$_1$–C$_6$ alkyl substituted with a 5–10 membered heterocyclic ring system having 1–4 heteroatoms selected independently from O, S, and N, said heterocyclic ring being substituted with 0–4 R$^{3a}$;
(R$^{12}$) (R$^{5a}$) NC(=O)-;
piperidyl-C(=O)-;

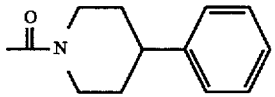

substituted with 0–4 R$^{3a}$; or

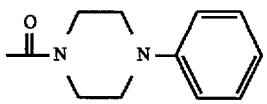

substituted with 0–4 R$^{3a}$;

R$^{3a}$ is selected from H, halogen, C$_1$–C$_8$ alkyl, C$_2$–C$_6$ alkenyl, C$_3$–C$_{11}$ cycloalkyl, C$_4$–C$_{11}$ cycloalkylalkyl, aryl, aryl(C$_1$–C$_6$alkyl)-;

R$^9$ is selected from:
H,
—R$^{15}$,
—N(R$^{6d}$)C(=O)-O-R$^{15a}$,
—N(R$^{6d}$)C(=O)-R$^{15}$,
—N(R$^{6d}$)C(=O)-NH-R$^{15}$,
—N(R$^{6d}$)NH-C(=O)-O-R$^{15a}$,
—N(R$^{6d}$)NH-C(=O)-R$^{15}$,
—N(R$^{6d}$)NH-C(=O)-NH-R$^{15}$,
—N(R$^{6d}$)S(=O)$_2$-O-R$^{15b}$,
—N(R$^{6d}$)S(=O)$_2$-R$^{15}$,
—N(R$^{6d}$)C(=S)NHR$^{15}$,
—N(R$^{6d}$)P(=S)OR$^{15a}$,
—N(R$^{6d}$)P(=O)OR$^{15a}$,
—N(R$^{6d}$)P(=S)(R$^{15a}$)$_2$,
—N(R$^{6d}$)P(=O)(R$^{15a}$)$_2$,
—N(R$^{12}$)(R$^{5a}$),
—CH=CH-R$^{15}$, or
—C≡C—R$^{15}$;

R$^{6d}$ is selected from: H, C$_1$–C$_{10}$ alkyl, C$_2$–C$_6$ alkenyl, C$_3$–C$_{11}$ cycloalkyl, C$_4$–C$_{15}$ cycloalkylalkyl, aryl, aryl (C$_1$–C$_{10}$ alkyl)-;

R$^{15}$ is selected from:
H,
C$_1$–C$_8$ alkyl substituted with 0–4 R$^{3a}$,
C$_2$–C$_8$ alkenyl substituted with 0–4 R$^{3a}$,
C$_2$–C$_8$ alkynyl substituted with 0–4 R$^{3a}$,
C$_3$–C$_8$ cycloalkyl substituted with 0–4 R$^{3a}$,
aryl substituted with 0–4 R$^{3a}$,
aryl(C$_1$–C$_6$ alkyl)-substituted with 0–4 R$^{3a}$,
a 5–10 membered heterocyclic ring system having 1–4 heteroatoms selected independently from O, S, and N, said heterocyclic ring being substituted with 0–3 R$^{3a}$,
C$_1$–C$_6$ alkyl substituted with a 5–10 membered heterocyclic ring system having 1–4 heteroatoms selected independently from O, S, and N, said heterocyclic ring being substituted with 0–4 R$^{3a}$;

R$^{15a}$ is selected from:
C$_1$–C$_8$ alkyl substituted with 0–4 R$^{3a}$,
C$_2$–C$_8$ alkenyl substituted with 0–4 R$^{3a}$,
C$_2$–C$_8$ alkynyl substituted with 0–4 R$^{3a}$,
C$_3$–C$_8$ cycloalkyl substituted with 0–4 R$^{3a}$,
aryl substituted with 0–4 R$^{3a}$,
aryl(C$_1$–C$_6$ alkyl)-substituted with 0–4 R$^{3a}$,
a 5–10 membered heterocyclic ring system having 1–4 heteroatoms selected independently from O, S, and N, said heterocyclic ring being substituted with 0–3 R$^{3a}$,
C$_1$–C$_6$ alkyl substituted with a 5–10 membered heterocyclic ring system having 1–4 heteroatoms selected independently from O, S, and N, said heterocyclic ring being substituted with 0–4 R$^{3a}$;

R$^{10}$ is selected from CO$_2$R$^{16}$, CO$_2$R$^{13b}$, SO$_3$H, tetrazolyl, or PO$_3$H;

R$^{16}$ is selected from: H, C$_1$ to C$_{10}$ alkyl, C$_3$ to C$_{11}$ cycloalkyl, aryl, aryl(C$_1$ to C$_6$ alkyl)-, C$_3$ to C$_{10}$ alkylcarbonyloxyalkyl, C$_3$ to C$_{10}$ alkoxycarbonyloxyalkyl, C$_2$ to C$_{10}$ alkoxycarbonyl, C$_5$ to C$_{10}$ cycloalkylcarbonyloxyalkyl, C$_5$ to C$_{10}$ cycloalkoxycarbonyloxyalkyl, C$_5$ to C$_{10}$ cycloalkoxycarbonyl, aryloxycarbonyl, aryloxycarbonyloxy(C$_1$ to C$_6$ alkyl)-, arylcarbonyloxy (C$_1$ to C$_6$ alkyl)-, C$_5$ to C$_{12}$ alkoxyalkylcarbonyloxyalkyl, (5-(C$_1$–C$_5$ alkyl)-1,3-dioxacyclopenten-2-one-yl)methyl, (5-aryl-1,3-dioxacyclopenten-2-one-yl)methyl, or (R$^{12}$)(R$^5$a)N-(C$_1$–C$_{10}$ alkyl)-;

R$^{13b}$ is selected independently from:
—CH(R$^{36}$)OC(=O)R$^{37}$;

—CH($R^{36}$)OC(=O)O$R^{38}$;

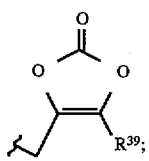

$R^{36}$ is $C_1$–$C_4$ linear alkyl or H;
$R^{37}$ is selected from:
(a) H;
(b) $C_1$–$C_8$ alkyl or $C_3$–$C_8$ cycloalkyl, said alkyl or cycloalkyl being substituted with 1–2 groups independently selected from:
(i) $C_1$–$C_4$ alkyl;
(ii) $C_3$–$C_8$ cycloalkyl;
(iii) $C_1$–$C_5$ alkoxy;
(iv) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —S(=O)($C_1$–$C_5$ alkyl), —$SO_2$($C_1$–$C_5$ alkyl), —OH, —N($R^{12}$)($R^{5a}$), —$CO_2R^{5a}$, —C(=O)N($R^{12}$)($R^{5a}$), or —$C_vF_w$ where v=1 to 3 and w=1 to (2v+1);
(c) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —S(=O)($C_1$–$C_5$ alkyl), —$SO_2$ ($C_1$–$C_5$ alkyl), —OH, —N ($R^{12}$)($R^{5a}$), —$CO_2R^{5a}$, —C(=O)N($R^{12}$)($R^{5a}$), or —$C_vF_w$ where v=1 to 3 and w=1 to (2v+1);

$R^{38}$ is selected from:
(a) $C_1$–$C_8$ alkyl or $C_3$–$C_8$ cycloalkyl, said alkyl or cycloalkyl being substituted with 1–2 groups independently selected from:
(i) $C_1$–$C_4$ alkyl;
(ii) $C_3$–$C_8$ cycloalkyl;
(iii) $C_1$–$C_5$ alkoxy;
(iv) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —S(=O)($C_1$–$C_5$ alkyl), —$SO_2$($C_1$–$C_5$ alkyl), —OH, —N($R^{12}$)($R^{5a}$), —$CO_2R^{5a}$, —C(=O)N($R^{12}$)($R^{5a}$), or —$C_vF_w$ where v=1 to 3 and w=1 to (2v+1);
(b) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —S(=O)($C_1$–$C_5$ alkyl), —$SO_2$($C_1$–$C_5$ alkyl), —OH, —N($R^{12}$)($R^{5a}$), —$CO_2R^{5a}$, —C(=O)N($R^{12}$)($R^{5a}$), or —$C_vF_w$ where v=1 to 3 and w=1 to (2v+1);

$R^{39}$ is $C_1$–$C_4$ alkyl, benzyl, or phenyl.

2. A method for the treatment of thromboembolic disorders which comprises administering to a host in need of such treatment a therapeautically effective amount of a compound of claim 1.

3. A pharmaceutical composition comprising therapeutically effective amount of a compound of claim 1 and a pharmaceutically effective carrier.

4. A method of inhibiting the binding of fibrinogen to blood platelets in a mammal which comprises administering to a mammal in need of such inhibition a therapeutically effective amount of a compound of claim 1.

5. A method of inhibiting the aggregation of blood platelets in a mammal which comprises administering to a mammal in need of such inhibition a therapeutically effective amount of a compound of claim 1.

6. A method of treating thrombus or embolus formation in a mammal which comprises administering to a mammal in need of such treatment a therapeutically effective amount of a compound of claim 1.

7. A method of preventing thrombus or embolus formation in a mammal which comprises administering to a mammal in need of such prevention a therapeutically effective amount of a compound of claim 1.

8. A method for the treatment of thromboembolic disorders in a mammal which comprises administering to a mammal in need of such treatment a therapeutically effective amount of a compound of claim 1 in combination with one or more additional therapeutic agents selected from: a thrombolytic agent, an anti-coagulant agent, or an anti-platelet agent.

9. A method according to claim 8 wherein the thrombolytic agent is plasminogen activator or streptokinase, the anti-coagulant agent is heparin or warfarin, and the anti-platelet agent is aspirin.

10. A pharmaceutical kit for the treatment of thromboembolic disorders comprising one or more containers containing pharmaceutical dosage units comprising a compound of Formula I of claim 1.

* * * * *